(12) United States Patent
Pieken et al.

(10) Patent No.: US 7,427,678 B2
(45) Date of Patent: Sep. 23, 2008

(54) METHOD FOR IMMOBILIZING OLIGONUCLEOTIDES EMPLOYING THE CYCLOADDITION BIOCONJUGATION METHOD

(75) Inventors: Wolfgang Pieken, Boulder, CO (US); Andreas Wolter, Hamburg (DE); David P. Sebesta, Longmont, CO (US); Michael Leuck, Boulder, CO (US); Hallie A. Latham-Timmons, Boulder, CO (US); John Pilon, Ft. Collins, CO (US); Gregory M. Husar, Longmont, CO (US)

(73) Assignee: Sigma-Aldrich Co., St. Louis, MO (US)

( * ) Notice: Subject to any disclaimer, the term of this patent is extended or adjusted under 35 U.S.C. 154(b) by 1126 days.

(21) Appl. No.: 09/845,742

(22) Filed: May 1, 2001

(65) Prior Publication Data
US 2003/0215801 A1 Nov. 20, 2003

Related U.S. Application Data

(63) Continuation-in-part of application No. 09/341,337, filed as application No. PCT/US98/00649 on Jan. 8, 1998, now Pat. No. 6,737,236.

(60) Provisional application No. 60/265,020, filed on Jan. 30, 2001, provisional application No. 60/201,561, filed on May 1, 2000.

(51) Int. Cl.
*C07H 21/00* (2006.01)
*A61K 38/00* (2006.01)
*C07K 1/00* (2006.01)

(52) U.S. Cl. .................... 536/25.3; 536/25.34; 530/338
(58) Field of Classification Search ................ 536/25.3, 536/25.34; 530/338
See application file for complete search history.

(56) References Cited

U.S. PATENT DOCUMENTS

| 4,291,024 | A |   | 9/1981  | Turcotte        |         |
|-----------|---|---|---------|-----------------|---------|
| 4,349,552 | A |   | 9/1982  | Takaya et al.   |         |
| 4,415,732 | A |   | 11/1983 | Caruthers et al.|         |
| 4,458,066 | A |   | 7/1984  | Caruthers et al.|         |
| 4,616,071 | A |   | 10/1986 | Holubka         |         |
| 4,725,677 | A |   | 2/1988  | Koster et al.   |         |
| 5,049,656 | A |   | 9/1991  | Lewis et al.    |         |
| 5,093,232 | A |   | 3/1992  | Urdea et al.    |         |
| 5,118,800 | A |   | 6/1992  | Smith et al.    |         |
| 5,118,802 | A |   | 6/1992  | Smith et al.    |         |
| 5,200,514 | A |   | 4/1993  | Chu             |         |
| 5,221,736 | A | * | 6/1993  | Coolidge et al. | 536/25.31 |
| 5,393,877 | A |   | 2/1995  | McLean et al.   |         |
| 5,420,276 | A |   | 5/1995  | Norbeck         |         |
| 5,464,759 | A |   | 11/1995 | Coolidge et al. |         |
| 5,466,786 | A |   | 11/1995 | Buhr et al.     |         |
| 5,539,082 | A |   | 7/1996  | Nielsen et al.  |         |
| 5,552,535 | A |   | 9/1996  | McLean et al.   |         |
| 5,576,429 | A |   | 11/1996 | Johansson et al.|         |
| 5,580,697 | A |   | 12/1996 | Keana et al.    |         |
| 5,874,532 | A | * | 2/1999  | Pieken et al.   | 530/338 |
| 6,090,932 | A |   | 7/2000  | McGee et al.    |         |
| 6,107,479 | A |   | 8/2000  | Natt et al.     |         |
| 6,171,797 | B1|   | 1/2001  | Perbost         |         |
| 6,262,251 | B1| * | 7/2001  | Pieken et al.   | 536/25.3 |

FOREIGN PATENT DOCUMENTS

| DE | 25 31 257     | 1/1976  |
| DE | 2931233       | 2/1981  |
| DE | 19935204      | 2/2001  |
| EP | 0 453 247 A2  | 10/1991 |
| EP | 0 294 196 B1  | 3/1996  |
| EP | 0 982 311 A2  | 3/2000  |
| WO | WO 91/06556   | 5/1991  |
| WO | WO 91/10671   | 7/1991  |
| WO | WO 91/13900   | 9/1991  |
| WO | WO 92/06103   | 4/1992  |
| WO | WO 94/13789   | 6/1994  |
| WO | WO 95/24185   | 9/1995  |
| WO | WO 96/34984   | 11/1996 |
| WO | WO 97/14706   | 4/1997  |
| WO | WO 98/30575   | 7/1998  |
| WO | WO 98 30578 A | 7/1998  |
| WO | WO 98 47910 A | 10/1998 |
| WO | WO 01/84234   | 11/2001 |
| WO | WO 01/96357 A2| 12/2001 |
| WO | WO 02/20541 A2| 3/2002  |

OTHER PUBLICATIONS

Koch et al. (2000) Bioconjugate Chem. 11:474-483.
Koch et al. Polystyrene or Polycarbonate Plates/Anthraquinone Oligos or cDNA with Irradiation, Exiqon, 1999.
Bruick et al. (1996) Chemistry & Biology 3:49-56.
Bruick et al. (1997) Nucleic Acids Res. 25:1309-1310.

(Continued)

*Primary Examiner*—Jezia Riley

(57) ABSTRACT

This invention discloses a novel method for immobilizing molecules to a support. Specifically, this invention discloses a method of immobilizing derivatized biomolecules, such as oligonucleotides, using cycloaddition reactions, such as the Diels-Alder reaction. Included in this invention are the novel immobilized biomolecules that can be prepared according to the method of this invention.

20 Claims, 12 Drawing Sheets

OTHER PUBLICATIONS

Eritja et al. (1991) Tetrahedron 47:4113-4120.
Goodchild (1990) Bioconjugate Chemisry 1:166-187.
Haralambidis et al. (1990) Nucleic Acids Res. 18:493-499.
Haralambidis et al. (1987) Tetrahedron Lett. 28:5199-5202.
Jones et al. (1995) J. Med. Chem. 38:2138.
Juby et al. (1991) Tetrahedron Lett. 32:879-822.
Krieg et al. (1991) Antisense Res. and Dev.1:161.
Leonetti et al. (1990) Bioconjugate Chem. 1:149-153.
Mori et al. (1989) Nucleosides & Nucleotides 8:649.
Sinha and Cook (1988) Nucleic Acids Res. 16:2659.
Smith et al. (1987) Methods in Enzymology, 155:260-301.
Sproat et al. (1987) Nucleic Acids Research 15:6181-6188.
Theisen et al. (1992) Tetrahedron Lett. 33:5033-5036.
Tung (1991) Bioconjugate Chem. 2:464-465.
Zalipsky (1995) Bioconjugate Chem. 6:150-165.
U.S. Appl. No. 09/845,742, filed May 1, 2001, Pieken et al.
Agrawal and Khorana (May 1972) J. of the American Chem. Society 94(10):3578-3585.
Andrus et al. (1988) Tetrahedron Letters 29:861-864.
Bannwarth and Wippler (1990) Helv. Chim. Acta 73:1139-1147.
Bayer and Mutter (Jun. 1972) Nature 237;512-513.
Beaucage and Iyer (1993) Tetrahedron 49(10):1925-1963.
Blackburn and Guo (1992) Tetrahedron Letters 34(1):149-152.
Duggan and Imagire (Feb. 1989) Synthesis 131-132.
Eadie and Davidson (1987) Nucleic Acid Research 15(20):8333-8349.
Hill et al. (2001) J. Org. Chem. 66:5352-5358.
March, J. ed (1992) in *Advanced Organic Chemistry* 839-852.
Natt and Häner (1997) Tetrahedron 53(28):9629-9636.
Rideout and Breslow. (1980) J. Am. Chem. Soc. 102:7816-7817.
Yu et al. (1994) Tetrahedron Letters 35:8565-8568.
Aurup et al. (1992) Biochemistry 31:9636-9641.
Beaucage and Iyer (1992) Tetrahedron 48:2223-2311.
Englisch and Gauss (Jun. 1991) Angew. Chem. Int. Ed. Engl. 30:613-627.
Fischer et al. (1990) BioTechniques 9:300-301.
Gryaznov et al. (Jun. 1995) Proc. Nat. Acad. Sci. 92:5798-5802.
Hardy et al. (1994) Nucleic Acids Res. 22:2998-3004.
Huryn and Okabe (1992) Chemical Reviews 92:1745-1768.
Johnson et al. (1990) BioTechniques 8:424-428.
Kumar and Poonian (1984) J. Org. Chem. 49:4905-12.
Ludwig and Eckstein (1989) J. Org. Chem. 54:631-635.
McBride and Caruthers (1983) Tetrahedron Letters 24:245-248.
McBride et al. (1988) BioTechniques 6:362-367.
Micklefield (2001) Current Medicinal Chemistry 8:1157-1179.
Mikhailopulo et al. (1993) Liebigs Ann. Chem. pp. 513-519.
Nishikubo et al. (1981) Tetrahedron Letters 22:3873-3874.
Ono et al. (1995) Nucleic Acids Res. 23:4677-82.
Reddy et al. (1987) Tetrahedron Letters 28:23-26.
Robles et al. (1995) Nucleic Acids Res. 23:4151-61.
Roush et al. (1983) Tetrahedron Letters 24:1377-1380.
Schmidt (Apr. 1994) Synlett 4:241-242.
Shibuya and Ueda (1980) Chem. Pharm. Bull. 28:939-946.
Sinha et al. (1983) Tetrahedron Letters 24:5843-5846.
Tronchet et al. (1990) Tetrahedron Letters 31:531-534.
Tronchet et al. (1988) Nucleosides & Nucleotides 7:249-269.
Verheyden et al. (1971) J. Org. Chem. 36:250-254.
Wagner et al. (1991) Nucleic Acids Res. 19:5965-5971.
Warshaw et al. (1990) J. Med. Chem. 33:1663-1666.
Giuliano et al. (1993) *J. Org. Chem. 58*:4979-4988.
Giuliano et al. (1990) *J. Org. Chem. 55*:3555-3562.
Jager et al. (1995) *Tetrahedron Letters 36*:861-864.
Lubineau et al. (1995) *Carbohydrate Research 270*:163-179.

* cited by examiner

METHOD FOR IMMOBILIZING OLIGONUCLEOTIDES EMPLOYING THE CYCLOADDITION BIOCONJUGATION METHOD

RELATED APPLICATIONS

This application claims the benefit of U.S. Provisional Application Ser. No. 60/201,561, filed May 1, 2000 and U.S. Provisional Application Ser. No. 60/265,020, filed Jan. 30, 2001, both entitled "Immobilization of Oligonucleotides Employing the Cycloaddition Bioconjugation Method." This application is also a continuation in part of U.S. application Ser. No. 09/341,337, filed Jul. 8, 1999, now U.S. Pat. No. 6,737,236 which is a 371 filing of International Application No. PCT/US98/00649 (WO 98/30575), filed Jan. 8, 1998, both entitled "Bioconjugation of Macromolecules."

FIELD OF THE INVENTION

This invention describes a novel method for immobilizing molecules on a support. Particularly, this invention describes a method for immobilizing biomolecules on a support using cycloaddition reactions, such as the Diels-Alder reaction.

BACKGROUND OF THE INVENTION

Applications for surface immobilized biomolecules are widespread and include nucleic acid sequencing, gene expression profiling, analysis for single nucleotide polymorphisms (SNPs) and evaluation of hapten-antibody or ligand-target interactions. An important subset of these techniques involves immobilization of oligonucleotide probes that employ Watson-Crick hybridization in the interaction with target nucleic acids such as genomic DNA, RNA or cDNA prepared via Polymerase Chain Reaction (PCR) amplification of sample DNA. Current technologies often involve formatting oligonucleotide probes for such analyses into microarrays on glass slides, silicon chips or wafers, micro titer plates or other supports including polyacrylamide gel matrices.

A variety of methods exist for immobilizing biomolecules, including non-covalent (hydrophobic or ionic interactions) as well as covalent methods. A number of these methods are summarized in Table 1. Methods involving covalent attachment are generally considered preferable, as more stringent conditions may be applied to the immobilized system for the reduction of non-specific ionic or hydrophobic associations (which raise background signal) without concern for the loss of the probe from the surface. Commonly employed covalent methods include condensation of amines with activated carbonyl groups on the surface, such as activated carboxylic acid esters, carbonates or isocyanates or isothiocyanates. Additionally, amine groups can be condensed with aldehydes under reductive amination conditions to afford secondary amine linkages between the surface and the biomolecule. Furthermore, amines can be condensed with electron deficient heterocycles via nucleophilic aromatic substitution as well as epoxide opening.

Cycloaddition reactions can be defined as any reaction between two (or more) moieties (either intra or intermolecular) where the orbitals of the reacting atoms form a cyclic array as the reaction progresses (typically in a concerted fashion although intermediates may be involved) along the reaction coordinate leading to a product. The orbitals involved in this class of reactions are typically $\pi$ systems although certain $\sigma$ orbitals can also be involved. The number of electrons associated with this type of reaction are of two types: $4n+2$ and $4n$, where $n=0, 1, 2, 3, 4$, etc. Typical examples of cycloaddition reactions include Diels-Alder cycloaddition reactions, 1,3-dipolar cycloadditions and [2+2] cycloadditions.

The Diels-Alder reaction, by far the most studied cycloaddition, is the cycloaddition reaction between a conjugated diene and an unsaturated molecule to form a cyclic compound with the $\pi$-electrons being used to form the new $\sigma$-bonds. The Diels-Alder reaction is an example of [4+2] cycloaddition reaction, as it involves a system of $4\pi$-electrons (the diene) and a system of $2\pi$-(the dienophile). The reaction can be made to occur very rapidly, under mild conditions, and for a wide variety of reactants. The Diels-Alder reaction is broad in scope and is well known to those knowledgeable in the art. A review of the Diels-Alder reaction can be found in "Advanced Organic Chemistry" (March, J., ed.) 839-852 (1992) John Wiley & Sons, NY, which is incorporated herein by reference.

It has been discovered that the rate of Diels-Alder cycloaddition reactions is enhanced in aqueous solvents. (Rideout and Breslow (1980) J. Am. Chem. Soc. 102:7816). (A similar effect is also seen with 1,3-dipolar cycloaddition reactions (Engberts (1995) Tetrahedron Lett. 36:5389). This enhancement is presumably due to the hydrophobicity of the diene and dienophile reactants. (Breslow (1991) Acc. Chem. Res. 24:159). This effect extends to intramolecular Diels-Alder reactions. (Blokzijl et al. (1991) J. Am. Chem. Soc. 113:4241). Not only is the reaction rate accelerated in water, but several examples of an increased endo/exo product ratio are also reported. (Breslow and Maitra (1984) Tetrahedron Lett. 25:1239; Lubineau et al. (1990) J. Chem. Soc. Perkin Trans. I, 3011; Grieco et al. (1983) Tetrahedron Lett. 24:1897). Salts which increase the hydrophobic effect in water, such as lithium chloride (Breslow et al. (1983) Tetrahedron Lett. 24:1901) and also monovalent phosphates (Pai and Smith (1995) J. Org. Chem. 60:3731) have been observed to further accelerate the rate of [4+2] cycloadditions.

In U.S. application Ser. No. 09/051,449, filed Apr. 6, 1998; Ser. No. 08/843,820, filed Apr. 21, 1997 and Ser. No. 09/402,430, filed Oct. 7, 1999; each entitled "Method for Solution Phase Synthesis of Oligonucleotides," the Diels-Alder cycloaddition reaction is shown to be an ideal method for anchoring oligonucleotides onto resins. Resins derivatized with a diene or dienophile are reacted with an oligonucleotide derivatized with a dienophile or diene, respectively, to yield the Diels-Alder cycloaddition product. In particular, Diels-Alder reactions between oligonucleotides derivatized with a diene and polymeric resins derivatized with maleimide groups and with phenyl-triazoline-diones (PTAD) are described. The resulting resins can be used as affinity chromatography resins.

U.S. application Ser. No. 09/341,337, filed Jul. 7, 1999, entitled "Bioconjugation of Macromolecules," illustrates that cycloaddition reactions in general, such as the Diels-Alder reaction and 1,3-dipolar cycloaddition reactions, are an ideal replacement for current methods of conjugating macromolecules with other molecular moieties. The Diels-Alder reaction, in particular, is an ideal method for covalently linking large water soluble macromolecules with other compounds as the reaction rate is accelerated in water and can be run at neutral pH. (Rideout and Breslow (1980) J. Am. Chem. Soc. 102:7816). Additionally, the nature of the reaction allows post-synthetic modification of the hydrophilic macromolecule without excess reagent or hydrolysis of the reagent. With respect to conjugation to oligonucleotides, this technology has been aided by the ability to efficiently synthesize 2'-O-diene-nucleosides, which allows the conjugation site to be varied throughout the oligonucleotide or the option of having multiple conjugation sites.

The present invention describes a method for immobilizing molecules, particularly biomolecules, to a support using the cycloaddition bioconjugation method. Immobilization of biomolecules via cycloaddition, particularly Diels-Alder reactions, offers the following major advantages over conventional methods (cf. Table 1): cycloaddition reactions establish a covalent and stable linkage between the linked compounds; the reaction proceeds with high chemoselectivity; functional groups of biomolecules do not interfere with the cycloaddition reaction; the cycloaddition reaction is orthogonal to other immobilization/labeling protocols, thus two-fold reactions are possible in one reaction mixture; in contrast to general techniques in organic synthesis, as discussed above, Diels-Alder reactions, can be carried out in aqueous phase, the Diels-Alder reaction is tremendously accelerated in water and is very fast at room temperature or slightly below; the cycloaddition reaction proceeds under neutral conditions in a one-step procedure; no by-products are formed during the reaction; no activators or additives are necessary to run the reaction and the moieties involved in the reaction (dienes and dienophiles) are stable under various reaction conditions employed for conjugation or immobilization of biomolecules Note, that throughout this application various citations are provided. Each citation is specifically incorporated herein by reference in its entirety.

SUMMARY OF THE INVENTION

The present invention describes a novel, chemoselective and highly efficient method for immobilizing molecules using cycloaddition reactions. The method of the invention offers advantages over existing immobilization methods that can suffer from cross-reactivity, low selectivity, mechanistic ambiguity and competitive hydrolysis of reactive groups.

In summary, the method of the instant invention comprises the step of reacting a derivatized molecule with a derivatized support capable of reacting with said derivatized molecule via a cycloaddition reaction. In a preferred embodiment, the derivatized molecule is a biomolecule, preferably an oligonucleotide, but could also be a hapten, carbohydrate, oligosaccharide, peptide and protein (including an antibody). The support is preferably glass or controlled pore glass (CPG), but could also be polypropylene, polystyrene, polyacrylamide or silicon. In a preferred embodiment, the cycloaddition reaction is a Diels-Alder cycloaddition reaction between the support and the biomolecule. Therefore, the biomolecule is preferably derivatized with one component of a Diels-Alder reaction, i.e., a diene or a dienophile, and the support is derivatized with the appropriate counterpart reactant, i.e., a dienophile or a diene, respectively.

This invention includes a reaction scheme for producing a wide variety of immobilized biomolecules using cycloaddition reactions as typified by the Diels-Alder cycloaddition reaction. The method of this invention can be extended to the immobilization of any molecule, particularly biomolecules on any support that can be appropriately derivatized.

The method of this invention can be extended to all 4n and 4n+2 cycloadditions (where n=0, 1, 2, 3, 4, etc.). This includes, but is not limited to Diels-Alder cycloadditions, 1,3-dipolar cycloadditions, ene cycloaddition reactions and [2+2] (a 4n type) cycloadditions, such as ketene additions and photochemical [2+2] additions.

Also described herein is a method by which surfaces, preferably glass microscope slides or CPG, may be converted into reactive elements for the cycloaddition immobilization method of the invention by deposition of silane monolayers appropriately functionalized with reaction components for cycloaddition reactions.

Also included in this invention are any novel immobilized and derivatized molecules and derivatized supports produced by the method of the invention.

The method of the invention is applicable to the fields of biomolecule array fabrication for research, development and clinical diagnostic applications relating to nucleic acid sequencing, gene expression profiling, analysis of single nucleotide polymorphisms (SNPs) and evaluation of hapten-antibody or ligand-target interactions.

BRIEF DESCRIPTION OF THE FIGURES

FIG. 3 is a fluorescence scan of maleimide derivatized CPG.

FIG. 5 is a fluorescence scan of diene functionalized CPG.

FIG. 12 illustrates fluorescence scans of CPG samples showing Diels-Alder surface immobilization of an oligonucleotide (maleimide-oligonucleotide (26)) on diene-functionalized CPG.

DETAILED DESCRIPTION OF THE INVENTION

Figure 1:
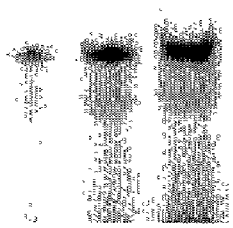
FIG. 1 is a fluorescence scan of polyacrylamide gel loaded with 1, 2 and 3 µL of fluorescein labeled compound (26), the synthesis of which is described in Example 6.

The present invention includes a method for immobilizing molecules on a support. Specifically, the present invention describes the use of cycloaddition reactions, in particular the Diels-Alder cycloaddition reaction for the chemoselective immobilization of molecules on a support.

The method of the instant invention comprises the step of reacting a derivatized molecule with a derivatized support capable of reacting with said derivatized molecule via a cycloaddition reaction. In a preferred embodiment, the derivatized molecule is a biomolecule, most preferably an oligonucleotide and the support is preferably glass or controlled pore glass (CPG). In a preferred embodiment, the cycloaddition reaction is a Diels-Alder cycloaddition reaction. Therefore, the biomolecule is derivatized with one component of a Diels-Alder reaction, i.e., a diene or a dienophile, and the support is derivatized with the appropriate counterpart reactant, i.e., a dienophile or a diene, respectively.

This invention includes a reaction scheme for producing a wide variety of immobilized biomolecules using cycloaddition reactions as typified by the Diels-Alder cycloaddition reaction. The method of this invention can be used to immobilize any molecule, particularly biomolecules, on any support that can be appropriately derivatized.

Certain terms used to describe the invention are described herein as follows:

"Oligonucleotide" refers to a polynucleotide formed from a plurality of linked nucleotide units. The nucleotide units each include a nucleoside unit linked together via a phosphate linking group. The term oligonucleotide also refers to a plurality of nucleotides that are linked together via linkages other than phosphate linkages such as phosphorothioate linkages. The oligonucleotide may be naturally occurring or non-naturally occurring. In a preferred embodiment the oligonucleotides of this invention have between 1-1,000 nucleotides.

For the purposes of this invention "nucleobase" will have the following definition. A nucleobase is a purine or a pyrimidine base. Nucleobase includes all purines and pyrimidines currently known to those skilled in the art or any chemical modifications thereof. The purines are attached to the ribose ring through the nitrogen in the 9 position of the purine ring and the pyrimidines are attached to the ribose ring through the nitrogen in the 1 position of the pyrimidine ring. The pyrimidine can be modified at the 5- or 6-position of the pyrimidine ring and the purine can be modified at positions 2-, 6- or 8- of the purine ring. Certain modifications are described in U.S. patent application Ser. No. 08/264,029, filed Jun. 22, 1994, entitled "Novel Method of Preparation of Known and Novel 2' Modified Pyrimidines Intramolecular Nucleophilic Displacement" and U.S. Pat. No. 5,428,149, entitled "Method for Palladium Catalyzed Carbon-Carbon Coupling and Products" which are herein incorporated by reference. More specifically a nucleobase includes, but is not limited to, uracil, cytosine, N4-protected cytosine, 4-thiouracil, isocytosine, 5-methyluracil (thymine), 5-substituted uracils, adenine, N6-protected adenine, guanine, N2-protected guanine, 2,6-diaminopurine, halogenated purines as well as heterocycles meant to mimic the purine or pyrimidine ring, such as imidazole.

A "diene" is defined as a molecule bearing two conjugated double bonds. The diene may even be non-conjugated, if the geometry of the molecule is constrained so as to facilitate a cycloaddition reaction (Cookson (1964) J. Chem. Soc. 5416). The atoms forming these double bonds can be carbon or a heteroatom or any combination thereof.

A "dienophile" is defined as a molecule bearing an alkene group, or a double bond between a carbon and a heteroatom, or a double bond between two heteroatoms.

The dienophile can be any group, including but not limited to, a substituted or unsubstituted alkene, or a substituted or unsubstituted alkyne. Typically, the dienophile is a substituted alkene of the formula $C=C-Z$ or $Z'-C=C-Z$, wherein Z and Z' are electron withdrawing groups independently selected from the group consisting of CHO, COR, COOH, COCl, COaryl, CN, $NO_2$, aryl, $CH_2OH$, $CH_2Cl$, $CH_2NH_2$, $CH_2CN$, $CH_2COOH$, halogen, or $C=C$. In certain cases the groups attached to the alkene unit can be electron donating groups, including but not limited to phenyl rings, conjugated double bonds, alkyl groups, OMe groups or other X-alkyl moieties wherein X is an electron donating group (these type of dienophiles undergo cycloadditions that are known generally as reverse electron demand cycloadditions). Other examples of dienophiles include compounds having the formula, $R_2C=X$, wherein X is a heteroatom, selected from the group consisting of oxygen, nitrogen, phosphorus and sulfur. For example, molecules bearing a primary amino group, such as amino acids or a lysine containing peptide, can be converted to efficient dienophiles by reaction with formaldehyde to yield their corresponding iminium salts as illustrated below. The latter undergo Diels-Alder cycloaddition with macromolecules bearing a diene group under mild conditions in aqueous solvents.

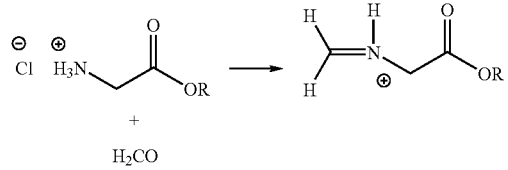

A "1,3-dipole" is defined as a compound that contains a consecutive series of three atoms, a-b-c, where atom a contains a sextet of electrons in its outer shell and atom c contains an octet with at least one unshared pair of electrons in its outer shell. Because molecules that have six electrons in the outer shell of an atom are typically unstable, the a-b-c atom example is actually one canonical structure of a resonance hybrid, where at least one structure can be drawn. 1,3-dipoles can be divided into two main groups:

1) Systems in which one of the canonical forms has a double bond on the sextet atom (atom a) and the other canonical form has a triple bond on that atom:

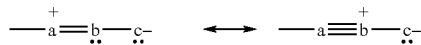

2) Systems where the dipolar canonical form has a single bond on the sextet atom (atom a) and the other canonical form has a double bond on that atom:

For a review of this reaction type see "Advanced Organic Chemistry" (March, J., ed.) 836-839 (1992) John Wiley & Sons, NY, and "Frontier Orbitals and Organic Chemical Reactions" (I. Fleming) 148-161 (1976) John Wiley & Sons, Ltd. Typical examples of 1,3-dipoles include, but are not limited to nitrile ylids, nitrile imines, nitrile oxides, diazoalkanes, azides, azomethine ylids, azomethine imines, nitrones, carbonyl ylids, carbonyl imines and carbonyl oxides.

A "1,3-dipolarophile" is defined in the same manner as a "dienophile" or "diene" (as described above). The macromolecule can be attached to either (or both) the 1,3-dipole or the 1,3-dipolarophile.

A "1,3-dipolar cycloaddition reaction" can be generally represented as follows:

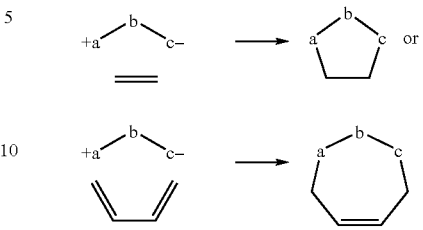

An "Ene reaction" can be generally represented as follows:

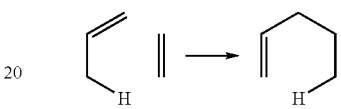

The reaction partners in an Ene reaction are referred to as an "ene" and an "enophile." An "enophile" is defined in the same manner as a "dienophile" (see the above description for dienophile). An "ene" can be any unsaturated group, including but not limited to, a substituted or unsubstituted alkene, or a substituted or unsubstituted alkyne. Typically, the "ene" is a substituted alkene of the formula $X-C=CH-CH_2-$ or $X'-C=C-X-CXH-$, wherein X and X' are electron donating groups. The macromolecule can be attached to either (or both) the ene component or the enophile component.

"Bioconjugate" as defined herein refers to any macromolecule which has been derivatized with another molecular entity. "Bioconjugation" or "Conjugation" refers to the derivatization of a macromolecule with another molecular entity.

As used herein a "support" refers to glass, including but not limited to controlled pore glass (CPG), glass slides, glass fibers, glass disks, materials coated with glass, silicon chips and wafers including, but not limited to metals and composites containing glass; polymers/resins, including but not limited to polystyrene (PS), polyethylene glycol (PEG), copolymers of PS and PEG, copolymers of polyacrylamide and PEG, copolymers containing maleimide or maleic anhydride, polyvinyl alcohol and non-immunogenic high molecular weight compounds; and large biomolecules, including but not limited to polysaccharides, such as cellulose, proteins and nucleic acids. The support can be, but is not necessarily, a solid support.

As used herein "immobilization" refers to the attachment, via covalent bond, to a support. Immobilization includes a functionality on the support or a derivatized support.

The term "functionality" as used herein refers to functional groups, including but not limited to alcohols, carboxylates, amines, sulfonic acids and halides, that allow the attachment of one component of the cycloaddition system (e.g. a diene or a dienophile).

As used herein "derivatized" refers to molecules and/or supports that have been functionalized with a moiety capable of undergoing a cycloaddition reaction. A molecule or support that bears a moiety capable of undergoing a cycloaddition reaction without functionalization also falls within this definition. Examples of moieties capable of undergoing a cycloaddition reaction, include but are not limited to a diene, dienophile, 1,3-dipole, 1,3-dipolarophile, ene, enophile or other moiety capable of undergoing a cycloaddition reaction.

The term "molecule" includes, but is not limited to biomolecules, macromolecules, diagnostic detector molecules (DDM's) and other small molecules, particularly small molecules for use in combinatorial chemistry.

As used herein a "biomolecules" include, but are not limited to nucleic acids, oligonucleotides, proteins, peptides and amino acids, polysaccharides and saccharides, glycoproteins and glycopeptides (in general, glycoconjugates) alkaloids, lipids, hormones, drugs, prodrugs, antibodies and metabolites.

The term "macromolecules" as used herein refers to the product of the coupling of two macromolecules via cycloaddition.

"Diagnostic detector molecules" ("DDM's") include, but are not limited to fluorescent, chemiluminescent, radioisotope and bioluminescent marker compounds; antibodies, biotin and metal chelates.

As used herein "cycloaddition reaction" refers to any reaction that occurs between two reactants by a reorganization of valence electrons through an activated complex, which is usually a cyclic transition state. The orbitals involved in this class of reactions are typically π-systems although certain σ-orbitals can also be involved. The number of electrons associated with this type of reaction are of two types; $4n+2$ and $4n$, where $n=0, 1, 2, 3, 4$, etc. Typical examples of cycloaddition reactions include, but are not limited to [1+2]-cycloaddition, such as reaction between carbenes and olefins, [2+2]-cycloaddition, such as reaction between olefins or reaction between ketenes and olefins, [3+2]-cycloaddition, such as 1,3-dipolar cycloaddition, [2+4]-cycloaddition, such as the Diels-Alder reaction and ene reaction, [4+6]-cycloaddition, and cheleotropic reactions. Types of reactants involved in cycloaddition reactions include, but are not limited to, olefins, including but not limited to alkenes, dienes etc with or without heteroatoms, alkynes, with and without heteroatoms, aromatic compounds, such as anthracene, 1,3-dipoles, carbenes and carbene-precursors.

The "derivatized oligonucleotides" of this invention are generally represented by the following formulas:

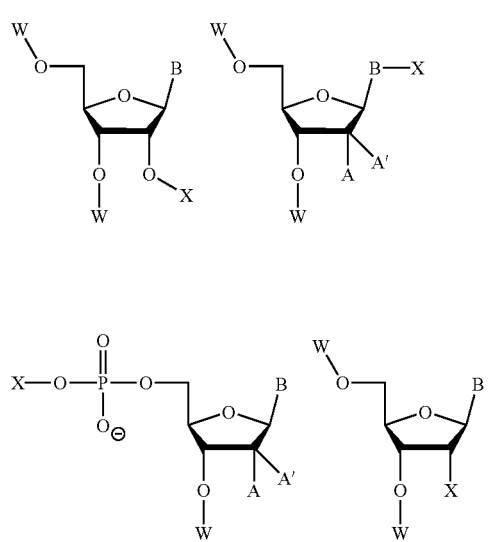

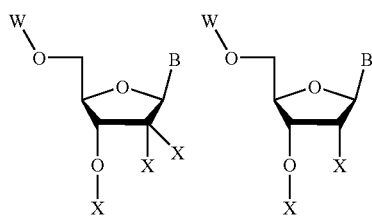

wherein

B is a nucleobase;

A and A' are 2'-sugar substituents;

W is independently selected from the group consisting of an oligonucleotide having between 1-1000 nucleobases, X or H; and X is a diene, dienophile, 1,3-dipole, 1,3 dipolarophile, ene, enophile, alkene, alkyne or other moiety capable of undergoing a cycloaddition reaction, additionally when X is attached to nucleobase B it can be attached to a carbon atom, an exocyclic nitrogen or an exocyclic oxygen.

In a preferred embodiment of the invention:

A and A' are independently selected from the group consisting of H, $^2$H, $^3$H, Cl, F, OH, NHOR$^1$, NHOR$^3$, NHNHR$^3$, NHR$^3$, =NH, CHCN, CHCl$_2$, SH, SR$_3$, CFH$_2$, CF$_2$H, CR$^2$$_2$Br, —(OCH$_2$CH$_2$)$_n$OCH$_3$, OR$^4$ and imidazole (see U.S. patent application Ser. No. 08/264,029, filed Jun. 22, 1994, entitled "Novel Method of Preparation of 2' Modified Pyrimidines Intramolecular Nucleophilic Displacement," which is incorporated herein by reference);

R$^1$ is selected from the group consisting of H and an alcohol protecting group;

R$^2$ is selected from the group consisting of =O, =S, H, OH, CCl$_3$, CF$_3$, halide, optionally substituted C$_1$-C$_{20}$ alkyl (including cyclic, straight chain, and branched), C$_2$-C$_{20}$ alkenyl, C$_6$-C$_{20}$ aryl, C1-C20 acyl, C$_1$-C$_{20}$ benzoyl, OR$_4$ and esters;

R$^3$ is selected from the group consisting of R$^2$, R$^4$, CN, C(O)NH$_2$, C(S)NH$_2$, C(O)CF$_3$, SO$_2$R$^4$, amino acid, peptide and mixtures thereof;

R$^4$ is selected from the group consisting of an optionally substituted hydrocarbon (C$_1$-C$_{20}$ alkyl, C$_2$-C$_{20}$ alkenyl, C$_2$-C$_{20}$ alkynyl), an optionally substituted heterocycle, t-butyldimethylsilyl ether, triisopropylsilyl ether, nucleoside, carbohydrate, fluorescent label and phosphate;

Most preferably A is selected from the group consisting of H, OH, NH$_2$, Cl, F, NHOR$^3$, OR$^4$, OSiR$^4$$_3$. (See U.S. patent application Ser. No. 08/264,029, filed Jun. 22, 1994, entitled "Novel Method of Preparation of 2' Modified Pyrimidines Intramolecular Nucleophilic Displacement," filed Jun. 22, 1994); and X includes, but is not limited to an alkyl or substituted alkyl group bearing a conjugated diene unit, an alkoxy or substituted alkoxy group bearing a conjugated diene unit, CH$_2$CH$_2$CH=CHCH$_2$CH$_2$O, maleimide substituted alkoxy groups, dienophile substituted alkoxy groups, an alkylamino group or substituted alkylamino group bearing a conjugated diene unit, maleimide substituted alkylamino groups or substituted alkylamino groups, an alkylamino group or substituted alkylamino group bearing a dienophile moiety, a nitrile ylid, nitrile imine, nitrile oxide, diazoalkane, azide, azomethine ylid, azomethine imine, nitrone, carbonyl ylid, carbonyl imine and carbonyl oxide.

The alkyl groups on all the above listed moieties can have between 1-50 carbons, preferably 1-30 carbons.

As used herein a "linking molecule" is a molecular entity that connects two or more molecular entities through covalent interactions. More specifically a linking molecule is a multifunctional molecule that can be used to derivatize a molecule or support with a diene, dienophile or other moiety capable of undergoing a cycloaddition reaction. The linking molecules of this invention are generally represented by the following formulas:

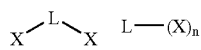

wherein

X is as defined above;

n is an integer from 1-20; and

L is a linker which includes, but is not limited to, compounds of the following general formula:

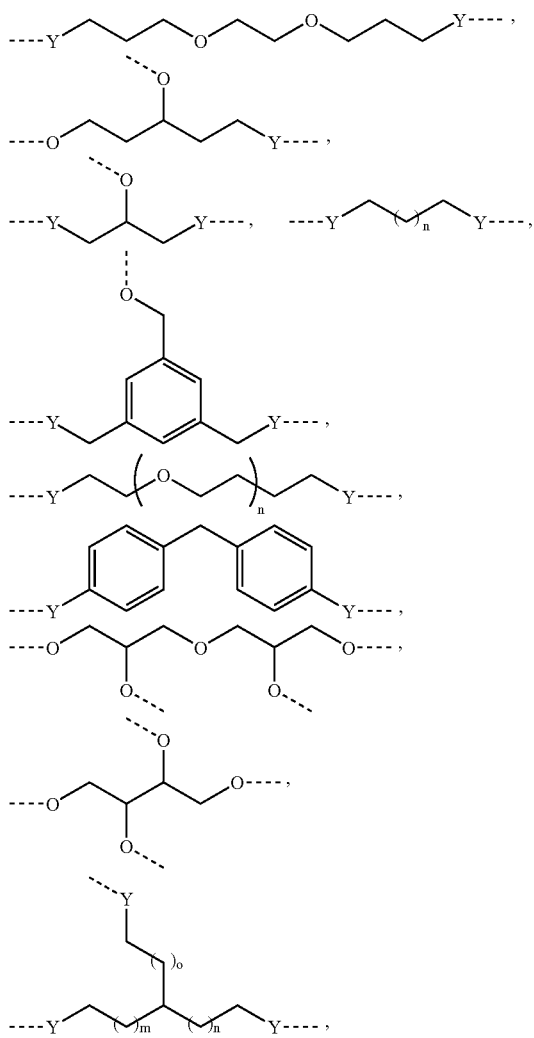

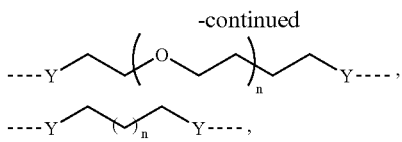

wherein m, n, o is equal to 0, 1, 2 and

Y is selected from NH, O, NH(CO)O, NH(CS)O, NH(CO)NH, NH(CO), S—S—S—, Si(OR)$_3$ and SiR$_2$ wherein R is selected from alkyl, aryl, substituted alkyl or substituted aryl, each having between 1-50 carbon atoms.

Other obvious substitutions for the substituents described above are also included within the scope of this invention, which is not limited to the specific, but rather the generalized formula of reaction.

Cycloaddition reactions, particularly Diels-Alder reactions, are uniquely suited as a general method for the immobilization of molecules, particularly biomolecules to a support. The cycloaddition of a diene and a dienophile is highly chemoselective and only a suitably electronically configured diene and dienophile pair will react. The reaction proceeds under mild conditions in a reasonable time-frame. Biomolecules such as nucleic acids, oligonucleotides, proteins, peptides, carbohydrates, polysaccharides, glycoproteins, antibodies and lipids generally do not contain moieties that can undergo such a cycloaddition reaction. Thus, by specific introduction of a diene and dienophile reaction partner, biomolecule immobilization to a support becomes possible with unprecedented specificity.

The high selectivity of a diene or dienophile for reaction with the corresponding dienophile or diene, respectively, eliminates the need to protect functional groups during the synthesis of biomolecules, such as oligonucleotides or peptides. This is a tremendous practical advantage over other functional groups used for immobilization in biomolecular synthesis, in which the limited selectivity of the protection chemistry often determines the immobilization yields. Additionally, the diene and dienophiles are not susceptible to the side-reactions typically encountered in known immobilization methods. Because they do not undergo hydrolysis or solvolysis reactions, these reactions can be performed in aqueous media at near stoichiometric concentrations and thus conserve precious reagent. The lack of such side reactions allows immobilization of biomolecules in unprecedented yields and purities. The Diels-Alder cycloaddition reaction is accelerated by aqueous solvents and therefore, uniquely suited for the derivatization or immobilization of hydrophilic biomolecules. Finally, this method is typically much less pH sensitive than most known alternatives.

In one embodiment of the present invention the biomolecule is an oligonucleotide. The solvent of choice for the derivatization of oligonucleotides is water, due to the highly anionic nature of these molecules. Thus, an optimal reaction for the immobilization of such groups proceeds readily in water, and displays no side reactions with water, such as hydrolysis of any of the reactants. Based on these criteria for optimal and specific immobilization of oligonucleotides, this disclosure describes the use of Diels-Alder cycloadditions for the chemoselective and efficient immobilization oligonucleotides on a support. Thus, an oligonucleotide bearing either a diene modified nucleoside or non-nucleoside phosphate diester group, or a dienophile modified nucleoside or non-nucleoside phosphate diester group can be reacted with a support bearing either a dienophile or a diene moiety, respectively.

The diene or dienophile moiety can be incorporated into the oligonucleotide at any position in the chain, for instance, by introduction of a 5-(3,5-hexadiene)-2'-deoxyuridine nucleoside (See U.S. patent application Ser. No. 08/264,029, filed Jun. 22, 1994, entitled "Novel Method of Preparation of Known and Novel 2'-modified Nucleosides by Intramolecular Nucleophilic Displacement," which is incorporated herein by reference in its entirety). Alternatively, the diene or dienophile moiety can be introduced as a 2'-O-(3,5-hexadiene)-uridine nucleoside. A diene moiety can also be introduced to the oligonucleotide as a diene-bearing non-nucleoside phosphoramidite, such as 3,5-hexadiene-N,N-diisopropyl-2-cyanoethyl phosphoramidite. Reaction of the diene modified oligonucleotide, such as a 5'-terminal 3,5-hexadienephosphate oligonucleotide, with the dienophile modified support, such as maleimide derivatized glass, leads to efficient immobilization of the oligonucleotide.

The method of this invention can be extended to the immobilization of any molecule that can be derivatized with a diene, dienophile or other reactive group capable of undergoing a cycloaddition reaction without limitation. For example, the method can be extended to the immobilization of peptides and proteins with any support capable or being derivatized. A peptide or protein that contains an amino acid building block which has been derivatized with the diene or dienophile, such as O-3.5-hexadiene-tyrosine or serine, or N-maleimidolysine, can be immobilized on any support using the method described herein, without limitation. Natural molecules, such as proteins, can be derivatized with a diene or dienophile bearing a heterobifunctional crosslinking reagent, such as the NHS ester of 3-(4-maleimidophenyl)-propionic acid (Pierce), which allows subsequent conjugation to a support bearing a corresponding diene or dienophile group.

Polyethylene glycol is often conjugated to biomolecules to reduce their immunogenicity and to increase their residence time in vitro. The method of this invention allows immobilization of biomolecules, such as oligonucleotides or peptides, bearing a diene, dienophile or other reactive group capable of undergoing a cycloaddition reaction with another polymer or resin, such as polyethyleneglycol or polystyrene bearing one or several corresponding diene, dienophile or other groups capable of undergoing cycloaddition reactions.

Example 1 (Scheme 1) describes the synthesis of 5-hydroxymethylcyclohexa-1,3-diene (5).

Example 2 (Scheme 2) describes the preparation of NHS reagent (10) from cyclohexadiene alcohol (5).

Example 3 (Scheme 3) describes the synthesis of the diene amidite linker (16) from amino-linker (12). Amino-linker (12) was developed in mimesis of a nucleoside containing a primary (as 5'-OH) and a secondary hydroxyl group (as 3'-OH). This allows the conjugation of the linker on either the 3'- or 5'-end of any oligonucleotide. The attachment of various moieties to the oligonucleotide (e.g., dienes or dyes) is achieved via the linker's amino functionality. Therefore, compound (12) is recognized as a universal linker for conjugation of oligonucleotides.

Example 4 (Scheme 4) describes the synthesis of maleimide-trialkoxy silane (19), which is used to functionalize glass surfaces.

Example 5 describes the synthesis of diene-trialkoxy silane (20) for the functionalization of glass surfaces.

Example 6 describes the synthesis of three 5' functionalized oligonucleotides, compounds (23), (24) and (26). Compounds (23) and (23) (Scheme 6) are functionalized at the 5' end with a diene by reaction with diene-linker amidite (16). Compound (26) (Scheme 7) is functionalized at the 5' end with a maleimide by reaction with maleimidopropionic acid N-hydroxysuccimide ester (compound 18, Scheme 4).

Examples 7 and 8 describe a method for the functionalization of two glass surfaces, specifically glass slides and CPG, with both a diene and a dienophile. Glass surfaces are derivatized with reactive moieties capable of undergoing cycloaddition reactions by deposition of silane monolayers appropriately functionalized for cycloaddition reaction. Specifically, Example 7 describes the functionalization of the two glass surfaces with maleimide dienophile (19) (Scheme 8). Example 7 also describes methods for the detection of the maleimide functionalized surfaces. The maleimide derivatized surfaces are detected by staining with a thiol-fluorescein reagent, which reacts with the maleimide via a Michael-addition as illustrated in Scheme 9. The presence of fluorescein bound to the surfaces is then detected with a Molecular Dynamics' Typhoon Fluorescence Scanner using a green laser to excite the surface-bound fluorescein followed by detection of emission using a 526 nm filter.

Example 8 describes the functionalization of the two glass surfaces with diene (20) (Scheme 10). Example 8 also describes methods for the detection of the functionalized surfaces. The diene derivatized surfaces are detected by Diels-Alder reaction with a fluorescein maleimide as illustrated in Scheme 11.

Example 9 (Scheme 12) describes the Diels-Alder reaction between the 5' diene functionalized oligonucleotide (23) and maleimide functionalized glass slides and microtiter plates. This reaction demonstrates the Diels-Alder surface immobilization of an oligonucleotide (Scheme 12). Detection of the surface-bound oligonucleotide was achieved by its hybridization to a fluorescein-labeled complementary sequence (27) and detection of fluorescence. The results of this Example are set forth in FIG. 8.

Example 10 describes the Diels-Alder reaction between maleimide-CPG and diene derivatized oligonucleotide (24). In Example 9, the conjugation of the diene-oligonucleotide to the maleimide derivatized support was detected by the fluorescence of a labeled complementary sequence after hybridization. This method of detection, however, gives a qualitative result, but does not allow the quantitative determination of surface loading. In Example 10, a different detection method was selected for determination of immobilized oligonucleotide in order to obtain a quantitative determination of surface loading. For purposes of illustration, diene(DMT)-oligonucleotide (24) was used. After Diels-Alder reaction between diene (24) and maleimide, the surface bound amount of oligonucleotide (loading) is calculated after the cleavage of the DMT-group by photometric detection of the DMT-cation as illustrated in Scheme 12.

Figure 9:
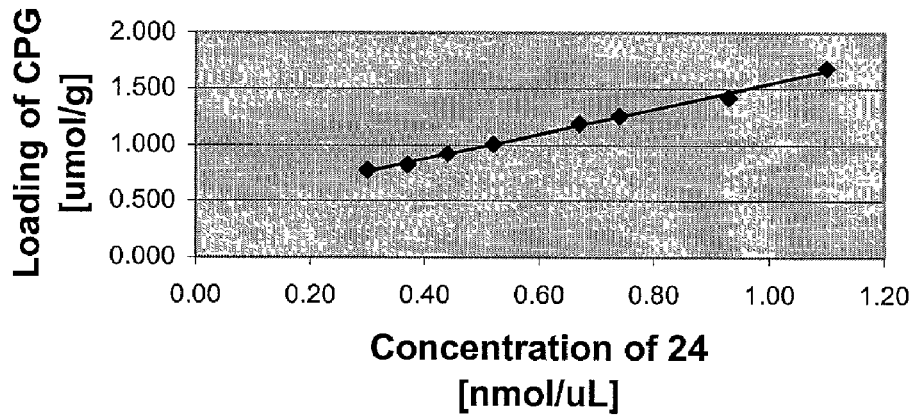
FIG. 9 illustrates graphically the relation between the loading of CPG (10 mg) with oligonucleotide (24) and the concentration of oligonucleotide (24) in solution.

Maleimide-derivatized CPG was incubated with increasing amounts of oligonucleotide (24) in order to demonstrate the relation between oligonucleotide immobilization (as CPG loading) and the amount of diene-oligonucleotide in solution. Using this method the typical range of oligonucleotide loading was calculated to be 0.8-1.7 µmol/g (Table 2, FIG. 9). The results obtained from this experiment also showed that not all maleimide-sites were reacted with diene-oligonucleotide and that the loading can be further increased be treatment with larger amounts of (24) by achieving an exponential dependence instead of a linear curve fit.

Figure 10:
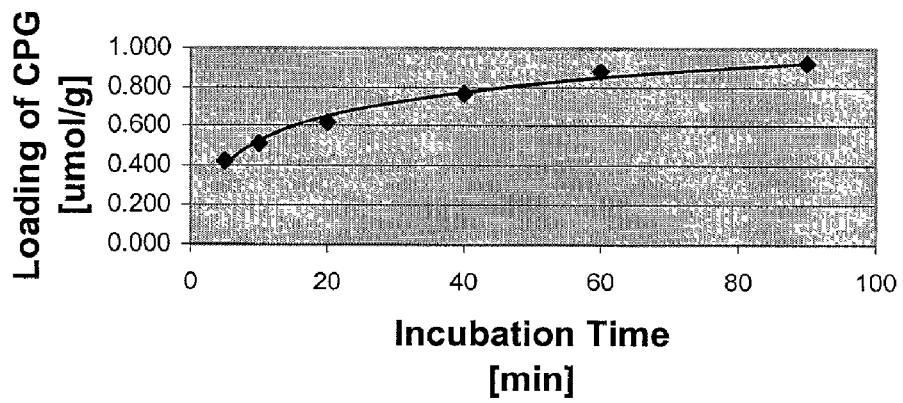
FIG. 10 illustrates graphically the relation between the loading of CPG (10 mg) with oligonucleotide and the incubation time with oligonucleotide (24).

The kinetic relationship between loading and incubation time was also demonstrated. As expected an exponential curve was obtained, but the plateau of the curve was not reached in the time-frame applied for the experiment (Table 3, FIG. 10). After approximately 100 minutes a saturation (by consumption of all oligonucleotide (24) in solution) was achieved. The most interesting result shows that even after an incubation time of 5 minutes, a loading of 0.4 µmol/g was obtained. Compared with the data from the first example, the concentration of 17 applied in this example is too low to saturate all of the maleimide sites of the CPG support.

Example 11 (Scheme 14) describes the conjugation of 5'-maleimide derivatized oligonucleotide (26) to diene coated glass surfaces. The demonstration of conjugation was achieved by hybridization with the labeled complementary sequence (27) and the detection of fluorescence as described above.

Example 12 (Scheme 15) describes the synthesis of diene modified oligonucleotide (29) from NHS reagent (10), the synthesis of which is described in Example 2.

Example 13 (Scheme 16) describes the HPLC monitoring of a Diels-Alder reaction employing a cyclohexadiene derivatized oligonucleotide. To confirm the Diels-Alder reactivity of diene conjugate (29), labeling with commercially available maleimide dienophiles (30) and (31) were carried out. The progress of the reaction was monitored by analytical anion exchange chromatography with samples taken every 5 minutes. Treatment of (29) with N-ethyl maleimide (30) resulted in complete conversion to adduct (32) within 5 minutes, while biotin maleimide 31 required 20 minutes.

Example 14 (Scheme 17) describes the synthesis of diene modified polyethylene glycol substrates (34). Example 14 (Scheme 18) also describes the synthesis of anthracene derivative (36).

Example 15 (Scheme 19) describes the preparation of a dienophile CM5 BIAcore flow cell surface.

Example 16 (Scheme 20) describes a comparison of surface derivatization via PEG-SH (Michael-addition) vs PEG-diene (Diels-Alder surface immobilization).

Example 17 (Scheme 21) describes the Diels-Alder reaction of dienophile derivatized CM5 BIAcore flow cell surface (37) with anthracene derivative (36) (preparation described in Example 14), using the method described in Example 16 to provide compound (38).

Example 18 (Scheme 22) describes the surface immobilization of the cyclohexadiene modified oligonucleotide (29) to the dienophile derivatized CM5 BIAcore flow cell surface (37), followed by hybridization with the complementary oligonucleotide sequence.

Example 19 (Scheme 23) describes the synthesis of anthracene-silane reagent (42).

Example 20 (Scheme 24) illustrates the functionalization of glass slides with anthracene-silane reagent (42).

The following examples are provided to explain and illustrate the present invention and are not to be taken as limiting of the invention.

EXAMPLES

Example 1

Preparation of Cyclic Diene Alcohol (5)

Scheme 1 illustrates the preparation of cyclohexadiene (5). Briefly, the synthesis of diene-alcohol (5) was obtained from alcohol (1) in four steps by a scaleable and very convenient procedure as outlined in Scheme 1. This diene has been synthesized via a different route by Roth et al. ((1993) Chem. Ber. 126:2701-2715).

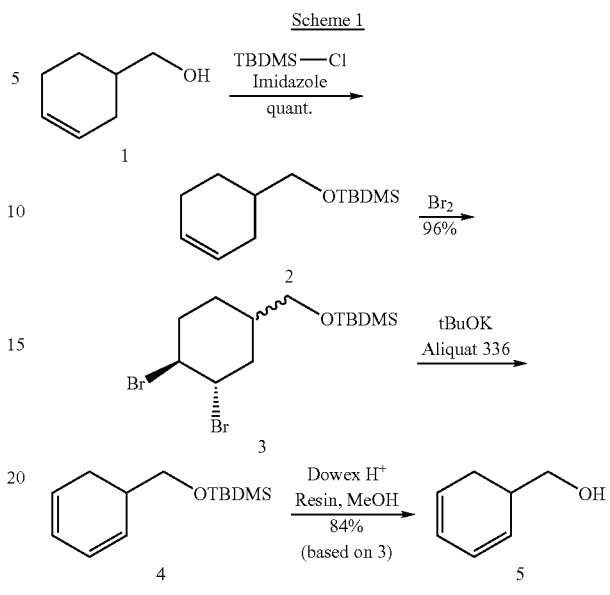

Synthesis of 4-(tert-butyldimethylsilyloxymethyl)-cyclohex-1-ene (2). To a stirred solution of 1,2,3,6-tetrahydrobenzylalcohol (1) (1.12 g, 10 mmol) and imidazole (1.36 g, 20 mmol) in DMF (10 mL) was added TBDMSCl (1.81 g, 12 mmol). After 20 hours, the mixture was treated with brine (100 mL) and the product was extracted with hexanes (3×80 mL). The combined organic layers were washed with brine (100 mL), dried over $MgSO_4$ and evaporated in vacuo to give compound (2) (2.26 g, 100%) as colorless liquid. $R_f$ 0.29 (hexanes). $^1$H NMR ($CDCl_3$) δ 5.65-5.64 (m, 2H), 3.48 (d, J=2.3 Hz, 1H), 3.45 (d, J=2.3 Hz, 1H), 2.08-2.00 (m, 3H), 1.82-1.66 (m, 3H), 1.32-1.19 (m, 1H), 0.89 (s, 9H), 0.04 (s, 6H); $^{13}$C NMR ($CDCl_3$) δ 127.04, 126.23, 67.95, 36.34, 28.23, 25.97, 25.70, 25.33, 24.78, 18.38, −5.32.

Synthesis of trans-1,2-dibromo-3-(tert-butyldimethylsilyloxymethyl)-cyclohexane (3). To a stirred solution of alkene (2) (1.81 g, 8 mmol) in $CCl_4$ (15 mL) was added bromine (0.4 mL, 8 mmol) in $CCl_4$ (1 mL) dropwise. The resulting red mixture was diluted with $CH_2Cl_2$ (50 mL) and washed with 10% $Na_2S_2O_3$ solution (50 mL) and water (50 mL). The organic phase was dried over $Na_2SO_4$ and evaporated in vacuo to give 2.98 g (96%) of compound (3) as a yellow oil. $R_f$ 0.20 (100:1 hexane/EtOAc). $^1$H NMR ($CDCl_3$) δ 4.71-4.64 (m, 2H), 3.47 (d, J=5.3 Hz, 2H), 2.52-2.40 (m, 2H), 2.23-1.52 (m, 5H), 0.89 (s, 9H), 0.04 (s, 6H). $^{13}$C NMR ($CDCl_3$) δ 67.27, 53.60, 53.45, 34.23, 31.41, 28.12, 25.88, 23.25, 18.26, −5.39.

Synthesis of 5-hydroxymethylcyclohexa-1,3-diene (5). To stirred 0° C. solution of dibromide (3) (69.52 g, 0.18 mol) and Aliquat 336 (1.46 g, 3.6 mmol, 0.02 equiv) in THF (500 mL) was added KOtBu (44.89 g, 0.4 mol, 2.2 equiv). Immediate formation of a yellow precipitate occurred and after 5 minutes the cooling bath was removed. After 30 minutes, an aliquot of the mixture was removed and dried under a stream of argon. $^1$H NMR analysis ($C_6D_6$) indicated that only a trace of dibromide (3) was remaining. After an additional 40 minutes, the mixture was evaporated in vacuo, diluted with hexane (300 mL) and washed with a saturated $NH_4Cl$ solution (300 mL). After separation the aqueous layer was extracted with hexane (200 mL) and the combined organic layers were washed with water (300 mL), dried over $MgSO_4$ and evaporated in vacuo to afford 65 g of crude diene (4). This material was dissolved in MeOH (600 mL) and treated with Dowex 50WX4-50 (65 g). The slurry was shaken at 200 rpm for 140 minutes after which time TLC indicated no remaining (4). The resin was filtered and washed with MeOH. The filtrate was evaporated in vacuo and the resulting residue was distilled bulb-to-bulb under reduced pressure to give diene (5) (16.71 g, 84%) as a colorless liquid. Bp 47° C. (2.2 mbar) −50° C. (1.7 mbar); $R_f$ 0.49 (1:1 hexane/EtOAc). $^1$H NMR (CDCl$_3$) δ 5.98-5.62 (m, 4 H), 3.58 (d, J=5.9 Hz, 2 H), 2.56-2.42 (m, 1H), 2.37-2.05 (m, 2 H), 1.50 (s, 1 H). $^{13}$C NMR (CDCl$_3$) δ 126.92, 125.39, 124.98, 123.63, 64.58, 35.47, 24.91.

Example 2

Preparation of NHS Reagent (10)

Scheme 2 illustrates the preparation of NHS reagent (10) from diene (5).

added. After 50 minutes the reaction mixture was diluted with EtOAc (50 mL) and washed with brine (50 mL) and water (2×50 mL). The organic phases were combined, dried over MgSO$_4$ and evaporated in vacuo. Purification via chromatography on the Biotage Flash 40 system eluting with CH$_2$Cl$_2$/MeOH/Et$_3$N (15:1:0.1) afforded 2.62 g (74%) of carbamate (8) as a colorless oil. $R_f$ 0.48 (5:3:1 CHCl$_3$/MeOH/AcOH, 32%). $^1$H NMR (CDCl$_3$) δ 5.94-5.82 (in 2 H), 5.74-5.69 (m, 1 H), 5.64-5.59 (m, 1 H), 5.50 (s, 1 H), 3.96 (d, J=7.0 Hz), 3.63-3.49 (m, 12 H), 3.25 (q, J 6.5, 5.9 Hz, 2 H), 2.76 (t, J=6.7 Hz, 2 H), 2.61-2.49 (m, 1 H), 2.28-2.18 (m, 1 H), 2.13-2.03 (m, 1 H), 1.78-1.65 (m, 4 H); $^{13}$C NMR (CDCl$_3$) δ 156.20, 125.94, 124.68, 123.28, 69.90, 69.50, 68.79, 68.65, 65.25, 38.94, 38.05, 32.50, 32.32, 28.90, 24.55.

Synthesis of 18-N-(5-cyclohexa-1,3-dienemethoxycarbonyl)-18-amino-5-aza-4-keto-9,12,15-trioxa-18-octadecanoic acid (9). To a solution of amine (8) (1.43 g, 4 mmol) and N-methylimidazole (NMI) (0.64 mL, 8 mmol) in pyri-

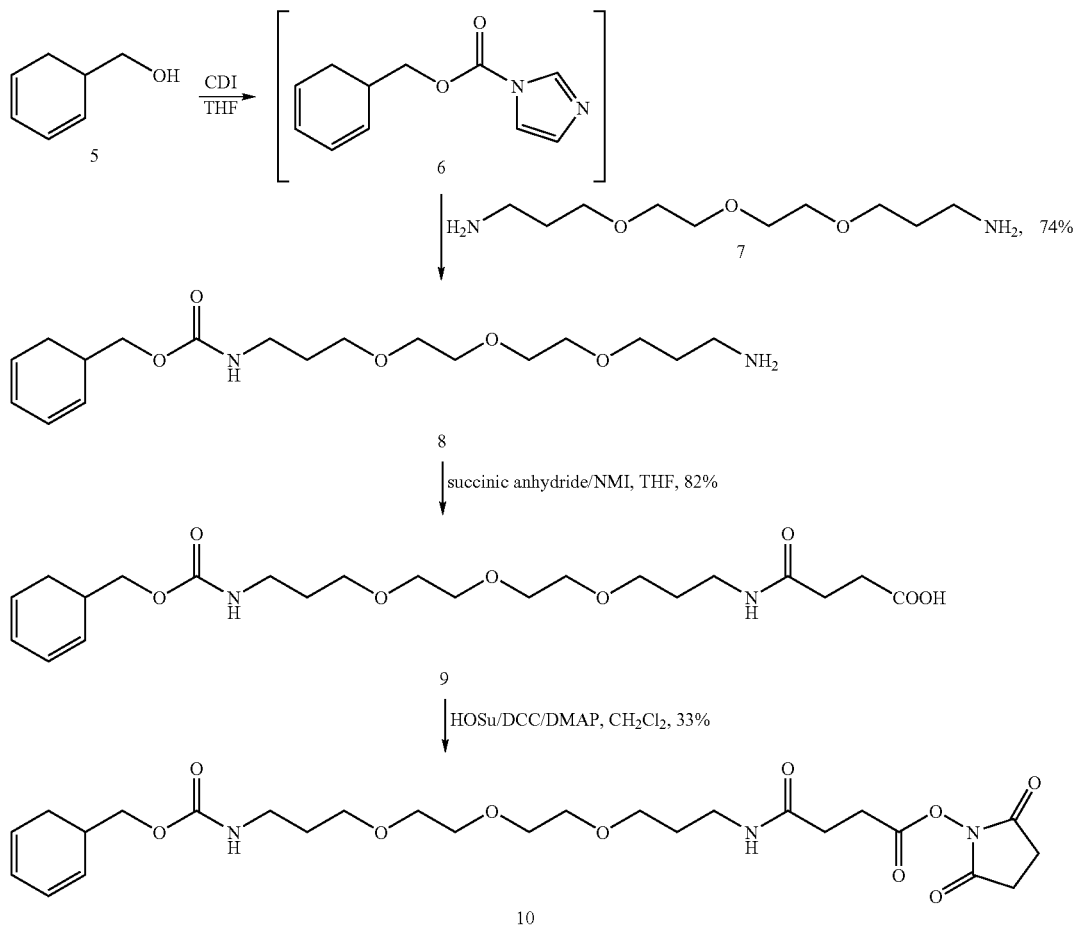

Synthesis of 13-N-(5-cyclohexa-1,3-dienemethoxycarbonyl)-4,7,10-trioxa-1,13-tridecanediamine (8). To a stirred solution of diene (5) (1.10 g, 10 mmol) in THF (20 mL) was added 1,1'-carbonyldiimidazole (CDI) (1.63 g, 10.05 mmol). After 40 minutes, a solution of 4,7,10-trioxa-1,13-tridecanediamine (7) (4.4 mL, 20 mmol) in THF (5 mL) was dine (20 mL) was added succinic anhydride (0.44 g, 4.4 mmol). This mixture was stirred for 2 hours, evaporated in vacuo and the residue was purified by silica gel chromatography on the Biotage Flash 40 system eluting with CH$_2$Cl$_2$/MeOH/Et$_3$N (10:1:0.1). To remove Et$_3$N, the product was dissolved in MeOH (20 mL) and treated with Dowex MWC-1

(2 g) for 1 hour. The solids were filtered and the filtrate was evaporated in vacuo to yield 1.50 g (82%) of acid (9) as slightly yellow oil. R$_f$0.64 (5:3:1 CHCl$_3$/MeOH/AcOH, 32%), 0.12 (10:1:0.1 CHCl$_3$/MeOH/Et$_3$N). $^1$H NMR (CDCl$_3$) δ 7.15-6.98 (m, 1 H), 5.97-5.82 (m, 2 H), 5.77-5.69 (m, 1 H), 5.65-5.60 (m, 1 H), 5.37-5.28 (m, 1 H), 3.98 (d, J=7.0 Hz, 2 H), 3.64-3.46 (m, 12 H), 3.31 (q, J=6.5, 5.9 Hz), 3.26 (q, J=6.5, 5.9 Hz), 2.61-2.51 (m, 3 H), 2.46 (t, J=6.2 Hz, 2 H), 2.33-2.20 (m, 1 H), 2.18-2.02 (m, 1 H), 1.79-1.71 (m, 4 H). $^{13}$C NMR (CDCl$_3$) δ 175.46, 172.40, 156.69, 126.32, 125.21, 123.79, 70.29, 70.24, 69.86, 69.65, 69.23, 66.01, 38.71, 37.80, 32.74, 30.89, 30.12, 29.32, 28.61, 25.02.

Synthesis of 18-N-(5-cyclohexa-1,3-dienemethoxycarbonyl)-18-amino-5-aza-4-keto-9,12,15-trioxa-18-octadecanoic acid N-hydroxysuccinimide ester (10). To a stirred 0° C. solution of acid (9) (913 mg, 2 mmol), N-hydroxysuccinimide (230 mg, 2 mmol) and DMAP (12 mg, 0.1 mmol) in CH$_2$Cl$_2$ (10 mL) was added dicyclohexylcarbodiimide (433 mg, 2.1 mmol). After 5 minutes the cooling bath was removed. After 2 hours, TLC indicated incomplete conversion and additional N-hydroxysuccinimide (46 mg, 0.4 mmol) and dicyclohexylcarbodiimide (83 mg, 0.4 mmol) were added. After 22 hours, TLC analysis still indicated incomplete conversion and more N-hydroxysuccinimide (46 mg, 0.4 mmol) and dicyclohexylcarbodiimide (83 mg, 0.4 mmol) were added. After 3 hours, the mixture was filtered through Celite and the precipitate was washed with CH$_2$Cl$_2$ (10 mL). The filtrate was evaporated in vacuo and the residue was dissolved in EtOAc (5 mL), again filtered and evaporated in vacuo. Flash chromatographic purification employing the Biotage Flash 40 system eluting with a gradient of hexane/acetone 1:1→1:0.8→1:0.6 afforded 370 mg (33%) of NHS-ester (10) as a colorless oil. R$_f$0.45 (10:1:0.2 CHCl$_3$/MeOH/AcOH), 0.32 (1:2 hexane/acetone). $^1$H NMR (CDCl$_3$) δ 6.69, 6.52 (2s 1 H), 5.91-5.82 (m, 2 H), 5.73-5.69 (m, 1 H), 5.63-5.59 (m, 1 H), 5.25 (s, 1 H), 3.95 (d, J=6.5 Hz, 1 H), 3.60-3.48 (m, 12 H), 3.34-3.30 (m, 2 H), 3.23-3.20 (m, 1 H), 2.97-2.90 (m, 2 H), 2.79 (s, 4 H), 2.73-2.50 (m, 3 H), 2.32-2.02 (m, 2 H), 1.75-1.71 (m, 4 H). $^{13}$C NMR (CDCl$_3$) δ 169.63, 168.94, 168.08, 156.47, 126.31, 125.16, 125.11, 123.70, 70.23, 70.20, 69.70, 69.77, 69.22, 65.85, 38.73, 37.92, 32.70, 30.25, 29.26, 28.53, 26.54, 25.36, 24.94.

Example 3

Synthesis of Diene Phosphoramidite (16)

The synthesis of the diene-phosphoramidite (16), which is suitable for the attachment to the 5'-end of an oligonucleotide, is outlined in Scheme 3. Briefly, starting from the commercially available and enantiomerically pure alcohol (11) the universal linker (12) was obtained by LiAlH$_4$ reduction. The crude amine was acylated with diene-carbamate (6), generated in situ by the reaction of diene (5) with carbonydiimidazole (CDI) as described in Example 1. The crude product, diol (13) was then acetylated to enable purification by flash-chromatography. After purification, the acetates were cleaved and the crude diol was selectively tritylated with 4,4'-dimethoxytrityl chloride (DMT) to give the alcohol (15). Alcohol (15) was then reacted with 2-cyanoethyl-bis-(N,N-diisopropylamino)-phosphoramidite and 4,5-dicyanoimidazole (DCI) to produce amidite (16), which was then purified by flash-chromatography.

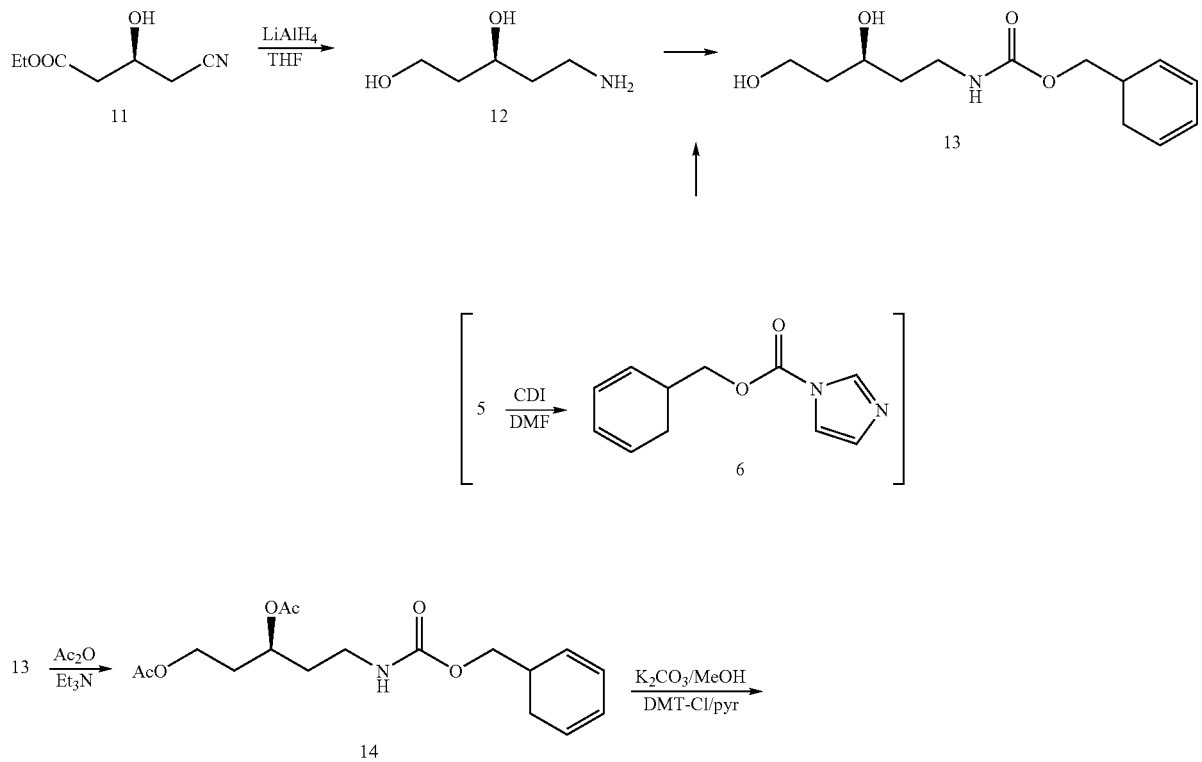

-continued

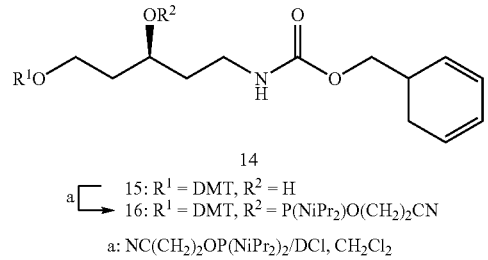

14
a ⎡ 15: R¹ = DMT, R² = H
  ⎣→ 16: R¹ = DMT, R² = P(NiPr₂)O(CH₂)₂CN a: NC(CH₂)₂OP(NiPr₂)₂/DCI, CH₂Cl₂

Synthesis of (S)-5-amino-pentane-1,3-diol (12). LiAlH₄ (26.5 g, 0.70 mol) was suspended in anhydrous THF (250 mL) and cooled to 0° C. Alcohol (11) (20.0 g, 0.13 mol), dissolved in anhydrous THF (100 mL), was added dropwise. The mixture was warmed to room temperature and stirred overnight. After cooling to 0° C., the mixture was treated sequentially with H₂O (12.6 mL, 0.70 mol), 10 N NaOH (34.9 mL, 0.35 mol) and H₂O (37.8 mL, 2.10 mol). The resulting solids were removed by filtration and the filtrate was concentrated in vacuo. The material recovered (12.7 g, 84%) was consistent with the desired amine-diol (12).

Synthesis of (S)-O-cyclohexa-2,4-dienylmethyl-N-(3,5-diacetoxypentyl)-carbamate (14). Diene-carbamate (6) was generated in situ by addition of CDI (3.5 g, 21.6 mmol) to a solution of diene-alcohol (5) (2.0 g, 18.2 mmol) in DMF (17 mL). After stirring for 2 hours the crude amine (12) (2.0 g, 16.8 mmol) was added and stirring was continued overnight. The mixture was concentrated in vacuo and the residue dissolved in CH₂Cl₂ (55 mL). After addition of Et₃N (23.4 mL, 168 mmol), the mixture was cooled to 0° C. and treated with Ac₂O (15.9 mL, 168 mmol). The solution was allowed to warm to room temperature and stirring was continued overnight. The reaction mixture was washed with a saturated NaHCO₃ solution (50 mL) and brine (50 mL), dried over Mg₂SO₄ and concentrated in vacuo. The crude product was then purified by flash chromatography (Biotage Flash 40 system) on silica gel, eluting with EtOAc/CH₂Cl₂ (1:4 v/v) to yield 1.9 g (33%) of carbamate (14) as a colorless oil: $R_f$ 0.24 (EtOAc/CH₂Cl₂ 1:4 v/v). ¹H NMR (300 MHz, CDCl₃) δ 5.97-5.62 (m, 4H), 5.10-5.00 (m, 2H), 4.12-3.97 (m, 4H), 3.40-3.34 (m, 2H), 3.02-2.94 (m, 2H), 2.67-2.58 (m, 2H), 2.67-2.58 (m, 1H), 2.30-1.64 (m, 8H).

ES-MS (pos): [M+H]⁺ 340 (339.2 calcd).

Synthesis of (S)-O-cyclohexa-2,4-dienylmethyl-N-[5-(4,4'-dimethoxtityl)-3-hydroxypentyl]-carbamate (15). Diacetate (14) (1.9 g, 5.6 mmol) was dissolved in MeOH (30 mL) and K₂CO₃ (39 mg, 0.3 mmol) was added. After 2 hours, the mixture was concentrated in vacuo and the residue was dried by azeotropic distillation with pyridine (2×20 mL). The crude diol was dissolved in pyridine (37 mL) and treated with 4,4'-dimethoxytrityl chloride (3.77 g, 11.1 mmol). The reaction was stirred overnight and then concentrated to a residue. The reddish oil was dissolved in EtOAc (50 mL) and washed sequentially with a saturated NaHCO₃ solution (50 mL) and brine (50 mL). The organic phase was dried over MgSO₄, filtered and concentrated in vacuo. The crude residue was purified by flash chromatography (Biotage Flash 40 system) on silica gel, eluting with EtOAc/CH₂Cl₂ (1:9 v/v) to yield 1.0 g (32%) of alcohol (15) as a slightly yellow oil. $R_f$ 0.21 (EtOAc/CH₂Cl₂ 1:9 v/v). ¹H NMR (300 MHz, CDCl₃) δ 7.42-7.15 (m, 8H), 6.85-6.82 (m, 4H), 5.97-5.85 (m, 2H), 5.77-5.62 (m, 2H), 5.20 (m, 1H), 4.04-3.99 (m, 2H), 3.86-3.80 (m, 8H), 3.51-3.35 (m, 3H), 3.19-2.26 (m, 2H), 2.63 (m, 1H), 2.26-2.04 (m, 2H), 1.85-1.53 (m, 4H).

Synthesis of (S)-O-cyclohexa-2,4-dienylmethyl-N-{3-[(2-cyanoethoxy)-diisopropylaminophosphano]-5-(4,4'-dimethoxytrityl}-3-hydroxpentyl]-carbamate (16). A solution of alcohol (15) (1.00 g, 1.8 mmol) in anhydrous CH₂Cl₂ (18 mL) was treated with 2-cyanoethyl-bis-(N,N-diisopropylamino)-phosphoramidite (0.60 g, 2.0 mmol), followed by 4,5-dicyanoimidazole (0.11 g, 0.9 mmol). After stirring for 1 hour, TLC analysis indicated complete conversion of (15). The mixture was diluted with CH₂Cl₂ (30 mL), washed with a saturated NaHCO₃ solution (30 mL) and brine (30 mL), dried over Mg₂SO₄ and concentrated in vacuo. The crude residue was purified by flash chromatography (Biotage Flash 40 system) on silica gel, eluting with EtOAc/CH₂Cl₂ (1:9 v/v) to afford 933 mg (68%) of amidite (16) as a colorless foam. $R_f$ 0.40 (EtOAc/CH₂Cl₂ 1:9 v/v). ¹H NMR (300 MHz, CDCl₃) δ 7.43-7.17 (m, 8H), 6.84-6.79 (m, 4H), 5.97-5.85 (m, 2H), 5.77-5.62 (m, 2H), 5.48 (m, 1H), 4.06-3.97 (m, 3H), 3.85-3.45 (m, 10H), 3.30-3.12 (m, 4H), 2.68-2.61 (m, 3H), 2.46-2.42 (m, 1H), 2.23-1.59 (m, 8H), 1.16-1.02 (m, 12H). ³¹P NMR (121 MHz, CDCl₃) 149.08, 148.38. ES-MS (pos): [M+H³O]⁺ 776 (776.4 calcd).

Example 4

Synthesis of a Maleimide-Silane Reagent

Scheme 4 illustrates the synthesis of a maleimide-silane reagent for the functionalization of glass surfaces. Briefly, with reference to Scheme 4, propylaminosilane (17) was reacted with the functionalized maleimide N-hydroxysuccinimide-ester (18), to provide after aqueous work-up maleimide-silane (19), which was used as a crude product for derivatization of glass surfaces.

Scheme 4

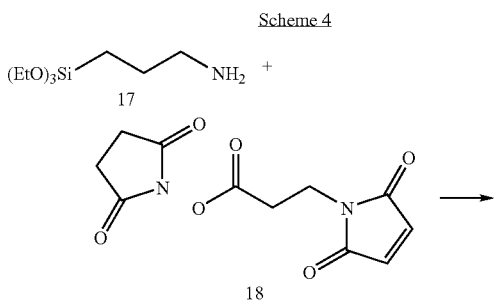

-continued

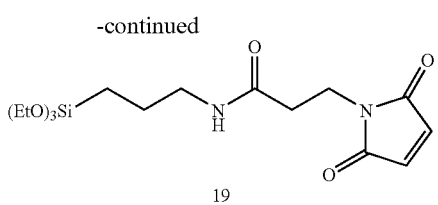

19

Synthesis of 3-maleimido-N-(3-triethoxysilanylpropyl)-propionamide (19). 3-Maleimidopropionic acid N-hydroxysuccinimide ester (18) (4.0 g, 15.03 mmol, 1.0 equiv.) was dissolved in N,N-dimethylformamide (75 mL) and 3-aminopropyltriethoxysilane (17) (5.06 mL, 15.03 mmol, 1 equiv.) was added and the reaction mixture was allowed to stir for 22 hours. An aliquot (0.15 mL) was removed by syringe, concentrated in vacuo, and the resulting oil was analyzed by $^1$H NMR spectroscopy. The oil was consistent with desired product. The reaction mixture was then concentrated in vacuo at 50-55° C. and the residue obtained was dissolved in $CH_2Cl_2$ (75 mL), washed with water (3×50 mL) and brine (50 mL), filtered through granular $Na_2SO_4$, and concentrated under reduced pressure in vacuo to provide 6.65 g (>100% due to residual N,N-dimethylformamide) of the crude maleimide-silane (19) as a light yellow oil. Crude (19) was used without purification. $^1$H NMR (300 MHz, $CDCl_3$) δ 6.65 (s, 2H), 6.00 (s, 1H), 3.77 (q, J=7 Hz, 6H), 3.70 (m, 2H), 3.17 (m, 2H), 2.46 (m, 2H), 1.56 (m, 2H), 1.18 (t, J=7 Hz, 9H), 0.57 (m, 2H). $^{13}$C NMR (75 MHz, $CDCl_3$) δ 170.36, 169.28, 134.09, 58.35, 41.77, 34.56, 34.21, 23.20, 18.20, 7.65. FB-MS (pos): [M+H]$^+$ 373 (373.2 calcd).

Example 5

Synthesis of a Diene-Silane Reagent

Scheme 5 illustrates the synthesis of a diene-silane reagent for the functionalization of glass surfaces. Briefly, with reference to Scheme 5, analogous to the synthesis of linker (13), diene (5) was treated with carbonyldiimidazole. To the imidazolate formed in situ was added amine (17). After stirring overnight the product of the reaction mixture, diene-silane (20) was separated and used as a crude product for glass surface functionalizations.

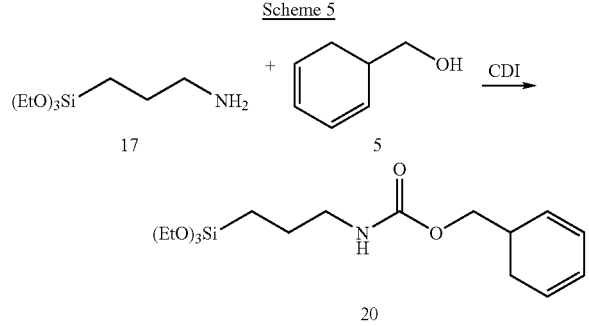

Synthesis of O-cyclohexa-2,4-dienylmethyl-N-(3-triethoxysilanylpropyl)-carbamate (20). Diene alcohol (5) (0.50 g, 4.54 mmol, 1.0 equiv.) was dissolved in N,N-dimethylformamide (15 mL), carbonyldiimidazole (0.77 g, 4.77 mmol, 1.05 equiv.) was added and the mixture was allowed to stir for 4 hours. The formation of the imidazolate intermediate (6) (Scheme 2) was confirmed by $^1$H NMR spectroscopic analysis of an aliquot (0.3 mL) of the reaction mixture that was concentrated in vacuo to an oil. The oil was consistent with desired intermediate by $^1$H NMR spectroscopy as evidenced by the chemical shift in the resonance of the methylene protons from 3.6 ppm to 4.3 ppm. 3-Aminopropyltriethoxy silane (17) (1.51 mL, 4.50 mmol, 1.0 equiv.) was then added and the reaction mixture was stirred for 12 hours. The formation of the desired product (20) was confirmed by $^1$H NMR spectroscopic analysis of an aliquot (0.3 mL) of the reaction mixture that was concentrated in vacuo to an oil. The oil was consistent with desired product as evidenced by the chemical shift in the resonance of the methylene protons from 4.3 ppm to 4.0 ppm. The reaction mixture was concentrated at reduced pressure, in vacuo overnight and imidazole crystallized out of the resulting brown oil. The oil obtained was separated from the crystals by pipette and transferred to a clean round-bottom flask to provide 1.5 g (93%) of the desired diene-silane (20) as a brown oil. Crude (20) was used without further purification. $^1$H NMR (300 MHz, $CDCl_3$) δ 5.98-5.63 (m, 4H), 4.95 (s, 1H), 4.00 (m, 2H), 3.82 (q, J=7 Hz, 6H), 3.16 (m, 2H), 2.62 (m, 1H), 2.16 (m, 2H), 1.62 (m, 2H), 1.23 (t, J=7 Hz, 9H), 0.64 (m, 2H). $^{13}$C NMR (75 MHz, $CDCl_3$) δ 158.67, 135.41, 126.70, 125.59, 124.14, 66.39, 58.66, 43.16, 33.15, 25.42, 23.85, 18.52, 7.81. FB-MS (pos): [M+H]$^+$ 358 (358.2 calcd).

Example 6

Synthesis of Labeled Oligonucleotides

The synthesis of various labeled and unlabeled (for control experiments) oligonucleotides is illustrated in Schemes 6 and 7 below. All syntheses were carried out employing standard procedures for solid phase oligonucleotide synthesis using phosphoramidite building blocks and a CPG solid support. The 20 mer (22) (SEQ ID NO:1) was chosen for purposes of illustration. With reference to Scheme 6, DNA oligonucleotide (22) was synthesized on CPG performing the standard protocol to give the CPG bound oligonucleotide (21). An aliquot of (21) was deprotected and cleaved from the CPG support, to provide the crude control oligonucleotide (22). The diene labeled oligonucleotide (23) was synthesized by prolongation of the 5'-end of (21) with the diene-linker amidite (16). After further processing and detritylation/cleavage the crude oligonucleotide was subjected to AX-HPLC to yield 86% of pure (23).

In a second experiment, the diene-functionalized CPG bound oligonucleotide obtained from step c was divided into two portions. One portion was cleaved and deprotected without detritylation to give crude diene(DMT)-oligonucleotide (24) (Scheme 6) and the second portion was processed as described above, but without purification to give crude diene-oligonucleotide (23).

Scheme 6

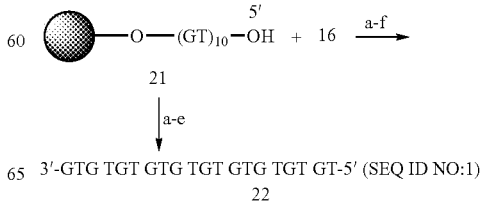

3'-GTG TGT GTG TGT GTG TGT GT-5' (SEQ ID NO:1)
22

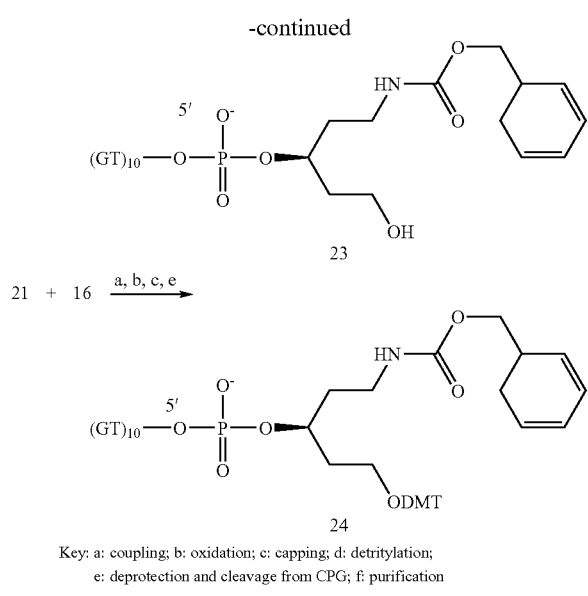

Key: a: coupling; b: oxidation; c: capping; d: detritylation;
e: deprotection and cleavage from CPG; f: purification In order to perform the Diels-Alder cycloaddition in the reverse direction a maleimide functionalized oligonucleotide was synthesized as illustrated in Scheme 7. With reference to Scheme 7, the standard sequence was synthesized on a CPG support and extended with a protected amino-linker. Following deprotection and cleavage from the CPG support the 5'-aminohexyloligonucleotide product (25) was acylated with the maleimide NHS-ester (18). Following filtration through Sephadex the crude maleimide-oligonucleotide (26) was obtained.

In order to allow fluorescence detection of the immobilized oligonucleotide by hybridization with a dye-labeled complementary sequence the 20 mer 5'-fluorescein-CACACACA-CACACACACACA-3' (27) (SEQ ID NO:2) was synthesized on a CPG support employing the standard protocol.

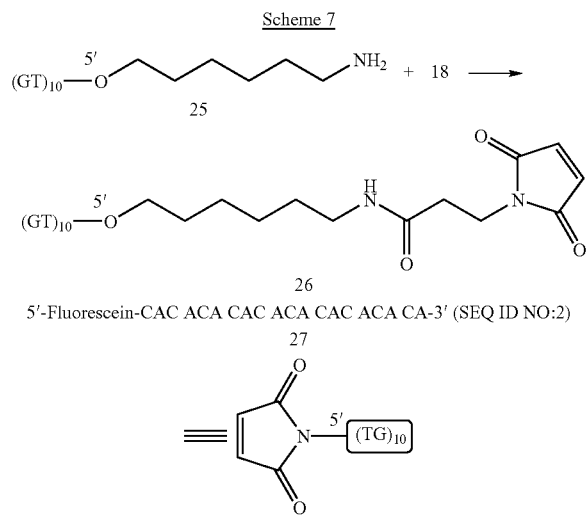

Scheme 7

Synthesis of 5'-TGTGTGTGTGTGTGTGTGTG-3' (22) (SEQ ID NO:1). The synthesis of oligonucleotide (22) was accomplished by the standard phosphoramidite method on a 8800 DNA/RNA synthesizer (Millipore) at 160 μmol scale. After the final detritylation and subsequent washing, an aliquot of CPG bound oligonucleotide (21) was removed, dried and deprotected by 27% aqueous $NH_4OH$ for 15 hours at 55° C. Anion exchange HPLC analysis demonstrated a purity of 78% (at 260 nm) of crude oligonucleotide (22).

Synthesis 5'-diene-oligonucleotide (23). Synthesis of compound (23) was performed on a Millipore 8800 synthesizer in a fluidized bed conformation. The CPG bound oligonucleotide (21) (160 μmol) as described above was treated with amidite (16) (0.2 M in $CH_3CN$, 2.5 equiv.) and 4,5-dicyanoimidazole (1.0 M in $CH_3CN$, 16 equiv.) for 10 minutes followed by a second amidite (16) addition (0.2 M in $CH_3CN$, 1.5 equiv.) together with 4,5-dicyanoimidazole (1.0 M in $CH_3CN$, 16 equiv.) for 10 minutes. The support bound oligonucleotide was oxidized with 12 in the presence of pyridine under standard conditions and detritylated by treatment with 10% dichloroacetic acid in $CH_2Cl_2$. Cleavage from the support and base deprotection was performed with 27% aqueous $NH_4OH$ for 2 hours at 70° C. The deprotection solutions were then cooled to 4° C. before the CPG was filtered and washed with DI water to recover the crude oligonucleotide product, compound (23).

An aliquot of the crude oligonucleotide product (800 μL) was loaded onto a DNAPac PA-100 4×250 mm anion exchange column at a concentration of 10.6 mg/mL. The product was eluted with a linear elution gradient employing a two-buffer system, where buffer A is 25 mM Trizma/1 mM EDTA (Trizma-EDTA) with 10% $CH_3CN$ and buffer B is Trizma-EDTA with 10% $CH_3CN$ and 1 M NaCl. A temperature of 80° C. was maintained throughout the purification. Appropriate purification fractions were consolidated and desalted on a Nap25 column. After desalting the oligonucleotide (23) (designated as "23, pure") was provided in deionized-water at a concentration of 1.1 OD/mL (86% purity by anion exchange HPLC). MALDI-MS: $M^+$ 6585.47 (6585.1 calcd).

In a second synthesis of oligonucleotide (23), CPG bound oligonucleotide (21) (25 μmol) was treated with amidite (16) (0.2 M in $CH_3CN$, 15 equiv.) and 4,5-dicyanoimidazole (1.0 M in $CH_3CN$, 16 equiv.) for 20 minutes. After oxidation and capping the CPG bound oligonucleotide was partitioned into two aliquots. The first aliquot (0.25 g, 6 μmol) was subjected to cleavage from the support and base deprotection to give 17 mg, (450 OD) of crude (purity 60% by anion exchange HPLC) diene (DMT)-oligonucleotide (24) after drying. The second aliquot (0.80 g, 19 μmol) was detritylated prior to cleavage from the support and base deprotection to give 89 mg (2400 OD) of crude (61% purity by anion exchange HPLC purity) oligonucleotide (23) (designated as "23, crude").

Synthesis of 5'-[N-(3-maleimidopropionyl)-6-aminohexyl]-TGTGTGTGTGTGTGTGTG TG-3' DNA oligonucleotide (26). 2-Cyanoethyl-N,N'-diisopropyl-6-(4-methoxytrityl-amino)-hexylphosphoramidite* (0.2 M in $CH_3CN$, 10 equiv. each. Proligo Biochemie GmbH, Hamburg, Germany. Prod. # M010282) was coupled to CPG bound oligonucleotide (21) (32 μmole) in the presence of 4,5-dicyanomidazole activator (1.0 M in $CH_3CN$, 16 equiv.) for 20 minutes. Standard oxidation and capping preceded the final monomethoxytrityl removal with 10% dichloroacetic acid in $CH_2Cl_2$. Cleavage and deprotection of the oligonucleotide from the support in 27% aqueous $NH_4OH$ and consequential drying provided 155 mg (4200 OD) of crude amino-oligonucleotide (25) (55% purity by anion exchange HPLC).

Amino-oligonucleotide (25) (2.6 μmol) was resuspended in DMF (2 mL). To this solution maleimide NHS-ester (18) (35 mg, 130 μmol, 50 equiv.) was added and the reaction was stirred at room temperature overnight then placed in speed vacuum to remove the solvent. The dried pellet was then resuspended in H$_2$O (1.5 mL) and loaded onto four 1 mL G-25 spin columns to remove un-reacted (18) and side products from the product of the reaction maleimide-oligonucleotide (26).

Detection of Maleimide by Fluorescence.

Maleimide-oligonucleotide (26) (15 mmol, ca. 500 OD) was reacted with deprotected 5-((2-and-3)-S-(acetylmercapto)succinoyl)amino)fluorescein) (SAMSA fluorescein reagent). SAMSA fluorescein reagent was deprotected by addition of 0.1 M NaOH (50 µL) to the protected SAMSA fluorescein reagent (500 µg) and subsequent reaction at room temperature for 15 minutes followed by neutralization with 6 N HCl (0.7 µL) buffered with 0.5 M Na$_2$HPO$_4$-buffer (10 µL, pH=7.0). The entire deprotected SAMSA-fluorescein was added to compound (26) (20 µL, 15 nmols) and incubated for 30 minutes at room temperature. Unreacted SAMSA-fluorescein was removed by loading of the reaction mixture on a 1 mL G-25 spin column, preequilibrated with phosphate-buffed saline. The product, fluorescein stained (26) (1,2 and 3 µL) was loaded on a 15% polyacrylamide Tris borate EDTA (TBE) gel and scanned with the Typhoon Molecular Dynamics' Scanner for detection. Surface bound fluorescein was excited with a green laser followed by emission detection with a 526 nm filter (SP fluorescein filter). The photomultiplier tube settings were 600 V, sensitivity set to normal and the focal plane was set at the surface. The results are set forth in FIG. 1. The presence of a fluorescent signal demonstrates that (25) was successfully reacted with reagent (18) to create the maleimide-oligonucleotide (26).

Synthesis of 5'-fluorescein-CACACACACACACACA-CACA-3' DNA oligonucleotide (27) (SEQ ID NO:2). Two separate 1 µmole syntheses were performed on an Expedite DNA/RNA synthesizer using the standard phosphoramidite protocol. 5' Fluorescein-phosphoramidite (0.1 M in CH$_3$CN, 11.2 equiv., available from Glen Research, VA, USA. Prod. #10 5901) was coupled to the CPG-bound 20 mer in the presence of tetrazole (0.25 M in CH$_3$CN, 102 equiv.) for 5 minutes. Deprotection in 27% aqueous NH$_4$OH resulted in approximately 300 OD of crude product for anion exchange HPLC purification. Purification utilizing a buffer system of 20 mM NaClO$_4$ with 20 mM NaOAc and 10 vol-% CH$_3$CN (buffer A) and 600 mM NaClO$_4$ with 20 mM NaOAc and 10% vol CH$_3$CN (buffer B), resulted in 75.7 OD of oligonucleotide product (27) from synthesis #1 (96.6% purity by anion exchange HPLC) and 79.3 OD of oligonucleotide product (27) from synthesis #2 (80% purity by anion exchange HPLC). Both oligonucleotides were desalted on Nap 10 columns and finally evaporated in a speedvac vacuum concentrator.

Example 7

Functionalization of Glass Surfaces with Maleimide

Scheme 8 illustrates the reaction of either glass slides or CPG with the maleimide-silane 19. The maleimide functionality is introduced onto the glass slides and CPG by condensation of maleimide-silane (19) with the glass surfaces.

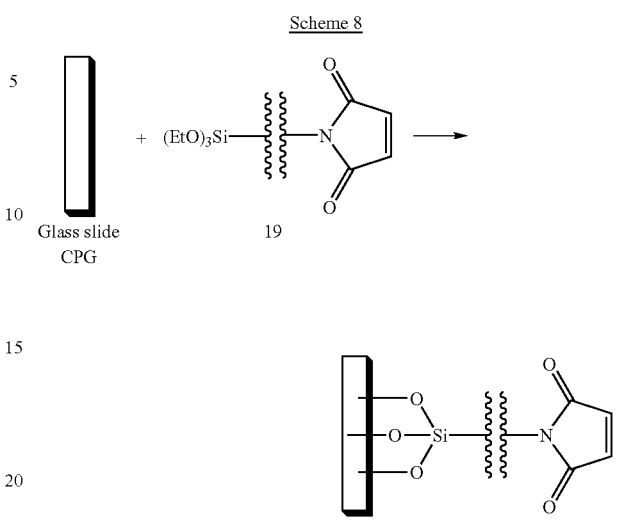

The method used to detect maleimide functionalization of the glass surfaces involves staining the glass surface with a thiol-containing fluorescein reagent, which reacts with the surface-bound maleimide via a Michael-addition reaction, as illustrated in Scheme 9. The presence of fluorescein bound to the surfaces can then be detected with a Molecular Dynamics' Tyhpoon fluorescence Scanner using a green laser to excite the surface-bound fluorescein followed by detection of emission using a 526 nm filter.

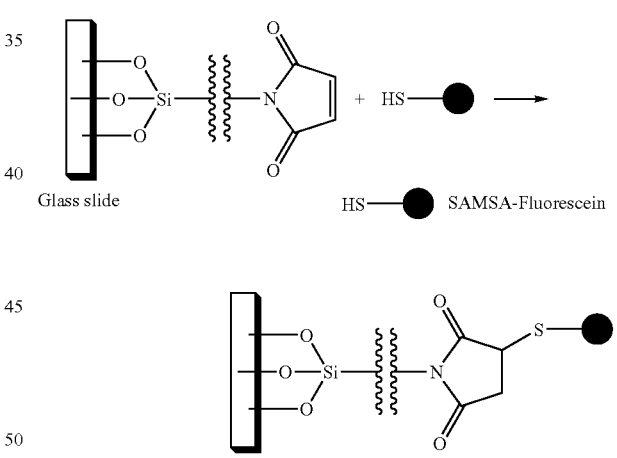

Pre-treatment of glass micro slides. Procedure #1: Glass micro slides (Corning no. 2947, description: plain, pre-cleaned, 3 inch×1 inch×1 millimeter) were soaked in 2 N NaOH for 2 hours at ambient temperature, washed with water, soaked in boiling 2 N HCl for 1 hour, washed with water and methanol, and then dried under reduced pressure in a high vacuum oven at 100° C. for 2 hours. The slides were then allowed to cool in a vacuum desiccator until use. Procedure #2: Micro slides were soaked in 2 N HCl at ambient temperature for 2 hours then in boiling 2 N HCl for 1 hour, washed with water and methanol, and then dried under reduced pressure in a high vacuum oven at 100° C. for 2 hours. The slides were then allowed to cool in a vacuum desiccator until use.

Maleimide functionalization of glass slides. The micro slides (2 pre-treated according to procedure #1 and 2 pre-treated according to procedure #2) were placed upright into a slide chamber containing a 1% (v/v) solution of the maleimide-silane reagent (19) in toluene (25 mL). The amount of solution used was sufficient to soak only the lower half (approximately 1.5 inches) of each slide. After 16 hours, one of the slides (pre-treated according to procedure #1) was removed from the chamber and washed sequentially with toluene, methanol, methanol/water (1:1, v/v), water, methanol/water (1:1, v/v), methanol and ethyl acetate (both sides of the slide were washed with 3×2 mL of each solvent by pipette). The slide was then allowed to air dry.

Detection of surface-maleimide by fluorescence. The slide was assayed for maleimide functionalization using a thiol-containing fluorescein reagent, 5-((2-(and-3)-S-(acetylmercapto)succinoyl)amino)fluorescein (SAMSA fluorescein, Molecular Probes). One side of the slide was completely covered with an activated solution of SAMSA fluorescein (prepared from 10 mg in 1 mL of 0.1 M NaOH, 14 μL of 6 M HCl, 0.2 mL of 0.5 M sodiumphosphate buffer, pH=7) and incubated at ambient temperature for 30 minutes. The slide was then soaked in 0.5 M sodium phosphate buffer, pH 7, for 30 minutes with agitation and blotted dry with a fine paper tissue. The slide was then placed on the surface of a Molecular Dynamics' Typhoon fluorescence scanner. Surface bound fluorescein was excited with a green laser followed by emission detection with a 526 nm filter (SP fluorescein filter). The photomultiplier tube settings were 600 V, sensitivity set to normal and the focal plane was set at the surface.

Figure 2:
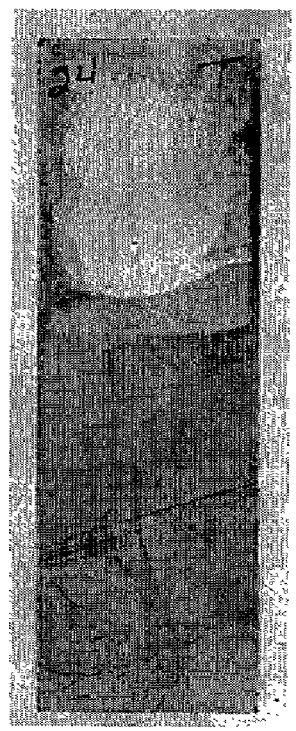
FIG. 2 is a fluorescence scan of a glass slide showing maleimide functionalization on the lower half of the slide, that was treated with maleimide-silane (19), followed by reaction with a thiol containing-fluorescein reagent (SAMSA-reagent), as described in Example 7.

The slide showed a strong response consistent with maleimide functionality primarily on the lower half of the slide (FIG. 2). The distinct line and intense response at and below the halfway mark on the slide show that the maleimide functionalization of the glass slide was successful. The slide also showed a weak response consistent with maleimide functionality on the edges of the slide, possibly due to the contact with the sides of the chamber, and slightly above the halfway mark where the slide may have come in contact with the solution during addition or removal of the slide from the chamber. After 19 hours in the solution of toluene containing maleimide-silane reagent (19), the remaining slides were washed as described above and then treated with a 5 vol-% solution of chlorotrimethylsilane in pyridine/THF (1:9, v/v) for 5 minutes to cap free silanol groups. The slides were then washed with THF, methanol and ethyl acetate (both sides of the slide were washed with 3×2 mL of each solvent by pipette), allowed to air dry and were stored in the vacuum desiccator until use.

Pre-treatment of native CPG-500. Native CPG-500 was stirred in boiling 2 N HCl for 2 hours, then collected on a glass-fritted funnel, washed with water and methanol, and dried under reduced pressure in a high vacuum oven at 100° C. for 2 hours. The CPG was then allowed to cool in a vacuum desiccator until use.

Maleimide functionalization of CPG. CPG (0.75 g, pre-treated according to the procedure described above) was stirred in a 1 vol-% solution of the maleimide-silane reagent (19) in toluene (25 mL) for 51 hours. The CPG was then collected on a glass-fritted funnel and washed sequentially with toluene, methanol, methanol/water (1:1, v/v), water, methanol/water (1:1, v/v), methanol and ethyl acetate (3×10 mL of each solvent). The powder was then treated with a 5 vol-% solution of chlorotrimethylsilane in pyridine/THF (1:9, v/v) for 2 minutes to cap free silanol groups The CPG was then washed with THF, methanol and ethyl acetate (3×10 mL of each solvent). The powder was allowed to air dry in the funnel under suction for 5 minutes, transferred to a beaker and placed in a vacuum desiccator for 44 hours. The light tan powder (0.6 g) was then stored in a −20° C. freezer until use.

Figures 3A, 3B:
In FIG. 3A native CPG was first treated with maleimide silane (19), followed by staining with SAMSA-reagent.
In FIG. 3B native CPG was treated with SAMSA-fluorescein to serve as a control.

Detection of surface maleimide by fluorescence. The derivatized CPG was assayed for maleimide functionalization using the thiol-containing fluorescein reagent, 5-((2-(and-3)-S-(acetylmercapto)succinoyl)amino)fluorescein (SAMSA fluorescein). The CPG (5 mg) was placed into a centrifuge tube, an activated solution of SAMSA fluorescein (0.5 mL) was added, the vial was shaken to mix the contents and then allowed to sit at ambient temperature for 30 minutes. Native CPG-500 (5 mg) was also placed into a centrifuge tube and treated with an activated solution of SAMSA fluorescein (prepared from 5 mg in 0.5 mL of 0.1 M NaOH, 7 μL of 6 M HCl, 0.1 mL of 0.5 M sodiumphosphate buffer, pH=7) following the same procedure to serve as a control. After 30 minutes, the mixtures were centrifuged, the supernatants were removed by pipette, and the CPG samples were suspended in water. The resulting mixtures were centrifuged, the supernatants again removed by pipette, and the CPG samples resuspended in water. This procedure was repeated until the supernatants were clear and colorless (total of 5 washes for each sample). Each powder was dispersed onto a clean sheet of plastic wrap that was folded to contain the powder. Both samples were then placed side by side on the surface of a Molecular Dynamics' Typhoon fluorescence scanner. Surface bound fluorescein was excited with a green laser followed by emission detection with a 526 nm filter (SP fluorescein filter). The photomultiplier tube settings were 600 V, sensitivity set to normal and the focal plane was set at the surface. The CPG that was treated with maleimide-silane showed a strong response consistent with maleimide functionality, whereas the native CPG-500 control did not show a response (FIG. 3). The intense response on the CPG treated with the maleimide-silane versus the native CPG-500 control shows that the maleimide functionalization of the CPG was successful.

Example 8

Functionalization of Glass Surfaces with a Diene

Scheme 10 illustrates the functionalization of glass slides and CPG with diene-silane (20) to provide support-bound dienes capable of undergoing Diels-Alder surface immobilization of dienophiles. The diene functionality is introduced onto the glass slides and CPG by condensation of diene-silane (20) with the glass surfaces as shown in Scheme 10.

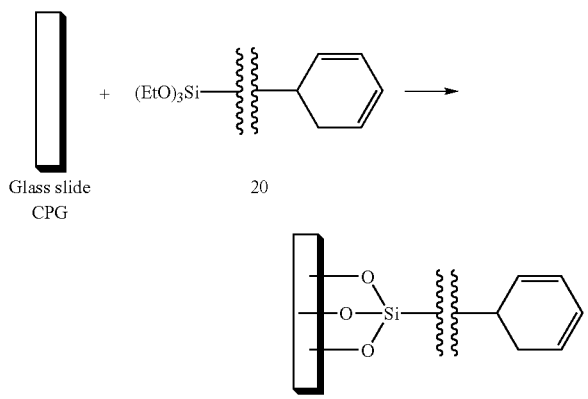

The method used to detect diene functionalized glass surfaces involves staining the glass surfaces with a maleimide-containing fluorescein reagent, which reacts with the surface-bound diene via a Diels-Alder addition reaction as illustrated in Scheme 11. The presence of fluorescein bound to the surface can then be detected with a Molecular Dynamics' Typhoon fluorescence scanner using a green laser to excite the surface-bound fluorescein followed by detection of emission using a 526 nm filter.

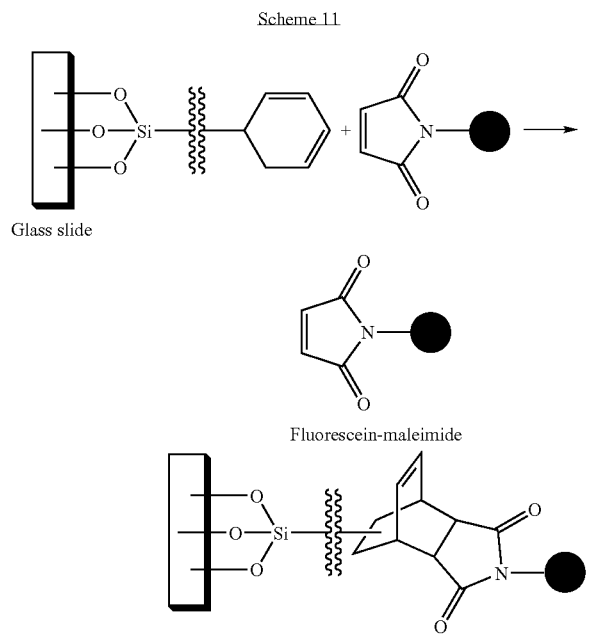

Scheme 11

Glass slide

Fluorescein-maleimide

Functionalization of glass slides with diene-silane reagent (20). Glass micro slides (4), pre-treated according to procedure #1 described in Example 7) were placed upright into a slide chamber containing a 1 vol-% solution of the diene-silane reagent (20) in toluene (25 mL). The amount of solution used was sufficient to soak only the lower half (approximately 1.5 inch) of each slide. After 15 hours, a "T" was etched into the top, right-hand corner of each slide as it was removed from the chamber. The slides were washed sequentially with toluene, methanol, methanol/water (1:1, v/v), water, methanol/water (1:1, v/v), methanol and ethyl acetate (both sides of each slide were washed with toluene (3×2 mL) by pipette and the remaining washes were done by soaking the slides in a petri dish containing 10 mL of the solvent). The slides were then allowed to air dry and were treated with a 5 vol-% solution of chlorotrimethylsilane in pyridine/THF (1:9, v/v) for 2 minutes to cap free silanol groups The slides were then washed with THF, methanol and ethyl acetate (both sides of the slide were washed with 3×2 mL of each solvent by pipette), allowed to air dry and were stored in the vacuum desiccator until use.

Figure 4:
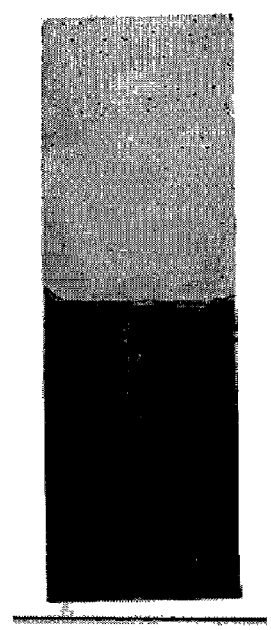
FIG. 4 is a fluorescence scan of a glass slide showing diene functionalization on the lower half of the slide that was treated with diene-silane reagent (20), followed by reaction of the diene functionalized slide with fluorescein-5-maleimide, as described in Example 8.

Detection of surface diene by fluorescence. One of the slides was assayed for diene functionalization using fluorescein-5-maleimide (Molecular Probes). Briefly, one side of the slide was completely covered with a 10 mM solution of fluorescein-5-maleimide in N,N-dimethylformamide and incubated at 6° C. overnight. The slide was then washed with water (4×10 mL) and blotted dry with a fine paper tissue. The slide was then placed on the surface of a Molecular Dynamics' Typhoon fluorescence scanner. Surface bound fluorescein was excited with a green laser followed by emission detection with a 526 nm filter (SP fluorescein filter). The photomultiplier tube settings were 600 V, sensitivity set to normal and the focal plane was set at the surface. The slide showed a strong response consistent with diene functionality on the lower half of the slide (FIG. 4). The distinct line and intense response at and below the halfway mark on the slide show that the diene functionalization of the glass slide was successful.

Diene functionalization of CPG. CPG (0.75 g, pre-treated according to the procedure described in Example 7) was stirred in a 1 vol-% solution of the diene-silane reagent (20) in toluene (25 mL) for 52 hours. The CPG was then collected on a glass-fritted funnel and washed sequentially with toluene, methanol, methanol/water (1:1, v/v), water, methanol/water (1:1, v/v), methanol and ethyl acetate (3×10 mL of each solvent). The powder was then treated with a 5 vol-% solution of chlorotrimethylsilane in pyridine/THF (1:9, v/v) for 2 minutes to cap free silanol groups The CPG was then washed with THF, methanol and ethyl acetate (3×10 mL of each solvent). The powder was allowed to air dry in the funnel under suction for 5 minutes, transferred to a beaker and placed in a vacuum desiccator for 44 hours. The white powder (0.6 g) was then stored in a −20° C. freezer until use.

Figures 5A, 5B:
In FIG. 5A CPG was treated with diene-silane (20), followed by staining with fluorescein-5-maleimide.
In FIG. 5B native CPG was treated with fluorescein-5-maleimide to serve as a control.

Detection of surface diene by fluorescence. The derivatized CPG was assayed for diene functionalization using fluorescein-5-maleimide (Molecular Probes). The CPG (5 mg) was placed into a centrifuge tube, a 10 mM solution of fluorescein-5-maleimide in DMF (0.5 mL) was added, the vial was shaken to mix the contents and incubated at 6° C. overnight. The mixture was then centrifuged, the supernatant was removed by pipette, and the CPG sample was suspended in water. The resulting mixture was centrifuged, the supernatant again removed by pipette, and the CPG sample resuspended in water. This procedure was repeated until the supernatant was clear and colorless (total of 5 washes). The powder was dispersed onto a clean sheet of plastic wrap that was folded to contain the powder. Native CPG-500 (5 mg) was also treated with fluorescein-5-maleimide to serve as a control. It was incubated in a 10 mM solution of fluorescein-5-maleimide in DMF (0.5 mL) for 2 hours at ambient temperature and then treated according to the procedure described above for the CPG treated with the diene-silane. Both samples were then placed side by side on the surface of a Molecular Dynamics' Typhoon fluorescence scanner. Surface bound fluorescein was excited with a green laser followed by emission detection with a 526 nm filter (SP fluorescein filter). The photomultiplier tube settings were 600 V, sensitivity set to normal and the focal plane was set at the surface. The CPG that was treated with diene-silane showed a strong response consistent with diene functionality (FIG. 5A), whereas the native CPG-500 control did not show a response (FIG. 5B). The intense response on the CPG treated with the diene-silane versus the native CPG-500 control show that the diene functionalization of the CPG was successful.

Example 9

Immobilization of Oligonucleotides via Diels-Alder Cycloaddition

Scheme 12 illustrates the conjugation of diene oligonucleotide (23) to maleimide functionalized glass slides and maleimide coated microtiter plates. The demonstration of conjugation was achieved by hybridization with a labeled complementary sequence and the detection of fluorescence.

Scheme 12

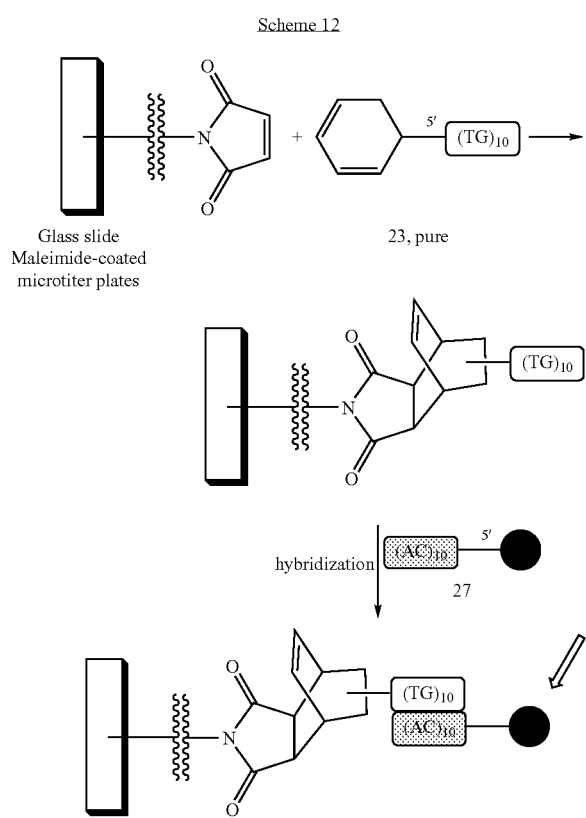

Glass slide
Maleimide-coated
microtiter plates

Figure 6:
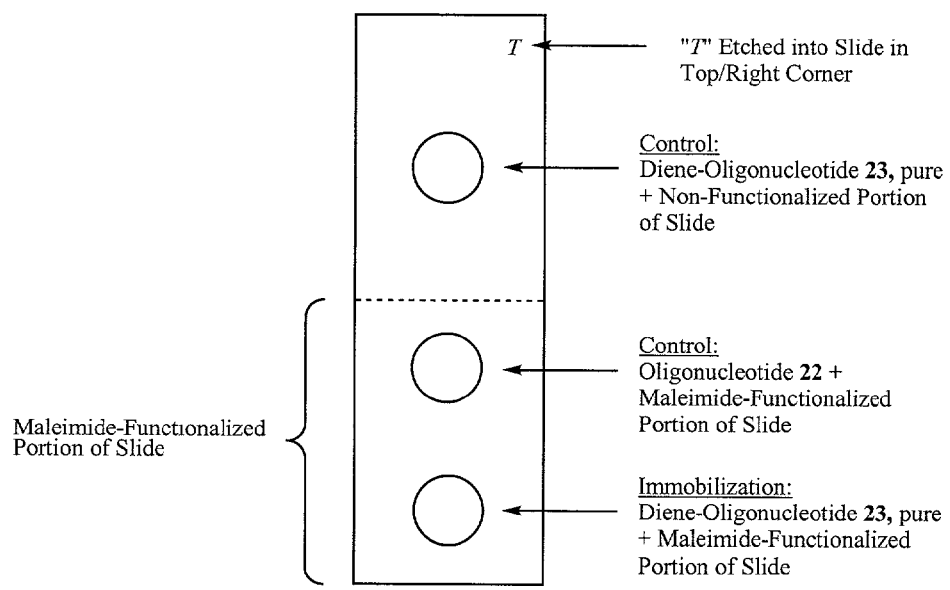
FIG. 6 shows a diagram of a slide showing placement of septa and contents of septa for demonstration of Diels-Alder surface immobilization of an oligonucleotide on maleimide functionalized glass micro slides as described in Example 9.

Conjugation of diene-oligonucleotide (23) to maleimide functionalized glass slides. Two maleimide coated slides (1 pre-treated according to procedure #1 and 1 pre-treated according procedure #2, as described in Example 7) were each equipped with 3 silicone rubber septa (standard taper 14/20) running linearly up the slides using plastic ties to firmly secure the septa to the slides. Two septa were affixed to the lower maleimide-functionalized half of each slide and one septum was affixed to the upper non-functionalized half of each slide. The outline of the septa was etched into the slide that was pre-treated according to procedure #2. A 4 pmol/µL solution of 5′-diene-oligonucleotide (23), pure, in 100 mM Na$_2$HPO$_4$ buffer at pH=6.5 (125 µL) was added to the septum placed at the bottom of each slide to demonstrate surface immobilization of an oligonucleotide on micro slides. (FIG. 6). A 4 pmol/µL solution of control oligonucleotide (22) (SEQ ID NO:1) in 100 mM Na$_2$HPO$_4$ buffer at pH=6.5 (125 µL) was added to the septum placed in the middle of each slide as a control to check for potential non-specific binding of the oligonucleotide to the functionalized portion of the slide. A 4 pmol/µL solution of 5′-diene-oligonucleotide (23), pure, in 100 mM Na$_2$HPO$_4$ buffer at pH=6.5 (125 µL) was added to the septum placed at the top of each slide as a control to check for potential non-specific binding of the (23) to the non-functionalized portion of the slides. The slides were incubated for 1 hour at 37° C. and then the septa were removed and the slides were soaked 3 times each in a petri dish containing TRIS-buffered saline containing Tween® 20 (TBST) (10 mM TRIS-Cl, pH 8, 150 mM NaCl, 0.1% Tween® 20).

Figure 7:
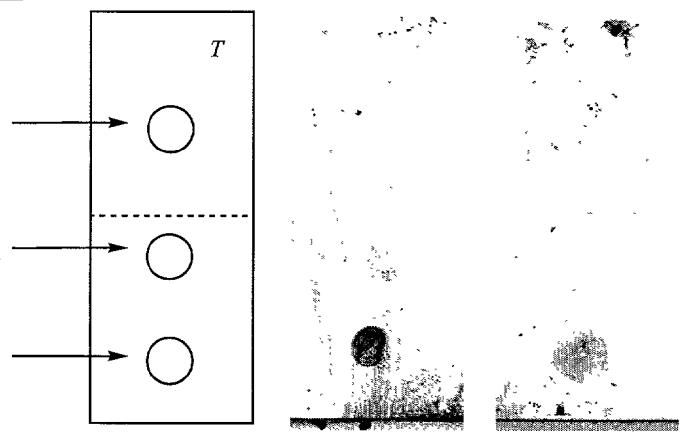
FIG. 7 illustrates fluorescence scans of glass slides showing successful Diels-Alder surface immobilization of 5'-diene-oligonucleotide (23) on maleimide-functionalized glass micro slides. Slide "1" was pre-treated with 2N NaOH then hot 2N HCl prior to maleimide-functionalization. Slide "2" was pre-treated only with 2N HCl. Spots visible on each slide are where compound (23) came into contact with the maleimide-functionalized portion of the slide prior to hybridization with complementary 5'-fluorescein-oligonucleotide (27); areas of the slides that came into contact with controls showed no response.

Detection of oligonucleotide immobilization on glass slides. The slides, pulled from the buffer solutions, were immediately (to prevent the slides from drying out) immersed in a 4 pmol/µL solution of complementary 5′-fluorescein-oligonucleotide (27) in 5× standard saline citrate (SSC) containing 0.1% sodium dodecyl sulfate (SDS) (750 mM NaCl, 75 mM Na citrate, pH=7, 0.1% SDS) in a petri dish (ca. 10 mL). The slides were incubated for 30 minutes at 55° C. and were then soaked 3 times each in a petri dish containing TBST. The slides were then placed on the surface of a Molecular Dynamics' Typhoon fluorescence scanner. The fluorescein was excited with a green laser followed by emission detection with a 526 nm filter (SP fluorescein filter). The photomultiplier tube settings were 800 V, sensitivity was normal, and the focal plane was set at the surface. The slides each showed a strong response where diene-oligonucleotide (23) came into contact with the maleimide-functionalized portion of the glass slide (27) (FIG. 7). The two controls on each slide showed no response indicating the lack of non-specific binding of (22) to the maleimide-functionalized portion of the slide and the lack of non-specific binding of (23) to the non-functionalized portion of the slide. The outlines of the septa etched on the slide pre-treated according to procedure #2 (slide "2") are faintly visible in the scan.

Conjugation of diene-oligonucleotide (23) to maleimide coated microtiter plates. 200 µL of either the 5′-diene-oligonucleotide (23), crude and pure, or control oligonucleotide (22) were added to maleimide microtiter plates (Pierce Cat #15150ZZ) at a concentration of 2.5 pmol/µL in 100 mM Na$_2$HPO$_4$ buffer at pH=5.5, 6.5 or 7.7 as indicated. A well containing only 100 mM pH=6.5 Na$_2$HPO$_4$ was also included as a control for non-specific binding of labeled complementary oligonucleotide (27). For conjugation via Diels-Alder reaction the plates were incubated for 2 hours at 37° C. Wells containing the immobilized oligonucleotides were aspirated and washed 3 times with TBST (10 mM Tris-Cl pH=8.0, 150 mM NaCl, 0.1% Tween 20).

Figure 8:
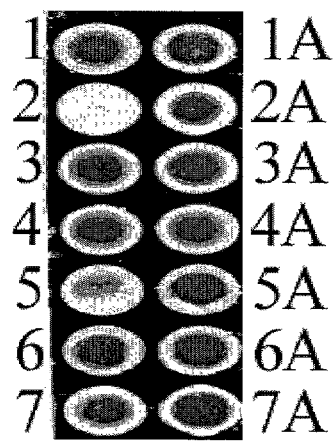
FIG. 8 illustrates the conjugation of diene-oligonucleotide (23) to maleimide-coated micro titer plates after hybridization with complementary fluorescein labeled sequence 5'-fluorescein-$(CA)_{10}$ (27) (SEQ ID NO:2). Wells 1-3 were treated with diene-oligonucleotide (23), pure, and wells 4-6 were treated with diene-oligonucleotide (23), crude. Wells 1A-6A are the corresponding oligonucleotide (22) controls. Wells 7 and 7A are the buffer controls. Wells 1, 1A, 4, 4A were incubated at pH=5.5, wells 2, 2A, 5, 5A at pH=6.5 and wells 3, 3A, 6A at pH=7.7.

Detection of oligonucleotide immobilization on maleimide coated microtiter plates. Equal molar amounts of labeled complementary oligonucleotide (27) were added to the wells in 5×SSC+0.1% SDS (750 mM NaCl, 75 mM Na Citrate, pH=7.0) and hybridized at 55° C. for 30 minutes. Following hybridization all samples were washed with TBST (3×200 mL). Plates and slides were placed on the surface of a Molecular Dynamics Tyhpoon fluorescence scanner and the fluorescein was excited with a green laser followed by emission detection with a 526 nm filter (SP fluorescein filter). Photomultiplier tube settings were 800 V, sensitivity was set to normal and the focal plane was set at the surface. Oligonucleotide immobilization was most efficient at pH=6.5 as shown in FIG. 8. The control oligonucleotide (22) set of reactions showed no non-specific binding as did all the buffer controls. The maleimide functionalized slide also demonstrates oligonucleotide immobilization as evident from the signal generated only from the area on the slide that was reacted with the silane-maleimide reagent (19).

Example 10

Conjugation of 5′-Diene-Oligonucleotide (24) to Maleimide Functionalized CPG

Maleimide-CPG was incubated with oligonucleotide (24) to form the Diels-Alder adduct as illustrated in Scheme 13. Immobilization was verified by photometric determination of DMT after cleavage with acid.

Scheme 13

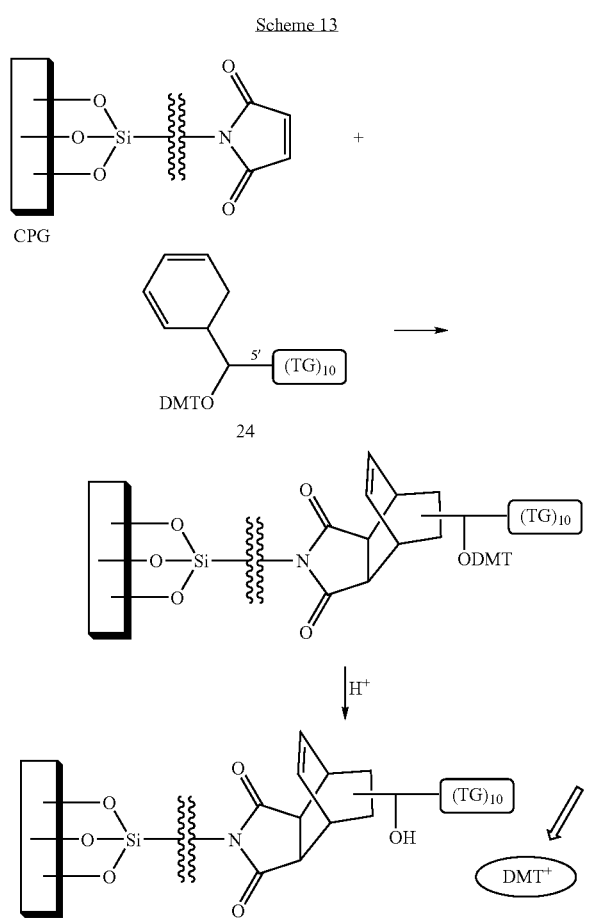

Titration of maleimide functionalized CPG with 5'-diene-oligonucleotide (24). A series of increasing amounts of diene (DMT)-oligonucleotide (24) (see Table 2) in Na$_2$HPO$_4$ buffer (100 mM, pH=6.5, 350 µL) was added to maleimide derivatized CPG (10 mg, each), weighed each in centrifuge tubes. The mixtures were incubated at 37° C. for 1 hour under shaking (to keep an optimal mixing of CPG). Each of the mixtures was centrifuged and the supernatant was removed by pipette. The CPG samples were suspended in water (1 mL) and the resulting mixtures were centrifuged and the supernatants again removed by pipette. This washing procedure was repeated three times for each sample before drying in a speed vacuum concentrator. The results of this titration are depicted graphically in FIG. 9.

Time dependence of reaction between maleimide-CPG and diene(DMT)-oligonucleotide (24). Six samples were prepared by addition of diene(DMT)-oligonucleotide (24) (37 mmol) to each of 6 tubes containing a solution of maleimide derivatized CPG (10 mg, each) in Na$_2$HPO$_4$ buffer (100 mM, pH=6.5, 100 µL), that had been pre-equilibrated at 37° C. The conjugation reaction was stopped after different time intervals (see Table 3) by removal of supernatant solution of (24) and washing of the CPG as described above. The results are depicted graphically in FIG. 10.

Loading Determination. To each CPG containing tube a 3% solution of p-toluenesulfonic acid in CH$_3$CN (0.75 mL) was added and the resulting mixture was agitated for 1 minute. For determination of loading the absorbance @497 nm of the supernatant was determined photometrically using the following equation:

$$L = \frac{V \cdot ABS}{m_{resin} \cdot \varepsilon \cdot d}$$

$V = 1 \text{ cm}^3$
$m_{resin} = 10 \text{ mg}$
$\varepsilon = 71,200 \text{ cm}^2/\text{mmol}$
$d = 1 \text{ cm}$ $L[\text{umol/g}] = 1.4045 \cdot ABS$ Example 11

Conjugation of 5'-Maleimide-Oligonucleotide (26) to Diene Coated Glass Surfaces

Scheme 14 shows the conjugation of maleimide-oligonucleotide (26) with diene functionalized glass surfaces. The demonstration of conjugation was achieved by hybridization with the labeled complementary sequence (27) and the detection of fluorescence as described above.

Scheme 14

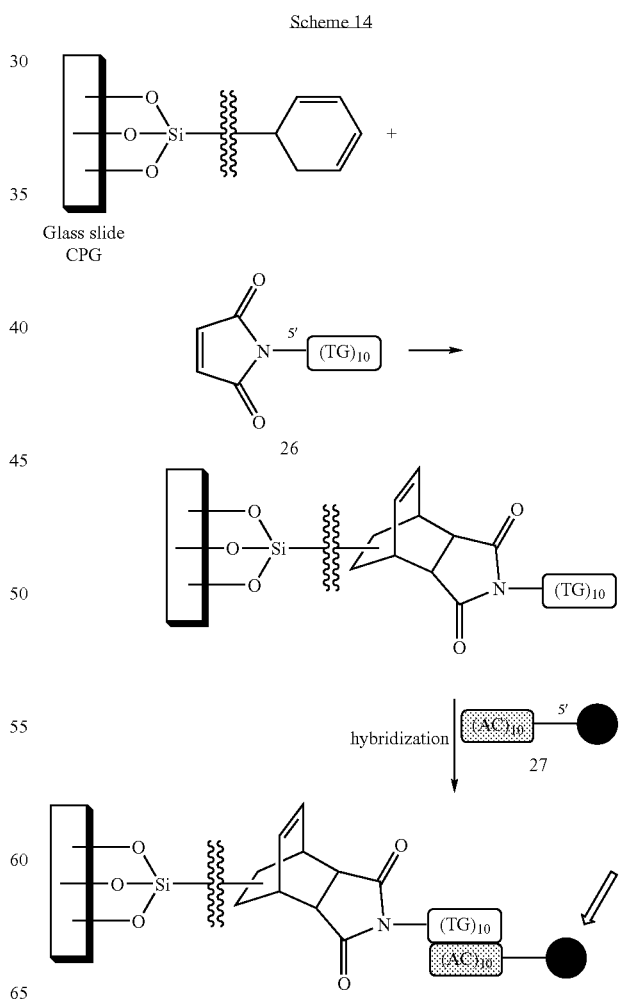

Conjugation of maleimide-oligonucleotide (26) to diene-functionalized glass slides. One diene-coated slide was equipped with 3 silicone rubber septa (standard taper 14/20) running linearly up the slide. The septa were compressed onto the slide between two 3×5×¼ inch pieces of acrylic sheet that were fastened together on both sides of the slide using thumb screws. The upper acrylic sheet contained 3/16-inch holes directly above the middle of the septa to allow needle-access to the septa. Two septa were affixed to the lower diene-functionalized half of the slide and one septum was affixed to the upper non-functionalized half of the slide. A 4 pmol/μL solution of maleimide-oligonucleotide (26) in 100 mM $Na_2HPO_4$ buffer at pH=6.5 (125 μL) was added to the septum placed at the bottom of the slide to demonstrate surface immobilization of an oligonucleotide on a micro slide. A 4 pmol/μL solution of control oligonucleotide (22) in 100 mM $Na_2HPO_4$ buffer at pH=6.5 (125 μL) was added to the septum placed in the middle of the slide as a control to check for potential non-specific binding of the oligonucleotide to the functionalized portion of the slide. A 4 pmol/μL solution of maleimide-oligonucleotide (26) in 100 mM $Na_2HPO_4$ buffer at pH=6.5 (125 μL) was added to the septum placed at the top of each slide as a control to check for potential non-specific binding of the maleimide-oligonucleotide (26) to the non-functionalized portion of the slide. The slide was incubated for 1 hour at 37° C. and then the septa were removed and the slide was soaked 3 times each in a petri dish containing TRIS-buffered saline containing Tween® 20 (TBST) (10 mM TRIS-Cl, pH=8, 150 mM NaCl, 0.1% Tween® 20).

Figure 11:
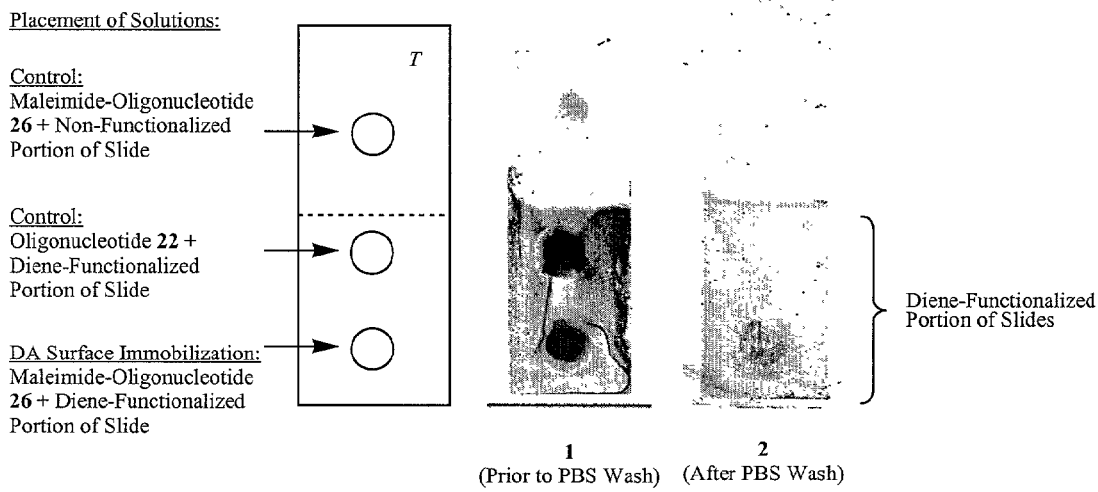
FIG. 11 illustrates fluorescence scans of glass slides showing successful Diels-Alder surface immobilization of maleimide-oligonucleotide (26) on diene functionalized glass micro slides. Slide "1" is prior to the wash with phosphate buffered saline (PBS) illustrating the necessity of the wash to remove non-covalently bound oligonucleotide from the glass surface. Slide "2" is after the PBS wash. The single fluorescent response visible on the slide is where compound (26) came into contact with the diene-functionalized portion of slide prior to hybridization with complementary-5'-fluorescein-oligonucleotide (27). After the PBS wash, areas of the slide that came into contact with controls showed no response.

Detection of oligonucleotide immobilization on glass slides. The slide, pulled from the buffer solution, was immediately (to prevent the slide from drying out) immersed in a 4 pmol/μL solution of complementary 5'-fluorescein-oligonucleotide (27) in 5×SSC containing 0.1% SDS (10 mL) in a petri dish. The slide was incubated for 30 minutes at 55-60° C. The slide was then soaked 3 times each in a petri dish containing TBST. The slide was analyzed using the Molecular Dynamics Typhoon fluorescence scanner, but the results indicated that the washing conditions were insufficient to remove non-specifically bound oligonucleotide from the plate (FIG. 11, slide "1"). The slide was then washed 3 times in a petri dish containing 1×PBS (phosphate-buffered saline solution) with 0.1% SDS. The slide was again analyzed using the Molecular Dynamics Typhoon fluorescence scanner and showed a strong response only where maleimide-oligonucleotide (26) came into contact with the diene-functionalized portion of the glass slide and then hybridized with (27) (FIG. 11, slide "2"). The two controls on the slide showed no response indicating that the washing conditions were sufficiently stringent to remove non-covalently bound oligonucleotide (22) from the diene-functionalized portion of the slide and non-covalently bound maleimide-oligonucleotide (26) from the non-functionalized portion of the slide. The diene-functionalized portion of the slide (lower half) shows some fluorescence outside of the area that was reacted with (26) indicating there is some residual non-specific binding of (27) to the diene-functionalized portion of the slide.

Conjugation of maleimide-oligonucleotide (26) to diene-functionalized CPG. Diene-coated CPG (15 mg) was placed into a centrifuge tube. A 4 pmol/μL solution of maleimide-oligonucleotide (26) in 100 mM $Na_2HPO_4$ buffer at pH=6.5 (125 μL) was added, the vial was shaken to mix the contents, and then incubated for 1 hour at 37° C. The mixture was then centrifuged, the supernatant was removed by pipette, and the CPG sample was suspended in TRIS-buffered saline containing Tween® 20 (TBST) (10 mM TRIS-Cl, pH=8, 150 μM NaCl, 0.1% Tween® 20). The resulting mixture was centrifuged, the supernatant again removed by pipette, and the CPG sample resuspended in TBST. This procedure was repeated for a total of 3 washes. In addition, two control experiments were run following the above procedure. One of the control experiments involved using control oligonucleotide (22) in place of compound (26) to check for potential non-specific binding of the oligonucleotide to diene-functionalized CPG. The other control experiment involved using non-functionalized CPG capped with chlorotrimethylsilane as a control to check for potential non-specific binding of the maleimide-oligonucleotide (26) to non-functionalized CPG.

Figures 12A, 12B:
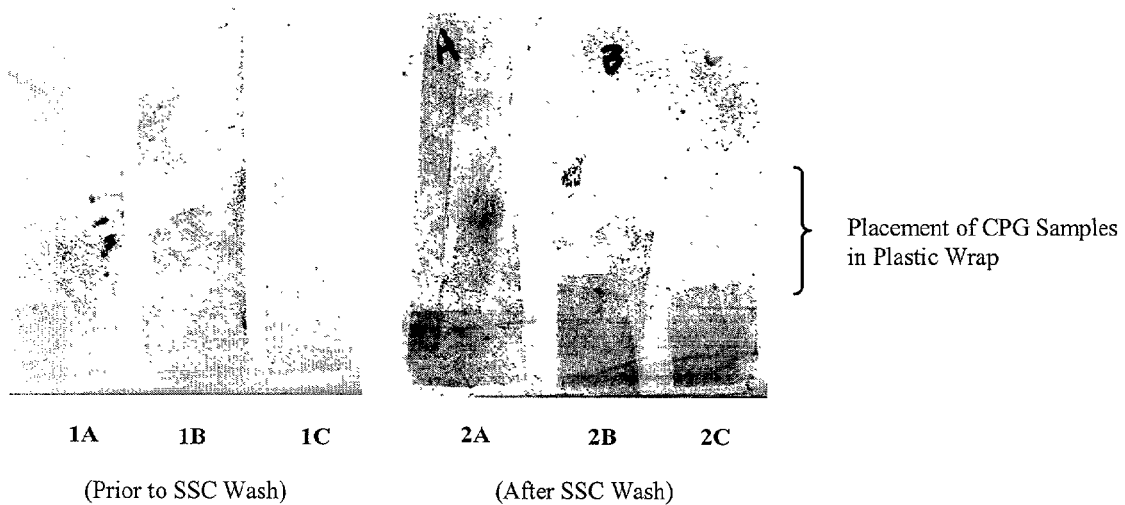
FIG. 12A is prior to the wash with a mixture of 5×0.3 M sodium citrate and 3 M sodium chloride (SSC)
FIG. 12B is after the SSC wash. The fluorescent response visible on the sample labeled "2A" is where compound (26) came into contact with diene-functionalized CPG prior to hybridization with complementary 5'-fluorescein-oligonucleotide (27). After the SSC wash, the control samples labeled "2B" and "2C" showed relatively little response.

Detection of oligonucleotide immobilization on CPG. A 4 pmol/μL solution of complementary 5'-fluorescein-oligonucleotide (27) in 5×SSC containing 0.1% SDS (125 μL) was immediately added to each of the CPG samples obtained after reaction with maleimide-oligonucleotide (26) and washings. The samples were incubated for 30 minutes at 55-60° C. The samples were then washed 3 times as described above with 1×PBS (phosphate-buffered saline solution) with 0.1% SDS. After the final wash was removed by pipette, each sample was dispersed onto a clean sheet of plastic wrap and the plastic wrap was folded to contain the powder. The three samples, individually wrapped, were then placed side-by-side on the surface of a Molecular Dynamics' Typhoon fluorescence scanner. The samples were analyzed using the Typhoon fluorescence scanner, but the results indicated that the washing conditions were insufficient to remove non-specifically bound (26) from the diene-functionalized CPG (FIG. 12A). The samples were then transferred back into their original centrifuge tubes and washed 3 times with 0.5×SSC+0.1% SDS (significant loss of each sample occurred during transfers). The samples were then again dispersed onto sheets of plastic warp and analyzed using the Typhoon fluorescence scanner. The diene-functionalized CPG sample that was treated with maleimide-oligonucleotide (26) showed a strong response after hybridization with 27 (FIG. 12B, slide "2A"). The two controls showed comparatively little response indicating that the Diels-Alder surface immobilization of maleimide-oligonucleotides can be performed on diene-functionalized CPG.

Example 12

Preparation of a Diene Modified Oligonucleotide

Scheme 15 illustrates the preparation of diene modified oligonucleotide (29) from N-hydroxysuccinimide ester (10), the synthesis of which is described in Example 2.

Scheme 15

NH$_2$(CH$_2$)$_6$OPO$_2$-5'-d(CTACCTACGATCTGACTAGC)-3'

28 (ODN99225) (SEQ ID NO: 3)

$\xrightarrow[\text{ACN}]{\underset{\text{(25 mM)}}{\text{sodium borate}}} 10$

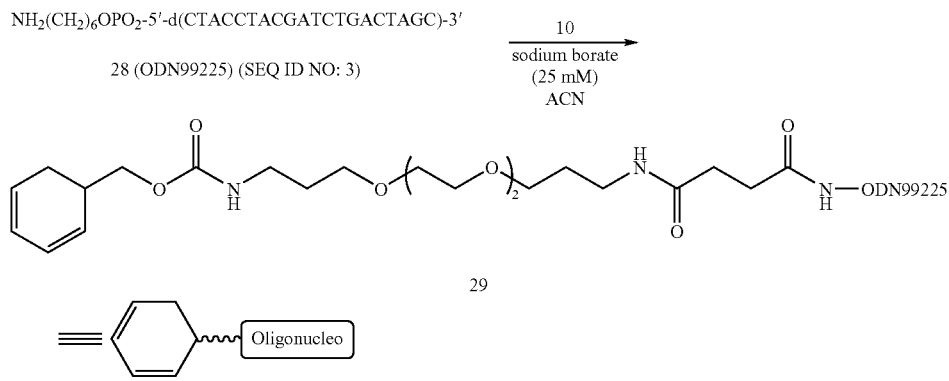

29

5'-Amine modified oligodeoxynucleotide (28) (ODN99225) was prepared employing standard solid phase automated synthesis on controlled pore glass (CPG) via the phosphoramidite method. After deprotection and cleavage from the CPG support, the crude amine-modified oligonucleotide was purified by preparative anion exchange chromatography on a 200 mL Source 15Q column (quaternary ammonium functionalized, monodisperse polystyrene beads) eluting with the gradient set forth in Table 4.

Product containing fractions were combined and concentrated in vacuo. The material was desalted by a HPLC-method which involved adsorbing the crude material onto a C18 column in water, washing with a 1 M NaCl solution followed by water, then eluting the material with EtOH. The amine oligonucleotide was coupled to N-hydroxysuccinimide ester (10) in a mixture of 25 mM sodium borate buffer and acetonitrile (40%) employing roughly 4 equivalents of compound (10). Analytical reversed phase chromatography indicated a final product purity of 95.9%. Electrospray mass spectrometric analysis confirmed the identity of the oligonucleotide conjugate (29) (observed MW=6639.0; calcd MW=6639).

Example 13

HPLC Monitoring of a Diels-Alder Reaction Employing a Cyclohexadiene Oligonucleotide To confirm the Diels-Alder reactivity of diene conjugate (29), labeling with commercially available maleimide dienophiles (30) (Aldrich) and (31) (Molecular Biosciences) were carried out as illustrated in Scheme 16. Briefly, to a solution of (29) (1.5 mM) in phosphate buffer (pH=6.8) were added 100 equivalents of compound (30) or (31). The progress of the reaction was monitored by analytical anion exchange chromatography with samples taken every 5 minutes (as described below). Treatment of (29) with N-ethyl maleimide (30) resulted complete conversion to adduct (32) within 5 minutes, while biotin maleimide 31 required 20 minutes.

Scheme 16

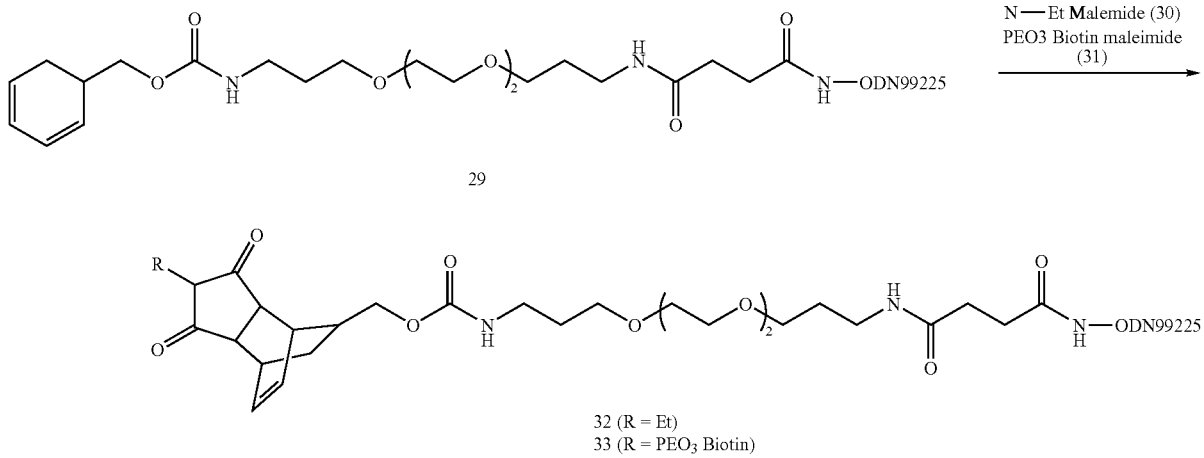

32 (R = Et)
33 (R = PEO$_3$ Biotin)

The progress of the Diels Alder reaction was monitored as follows: 2 μL of reaction solution was removed, treated with 8 μL of 0.1 M NaOH (to quench the maleimide), vortexed for 30 seconds and diluted with 50 μL of H$_2$O. Of this 60 μL solution, 50 μL (~16.7 μg of oligonucleotide) was injected onto a 5 micron C18 Jupiter column. The samples were run using a buffer system of TEAA (pH 7.0; Eluent A) and acetonitrile (Eluent B) as outlined in Table 5.

Example 14

Preparation of Diene Modified Polyethylene Glycol Substrates

Scheme 17 illustrates the synthesis of a cyclohexadiene-PEG (34).

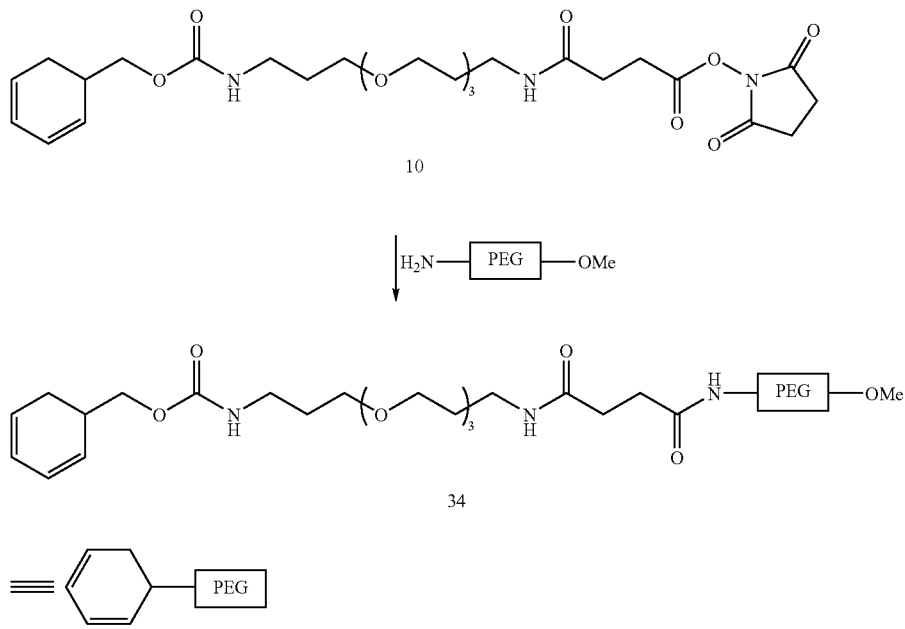

Scheme 17

Diene (10) was treated sequentially with carbonyldiimidazole and methoxy polyethylene glycol amine (MW=5000). The resulting carbamate product was purified by careful dropwise addition into cold ether and collection of the precipitate by filtration. The material obtained was used without further purification in surface immobilization studies. Similarly, hydroxymethylanthracene (35) was converted to the analogous PEG derivative (36) using the same method as illustrated in Scheme 18.

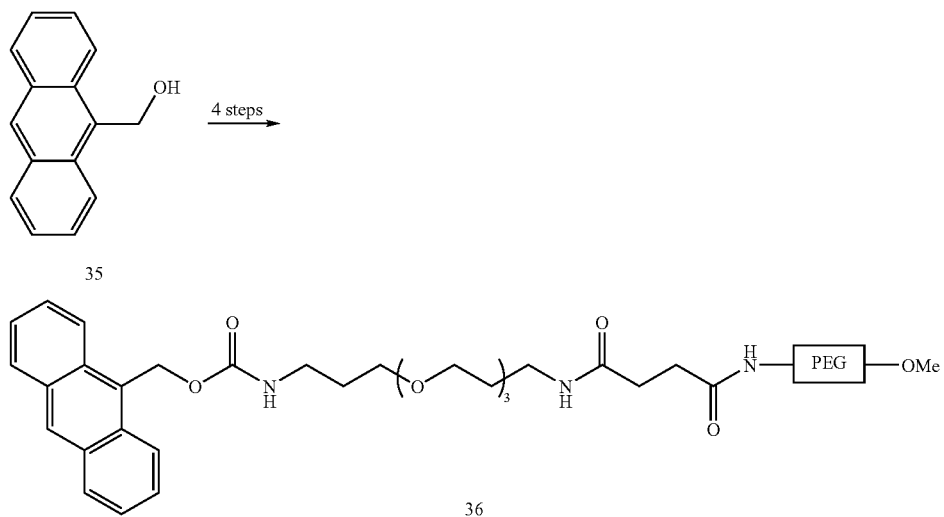

Scheme 18

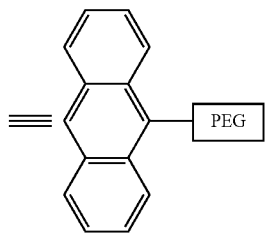

Example 15

Preparation of a Maleimide-Coated Flow Cell for the BIAcore

Scheme 19 illustrates the preparation of a dienophile derivatized CM5 BIAcore flow cell surface.

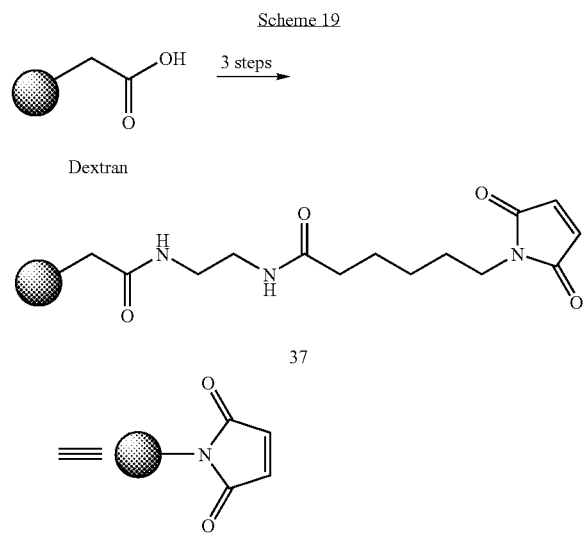

The dienophile CM5 BIAcore flow cell surface was prepared by subjecting the commercially available chip (coated with a matrix of carboxymethyl dextran) to a 3 step derivatization procedure, as illustrated in Scheme 19. Briefly, the carboxy groups were activated as the N-hydroxysuccinimide esters (via treatment with EDC/NHS), followed by the addition of diamine linker (ethylene diamine, to provide a reactive primary amine surface), which was treated with a commercially available bifunctional crosslinking reagent. The resulting dienophile cell surface (37) was reproducibly prepared in this manner as evidenced by the measurement of the Biacore sensorgram with each experiment.

The sensorgrams were obtained using a BIAcore 2000 instrument (Pharmacia Biosensor AB, Uppsala, Sweden. Lofas et al. (1991) Sens. Actuators B 5:79-84; Malmqvist (1993) Nature 361:186-187.) employing a biosensor technique called "real-time biomolecular interaction analysis" (BIA), which allows the real-time monitoring of interactions between two or more molecules, such as proteins or nucleic acids and small molecules, such as signaling substances and pharmaceuticals (Pharmacia Biosensor AB, cf. http://www-.biacore.com). The detection principle relies on the optical phenomenon of "surface plasmon resonance" (SPR), which detects changes in the refractive index of the solution close to the surface of the sensor chip (Brockman et al. (1999) J. Am. Chem. Soc. 121:8044-8051 and references cited therein). This is in turn directly related to the concentration of solute in the surface layer. To perform a BIA analysis, one interactant is immobilized in a dextran matrix on the sensor chip, which forms one wall of a micro-flow cell. Sample containing the other interactant(s) is then injected over the surface in a controlled flow. Any change in surface concentration resulting from interaction is detected as an SPR signal, expressed in resonance units (RU). The continuous display of RU as a function of time, referred to as a Biacore sensorgram, thus provides a complete record of the progress of association and dissociation.

Maleimide derivatization protocol (Khilko (1993) J. Bio. Chem. 268:15425-15434):

Flow rate=10 μL/min with pH 6.8 PBS running buffer

Injection Sequence:

1. 40 μL of EDC-NHS mixture (from stock solutions: NHS at 11.5 mg/mL and EDC at 75 mg/mL).

2. 100 μL of 1.0 M ethylenediamine diHCl at pH 6.0.

Figure 13:
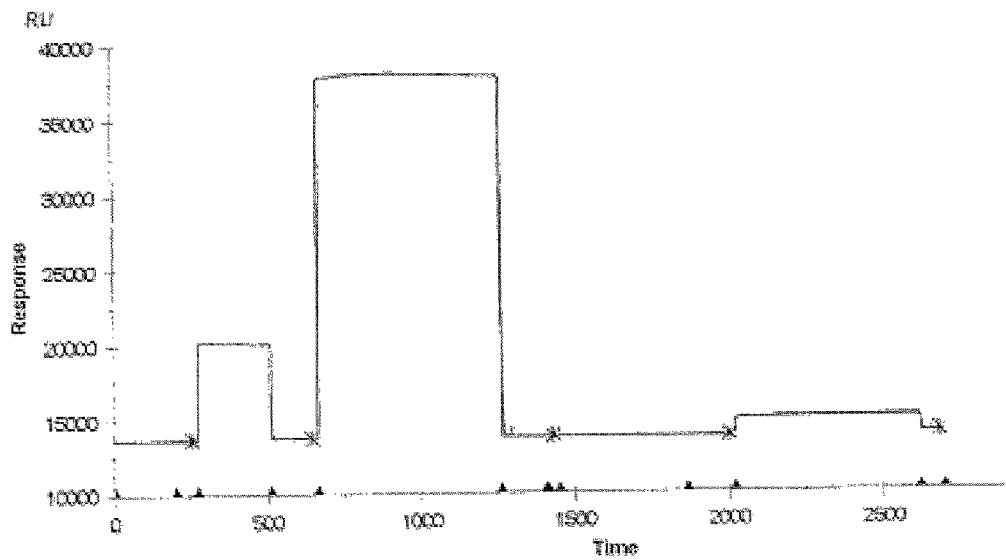
FIG. 13 is an overlaid Biacore sensorgram illustrating the reproducibility of the formation of the maleimide-coated BIAcore flow cell surface (37) described in Example 15.

3. 100 μL of 25 mM sulfo-EMCS (NHS/maleimide bifunctional reagent in pH 6.8 running buffer. The overlaid Biacore sensorgrams depicted in FIG. 13 show the consistent results of this method.

Example 16

Comparison of Surface Derivatization via PEG-SH (Michael Addition) vs PEG-Diene (Diels-Alder Surface Immobilization)

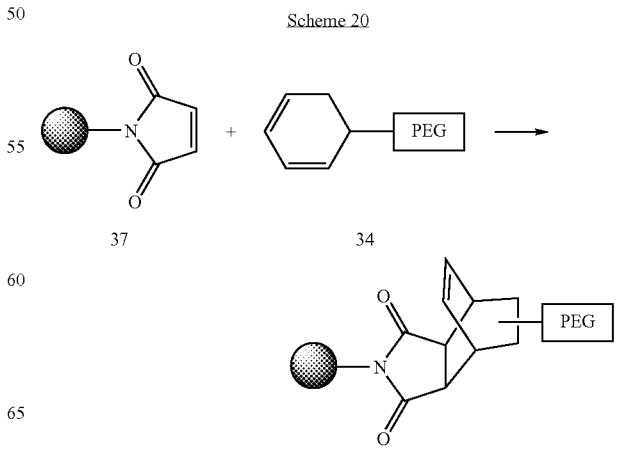

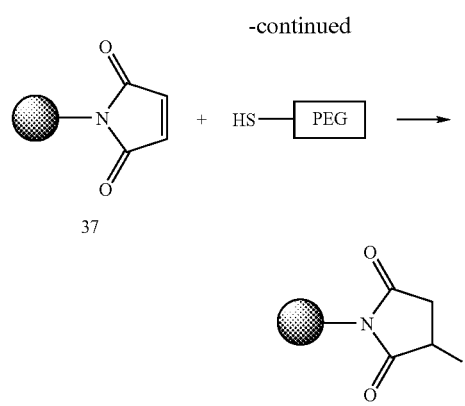

Figure 14:
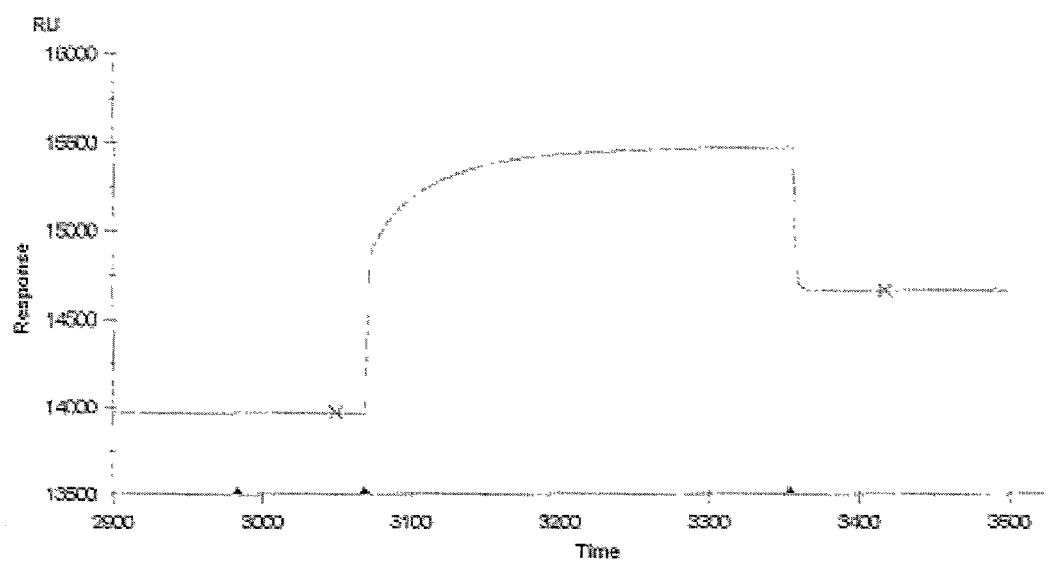
FIG. 14 is a Biacore sensorgram of the product of the Michael-addition between maleimide-coated BIAcore flow cell surface (37) and MeO-PEG-SH, which is described in Example 16.

By subjecting the dienophile flow cell surface described in Example 15 to MeO-PEG-SH (MW=5000; pH=6.8 phosphate buffer, 10 μL/min flow rate), the functional activity of the surface was confirmed as evidenced by the Biacore sensorgram depicted in FIG. 14.

Figure 15:
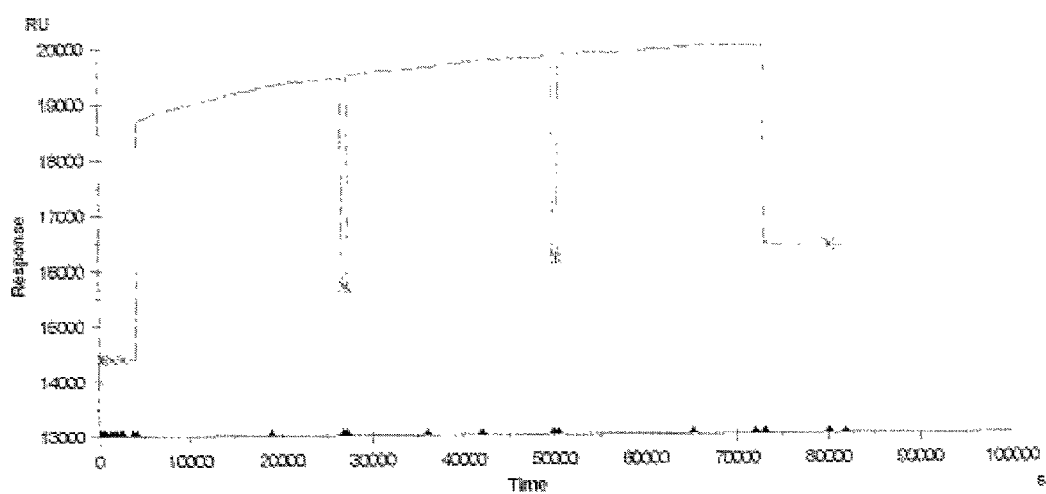
FIG. 15 is a Biacore sensorgram of the product of the Diels-Alder reaction between maleimide-coated BIAcore flow cell surface (37) and PEG-diene substrate (34), described in Example 16.

Likewise, addition of the PEG-diene substrate (34) prepared in Example 14 afforded the Biacore sensorgram depicted in FIG. 15, confirming the dienophile reactivity of the flow cell surface and suggesting that the relative rate of the Diels-Alder surface immobilization is substantially slower than the Michael addition method employing a PEG-thiol (12 hours vs 10 minutes).

Example 17

BIAcore Diels-Alder Reaction with Anthracene-PEG (36)

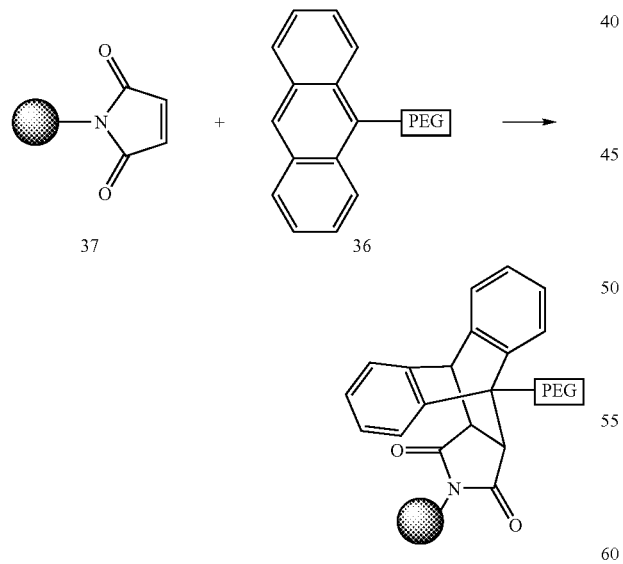

Figure 16:
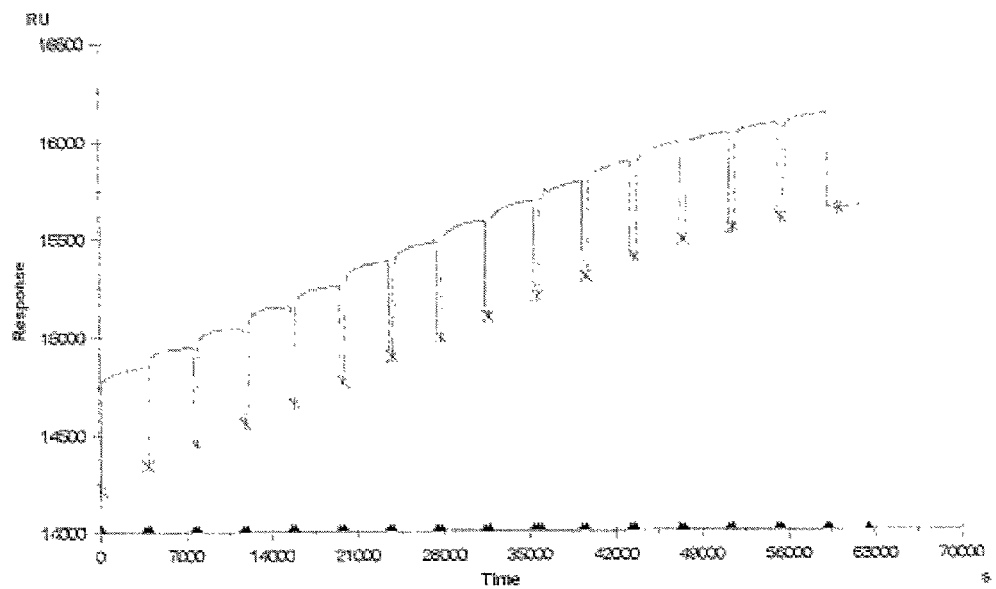
FIG. 16 is a Biacore sensorgram of the product of the Diels-Alder reaction between maleimide-coated BIAcore flow cell surface (37) and PEG-anthracene substrate (36), described in Example 17.

Reaction of dienophile derivatized CM5 BIAcore flow cell surface (37) with the anthracene derivative (36) (preparation described in Example 14), using the method described in Example 16, provided compound (38), which is described in the literature to have improved aqueous Diels-Alder reaction kinetics. Enhanced surface immobilization was observed using compound (36), compared to compound (34). As can be seen FIG. 16, a comparable response was observed in approximately half the time.

Example 18

Figure 17:
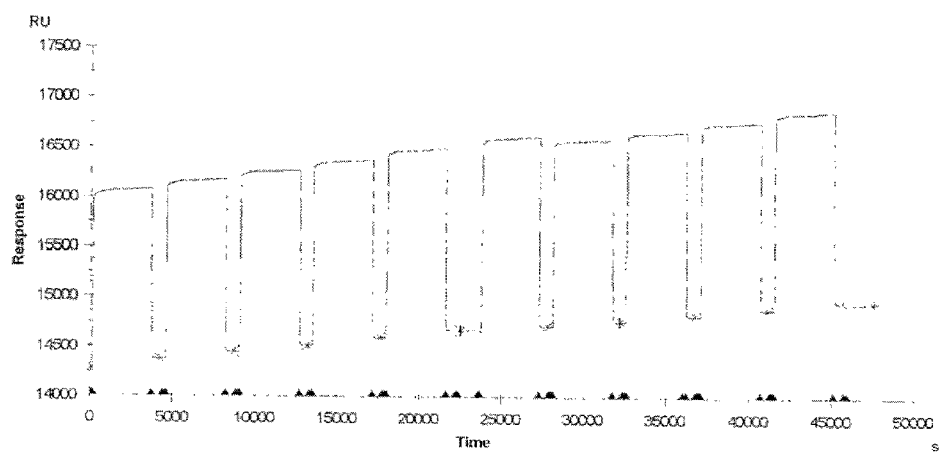
FIG. 17 is a Biacore sensorgram of the product of the Diels-Alder reaction between maleimide-coated BIAcore flow cell surface (37) and cyclohexadiene modified oligonucleotide (29), described in Example 18.
Figure 18:
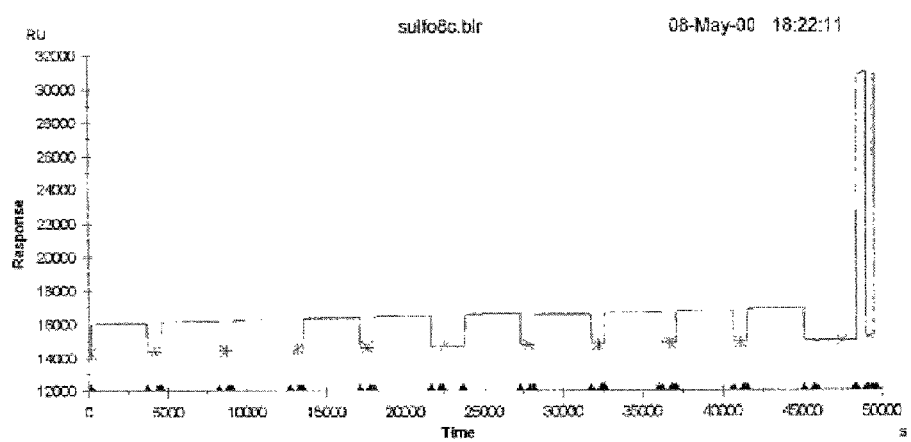
FIG. 18 is a Biacore sensorgram of the product of the Diels-Alder reaction between maleimide-coated BIAcore flow cell surface (37) and cyclohexadiene modified oligonucleotide (29), upon hybridization of the immobilized sequence with its complementary oligonucleotide sequence.

BIAcore Surface Immobilization of Diene Modified Oligonucleotide (29) via the Diels-Alder Conjugation and Hybridization with the Complementary Sequence Surface immobilization of the cyclohexadiene modified oligonucleotide (29), followed by hybridization with the complementary oligonucleotide sequence is illustrated in Scheme 22. Briefly, the Diels-Alder reaction between dienophile (37) and diene (29) was carried out using the method described in Example 16 to provide the immobilized oligonucleotide, compound (39). The sensorgram results are set forth in FIG. 17. Immobilized oligonucleotide (39) was then hybridized with its complementary sequence using standard means. The Biacore sensorgram depicted in FIG. 18, reveals an increased response upon association of the complementary oligonucleotide sequence to the immobilized oligonucleotide, thus confirming the above immobilization technique.

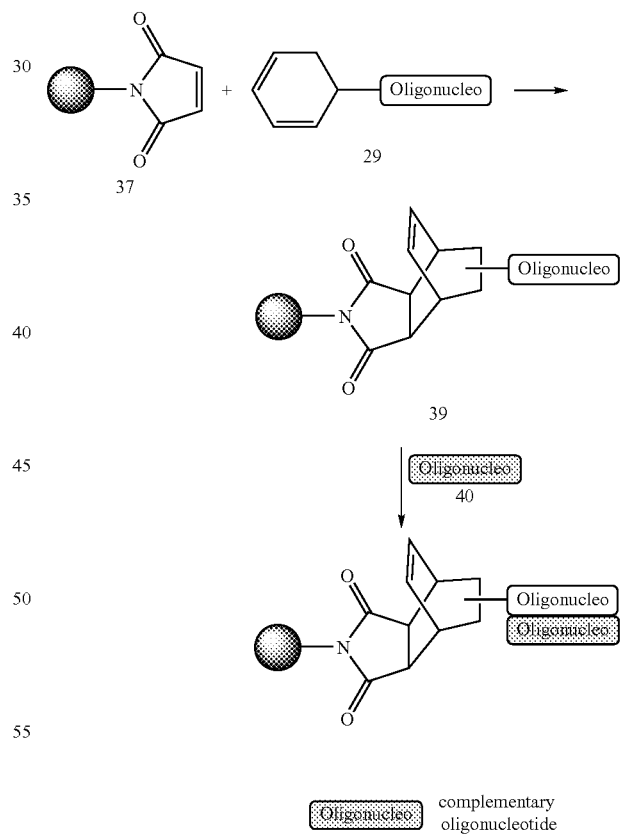

Example 19

Synthesis of Anthracene-Silane Reagent (42)

Scheme 23 illustrates the synthesis of an anthracene silane reagent for the functionalization of glass surfaces. Briefly, with reference to Scheme 23 hydroxymethylanthracene (35) was reacted with CDI to form imidazolate (41). Imidazolate (41) was then reacted with propylamino silane (17), to provide anthracene-silane reagent (42), which was then used for glass derivatization as illustrated in Scheme 24 below.

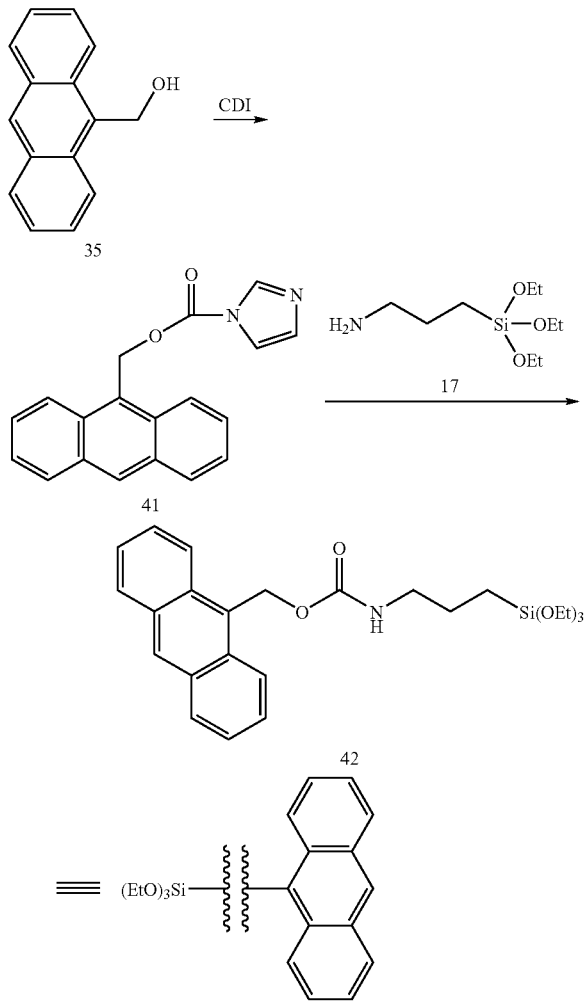

Synthesis of anthracene-silane reagent (42). To a stirring solution of (35) (4.8 mmol, 1.0 g) in DMF (16 mL, 0.3 M) was added CDI (5.28 mmol, 0.856 g). After 3 hours, the reaction was pushed to completion by the addition of CDI (1.06 mmol, 0.171 g). The complete formation of the imidazolate (41) was confirmed by $^1$H NMR, which showed that the methylene of the alcohol had shifted from 5.65 ppm to 6.45 ppm. This is characteristic of the expected shift. To this stirring solution was added aminopropyltriethoxy silane (17) (4.8 mmol, 1.06 g). The reaction was placed under an argon atmosphere and allowed to stir overnight. The reaction was complete by $^1$H NMR, which showed that the methylene of the imidazolate had shifted from 6.45 ppm to 6.15 ppm, characteristic of conversion to the expected carbamate product (42).

To the NMR sample in CDCl$_3$ was added D$_2$O (200 µL). The tube was vortexed for 1 minute, and then a second $^1$H NMR analysis was performed and revealed that compound (42) was still intact. As a result, the reaction solution was concentrated under reduced pressure at 40° C. to a dark orange oil. The oil was dissolved in CH$_2$Cl$_2$ (250 mL) and washed with H$_2$O (150 mL). The organic phase was concentrated under reduced pressure at 40° C. to obtain a dark orange oil. Upon standing, the oil turned into a crystalline orange solid. $^1$H NMR (300 MHz, CDCl$_3$) δ 8.46 (s, 1H), 8.37 (d, 2H, J=9 Hz), 7.99 (d, 2H, J=8.4 Hz), 7.50 (m, 4H), 6.11 (s, 2H), 4.95 (br t, 1H), 3.75 (dd, 6H, J=10.5 and 14.1 Hz), 3.2 (dd, 2H, J=10.3 and 13.2 Hz), 1.6 (m, 2H), 1.16 (t, 9H, J=6.9 Hz), 0.6 (t, 2H, J=8.2 Hz). $^{13}$C NMR (300 MHz, CDCl$_3$) δ 156.9, 131.6, 131.2, 129.2, 127.1, 126.8, 125.3, 124.4, 77.7, 77.3, 76.9, 59.2, 58.7, 43.8, 23.5, 18.5, 7.9. The crude material was used, in the glass slide derivatization experiment illustrated in Example 20.

Example 20

Functionalization of Glass Slides with Anthracene-Silane Reagent (42)

Figure 19:
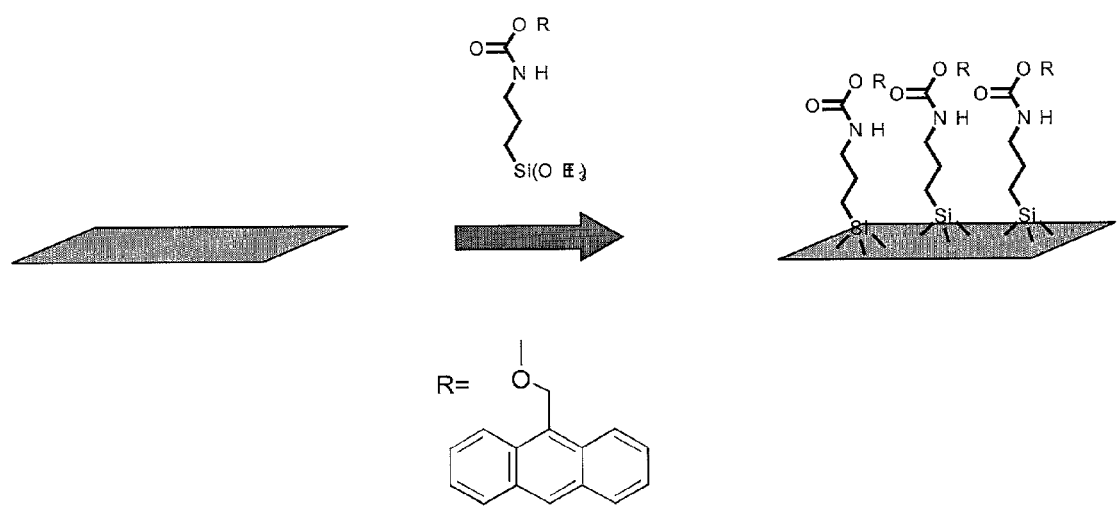
FIG. 19 illustrates the functionalization of glass microscope slides with anthracene-silane reagent (42).

Scheme 24 (FIG. 19) illustrates the functionalization of glass microscope slides with anthracene-silane reagent (42).

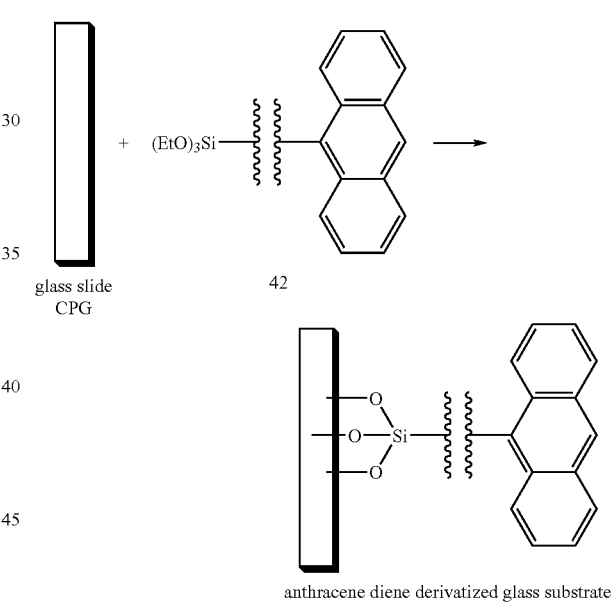

anthracene diene derivatized glass substrate

One half of a clean microslide (not pre-treated, VWR) was dipped into a suspension of reagent 42 (1.04 g) in toluene (50 mL) and CH$_2$Cl$_2$ (10 mL) for 1 hour. The slide was then removed from the suspension and blotted dry on a piece of filter paper. The slide was sonicated sequentially in toluene, toluene/ethanol (1:1, v/v) and ethanol (100 mL, each). For drying the slide was placed in an oven at 80° C. overnight.

TABLE 1

Known Methods for Immobilizing Biomolecules.

| Immobilization Chemistry | Reference | Process Time (conditions) |
|---|---|---|
| Hydrophobic (salt or detergent facilitated) | Nikifov et al. U.S. Pat. No. 5,610,287 (1997) | overnight (RT) |

TABLE 1-continued

Known Methods for Immobilizing Biomolecules.

| Immobilization Chemistry | Reference | Process Time (conditions) |
|---|---|---|
| Ionic (polylysine-coated microporous membrane + cDNA) | [1]Shalon et al. (1996) Brown et al. (1998) | 2 hours (h) (80° C.) |
| Disulfide formation | [2]Anderson et al. (1998) Rogers et al. (1999) | 2 h (>2 µM; RT) |
| Epoxide opening with 3'-amino oligonucleotide | [3]Stimpson (acid cat; 1995) Beattie (elev temp; 1995) Lamture (KOH; 1994) | >1 h (50 µg/mL in PBS; RT) |
| Epoxide opening with 3'- or 5'-hydroxyl of oligonucleotide | [4]Shi et al. (base cat; 1999) | 12+ h (0.25-10 µM; 65° C.) |
| Radical chemistry with –SH slides + underivatized oligonucleotides | Shi et al. (1999) (ref 4) | overnight (0.25-10 µM; RT) |
| Activated polypropylene or glass + amino oligodeoxyribonucleo-tides, PCR-products and PNA-oligomers; Surfaces activated as: a) isothiocyanate (phenyldiisothiocyanate) b) succinimidyl carbonate (DSC) c) succinimidyloxalate (DSO) d) dimethylsuberimidate | [5]Beier and Hoheisel (1999) | a)-d) overnight (0.1-1 µM, 37° C.) |
| Gold surface + thioate oligonucleotides | [6]Beebe et al. (1995) | 10+ hours (3-10 µg/mL; RT) |
| Carboxy oligonucleotides + amine slide | [7]Joos et al. (1997) | 1 h (max 50% yield; pH = 3.6; 0.05-50 pmol/15 µL; RT) |
| p-Nitrophenyl ester oligonucleotides + poly-lysine coated 96 well plates | [8]Nikiforov and Rogers (1995) | overnight (150-200 pmol/40-50 µL; RT) |
| Carboxy plates + amino oligonucleotides | Joos et al. (1997) (ref. 7) | overnight (10 pmol/ well; RT) |
| Biotin cDNA + Strepavidin-coated 96 well plates | [9]Holmstrom et al. (1993) | 30 minutes (RT) |
| Hydrazide gel (3D) + aldehyde oligonucleotide | [10]Yershov et al. (1996) | 48 h (quantitative; 20° C.) |
| Functionalized polyacrylamide gel matrices + oligonucleotides: a) hydrazide gel/amino oligo b) reductive amination (via NaCNBH₃, Me₃NBH₃ or PyrBH₃) c) 1° MsO-gel/amino oligo/K₂CO₃ d) glutaraaldehyde gel/ amino oligonucleotides | [11]Timofeev et al. (1996) | a) overnight (87%) b) 1.5 h (60-74% amine gel/ald oligo 94-97% aldehyde gel/ amine oligo) c) overnight (35%) d) overnight (71% + 17% non-specific binding) Note: All linkages were somewhat unstable in 0.1 MTEAA buffer (pH = 7), 60° C.;due to polymer degradation. |
| Maleimide surface/thiol oligonucleotides | [12]Chrisey et al. (1996) | 5 min-8 h (0.1-0.5 µM; RT; 34-73%) |
| Isothiocyanate/amino oligonucleotides | [13]Guo et al. (1994) | 1 h (0.1-20 mM; 37° C.) |
| Amine 96 well plates/NHS ester oligonucleotides | [14]Running and Urdea (1990) | 30 min (1.2 mM; RT) |
| Functionalized acrylamide derivatives/oligonucleotides a) bromoacetyl Biogel beads/thio oligonucleotides b) sulfhydryl beads (Biogel or trisacryl)/bromoacetyl oligonucleotides | [15]Fahy et al. (1993) | a) overnight (25 pmol/ 150 µL; pH 9; 5-43% yield) b) overnight (500 pmol/mL, pH = 9) |
| Activated carboxylate filter membrane (act. w/ EDC)/ amino oligonucleotides | [16]Zhang et al. (1991) | 15 min-2 h (RT; pH = 8.4; 80-90% attached w/90% specificity) |
| Boronic acid-modified protein/hydroxamate modified protein (solution phase conjugation) | [17]Rogers et al. (1997) | 30 min (RT) |
| Streptavidin agarose gel coated chip/ biotinylated cDNA | [18]Gilles et al. (1999) | 120 s (electronic addressing) |
| Polystyrene or polycarbonate plates/anthraquinone oligos or cDNA with irradiation | [19]Koch et al. (1999) | 10 min (0.3-20 µM) |
| Photochemical immobilization of anthraquinone-conjugated oliogonucleotides, DNA, and PCR amplicons on a variety of solid surfaces | [20]Koch et al. (2000) | 15 min (irradiation) |

[1]Shalon et al. (1996) Genome Research 639-645; Brown and Shalon (1998) U.S. Pat. No. 5,807,522.
[2]Anderson and Rogers (1998) U.S. Pat. No. 5,837,860; Rogers et al. (1999) Analytical Biochemistry 266: 23-30.
[3]Stimpson et al. (1995) Proc. Natl. Acad. Sci. USA 92: 6379-6383; Beattie et al. (1995) Clin. Chem. 41: 700-706; Lamture et al. (1994) Nucleic Acids Research 22: 2121-25.
[4]Shi and Boyce-Jacino (1999) U.S. Pat. No. 5,919,626.
[5]Beier and Hoheisel (1999) Nucleic Acids Research 27(9): 1970-1977.
[6]Beebe and Rabke-Clemmer (1995) U.S. Pat. No. 5,472,881.
[7]Joos et al. (1997) Analytical Biochemistry 247: 96-101.
[8]Nikiforov and Rogers (1995) Analytical Biochemistry 227: 201-209.
[9]Holmstrom et al. (1993) Analytical Biochemistry 209: 278-283.
[10]Yershov et al. (1996) Proc. Natl. Acad. Sci. USA 93: 4913-4918.
[11]Timofeev et al. (1996) Nucleic Acids Research 24(16): 3142-3148.
[12]Chrisey et al. (1996) Nucleic Acids Research 24(16): 3031-3039.
[13]Guo et al. (1994) Nucleic Acids Research 22 (24): 5456-5465.
[14]Running and Urdea (1990) BioTechniques 8 (3): 276-277.
[15]Fahy et al. (1993) Nucleic Acids Research 21(8): 1819-1826.
[16]Zhang et al. (1991) Nucleic Acids Research 19(14): 3929-3933.
[17]Rogers et al. (1997) Gene Therapy 4: 1387-1392.
[18]Gilles et al. (1999) Nature Biotechnolgy 17:365.
[19]Koch et al. (Exiqon) 1999.
[20]Koch et al. (2000) Bioconjugate Chem. 11: 474-483.

TABLE 2

Results from the Conjugation of Oligonucleotide (24) to maleimide CPG (Example 10)

| Concentration of (24) ABS [nmol/µL] | ABS [ ] | CPG-Loading [µmol/g] |
|---|---|---|
| 0.30 | 0.549 | 0.771 |
| 0.37 | 0.583 | 0.819 |
| 0.44 | 0.655 | 0.920 |
| 0.52 | 0.718 | 1.008 |
| 0.67 | 0.847 | 1.190 |
| 0.74 | 0.896 | 1.258 |
| 0.93 | 1.013 | 1.423 |
| 1.10 | 1.199 | 1.684 |

TABLE 3

Time Dependence of the Rreaction Between Oligonucleotide (24) and Maleimide CPG (Example 10)

| Reaction Time [min] | ABS [ ] | CPG-Loading [μmol/g] |
|---|---|---|
| 5 | 0.300 | 0.421 |
| 10 | 0.363 | 0.510 |
| 20 | 0.440 | 0.618 |
| 40 | 0.548 | 0.770 |
| 60 | 0.628 | 0.882 |
| 90 | 0.658 | 0.924 |

TABLE 5

Chromatography Conditions (Example 13)

| Time (min) | % Eluent B | Gradient Method |
|---|---|---|
| 0 | 0 | Linear |
| 21 | 30 | Linear |
| 22 | 100 | Linear |
| 32 | 100 | Isocratic |
| 33 | 0 | Linear |
| 42 | 0 | Isocratic |

Eluent A: TEAA (pH = 7.0)
Eluent B: Acetonitrile

TABLE 4

Chromatography Conditions (Example 12)

| Time (min) | % Eluent B | Gradient method |
|---|---|---|
| 0 | 0 | Linear |
| 10 | 10 | Linear |
| 27 | 15 | Linear |

Buffer A: 25 mM Na$_2$HPO$_3$ solution (pH = 7.5) with 10% EtOH.
Buffer B: 2 M NaBr solution with 10% EtOH.

The invention claimed is:

1. A method for immobilizing a molecule on a support comprising the steps of:
   a) derivatizing the molecule with a functional group capable of undergoing a cycloaddition reaction, wherein said derivatization is independent of the synthesis of the molecule; and
   b) immobilizing the derivatized molecule by reaction with a derivatized support capable of reacting with said derivatized molecule via a cycloaddition reaction.

2. The method of claim 1 wherein said cycloaddition reaction is selected from the group consisting of a [1+2]-cycloaddition, [2+2]-cycloaddition, [3+2]-cycloaddition, [2+4]-cycloaddition, [4+6]-cycloaddition, and cheleotropic reactions.

3. The method of claim 2 wherein said cycloaddition reaction is selected from the group consisting of a 1,3-dipolar cycloaddition, a Diels-Alder reaction, an ene reaction and a [2+2] photochemical cycloaddition reaction.

4. The method of claim 1 wherein said molecule is derivatized with a moiety selected from the group consisting of a diene or dienophile, with or without heteroatoms, a 1,3-dipole or 1,3-dipolarophile, with or without heteroatoms, an ene or enophile, with or without heteroatoms a C2-C50 alkene, with or without heteroatoms, a C2-C50 alkyne, with or without a heteroatoms, aromatic compounds, carbenes and carbene precursors.

5. The method of claim 1 wherein said derivatized molecule is an oligonucleotide selected from the group of compounds having the following formulas:

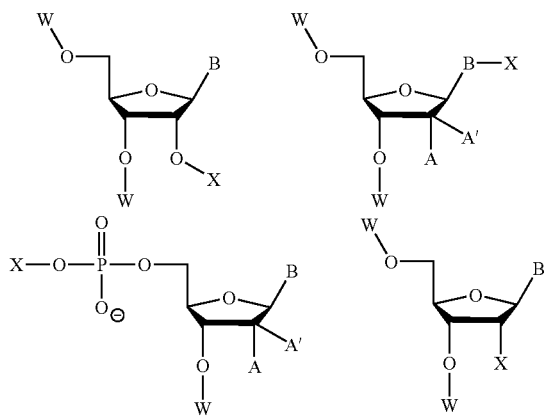

wherein

B is a nucleobase;

A and A' are 2'-sugar substituents;

W is independently selected from the group consisting of an oligonucleotide having between 1-1000 nucleobases, X or H; and X is a diene, dienophile, 1,3-dipole, 1,3 dipolarophile, ene, enophile, alkene, alkyne or other moiety, capable of undergoing a cycloaddition reaction, additionally when X is attached to nucleobase B it can be attached to a carbon atom, an exocyclic nitrogen or an exocyclic oxygen.

6. The method of claim 5 wherein

A and A' are independently selected from the group consisting of H, $^2$H, $^3$H, Cl, F, OH, NHOR$^1$, NHOR$^3$, NHNHR$^3$, NHR$^3$, =NH, CHCN, CHCl$_2$, SH, SR$_3$, CFH$_2$, CF$_2$H, CR$^2{}_2$Br, —(OCH$_2$CH$_2$)$_n$OCH$_3$, OR$^4$, and imidazole;

R$^1$ is selected from the group consisting of H and an alcohol protecting group;

R$^2$ is selected from the group consisting of =O, =S, H, OH, CCl$_3$, CF$_3$, halide, optionally substituted C$_1$-C$_{20}$ alkyl (including cyclic, straight chain, and branched), C$_2$-C$_{20}$ alkenyl, C$_6$-C$_{20}$ aryl, C1-C20 acyl, C$_1$-C$_{20}$ benzoyl, OR$_4$ and esters;

R$^3$ is selected from the group consisting of R$^2$, R$^4$, CN, C(O)NH$_2$, C(S)NH$_2$, C(O)CF$_3$, SO$_2$R$^4$, amino acid, peptide and mixtures thereof;

R$^4$ is selected from the group consisting of an optionally substituted hydrocarbon (C$_1$-C$_{20}$ alkyl, C$_2$-C$_{20}$ alkenyl, C$_2$-C$_{20}$ alkynyl), an optionally substituted heterocycle, t-butyldimethylsilyl ether, triisopropylsilyl ether, nucleoside, carbohydrate, fluorescent label and phosphate; and X is selected from the group consisting of alkyl or substituted alkyl group bearing a conjugated diene unit, an alkoxy or substituted alkoxy group bearing a conjugated diene unit, CH$_2$CHCH=CHCH$_2$CH$_2$O, maleinide substituted alkoxy groups, dienophile substituted alkoxy groups, an alkylamino group or substituted alkylamino group bearing a conjugated diene unit, maleimide substituted alkylamino groups or substituted alkylamino groups, an alkylamino group or substituted alkylamino group bearing a dienophile moiety, a nitrile ylid, nitrile imine, nitrile oxide, diazoalkane, azide, azomethine ylid, azomethine imine, nitrone, carbonyl ylid, carbonyl imine and carbonyl oxide.

7. The method of claim 1 wherein said support is selected from the group consisting of glass, polymers and resins, and large biomolecules.

8. The method of claim 7 wherein said glass is selected from the group consisting of controlled pore glass (CPG), glass slides, glass fibers, glass disks and materials coated with glass.

9. The method of claim 7 wherein said polymers and resins are selected from the group consisting of polystyrene (PS), polyethylene glycol (PEG), copolymers of PS and PEG, copolymers of polyacrylamide and PEG and copolymers containing maleimide or maleic anhydride, polyvinyl alcohol and immunogenic high molecular weight compounds.

10. The method of claim 7 wherein said large biomolecules are selected from the group consisting of polysaccharides, proteins and nucleic acids.

11. The method of claim 1 wherein said support is a solid support.

12. The method of claim 1 wherein said support is derivatized with a moiety selected from the group consisting of a diene or dienophile, with or without heteroatoms, a 1,3-dipole or 1,3-dipolarophile, with or without heteroatoms, an ene or enophile, with or without heteroatoms, a C2-C50 alkene, with or without heteroatoms, a C2-C50 alkyne, with or without heteroatoms, aromatic compounds, carbenes and carbene precursors.

13. An immobilized product formed by the method of claim 1.

14. A method for immobilizing a molecule on a support comprising the step of reacting a derivatized molecule with a derivatized support capable of reacting with said derivatized molecule via a cycloaddition reaction, wherein said molecule is a diagnostic detector molecule (DDM).

15. The method of claim 14 wherein said DDM is selected from the group consisting of fluorescent, chemiluminescent, radioisotope and bioluminescent marker compounds; antibodies, biotin and metal chelates.

16. The method of claim 14 wherein said DDM is fluorescein.

17. A method for immobilizing a molecule on a support comprising the step of reacting a derivatized molecule with a support capable of reacting with said derivatized molecule via a cycloaddition reaction, wherein said molecule is derivatized with a diene selected from the group consisting of:

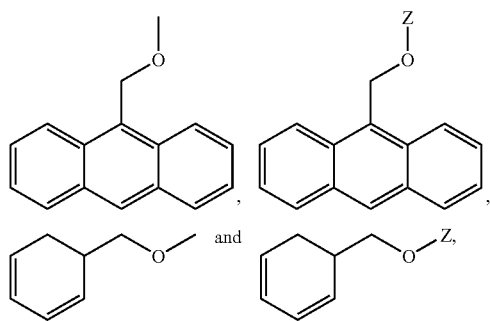

wherein
Z is a linker selected from the group consisting of:

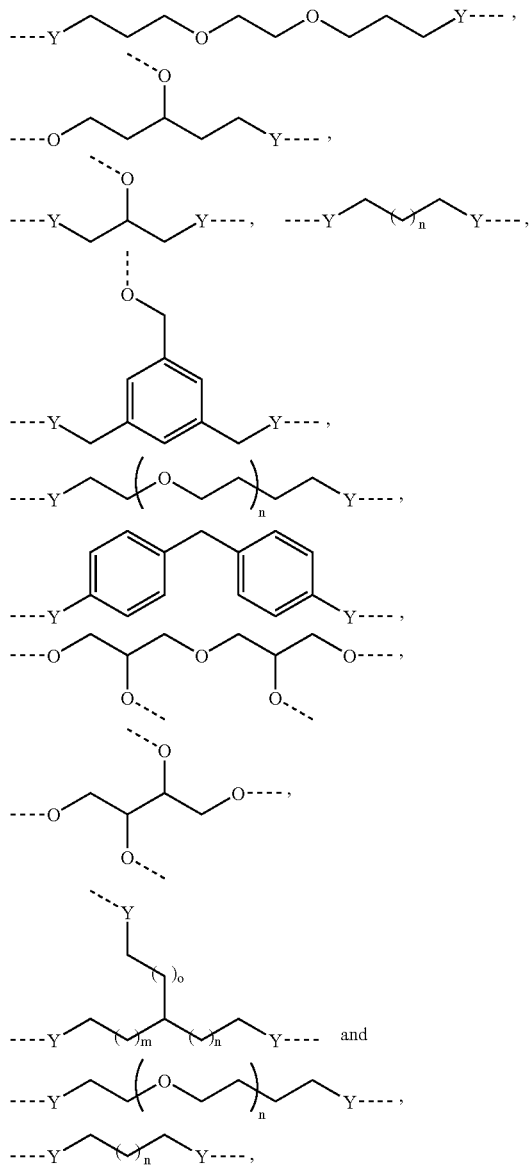

wherein
m, n, o are equal to 0, 1, 2 and
Y is selected from NH, O, NH(CO)O, NH(CS)O, NH(CO)NH, NH(CO), S—S—S—, Si(OR)$_3$ and SiR$_2$ wherein
R is selected from alkyl, aryl, substituted alkyl or substituted aryl.

18. A method for immobilizing a molecule on a support comprising the step of reacting a derivatized molecule with a support capable of reacting with said derivatized molecule via a cycloaddition reaction, wherein said molecule is derivatized with a dienophile selected from the group consisting of:

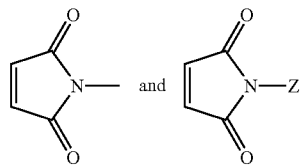

wherein
Z is a linker selected from the group consisting of:

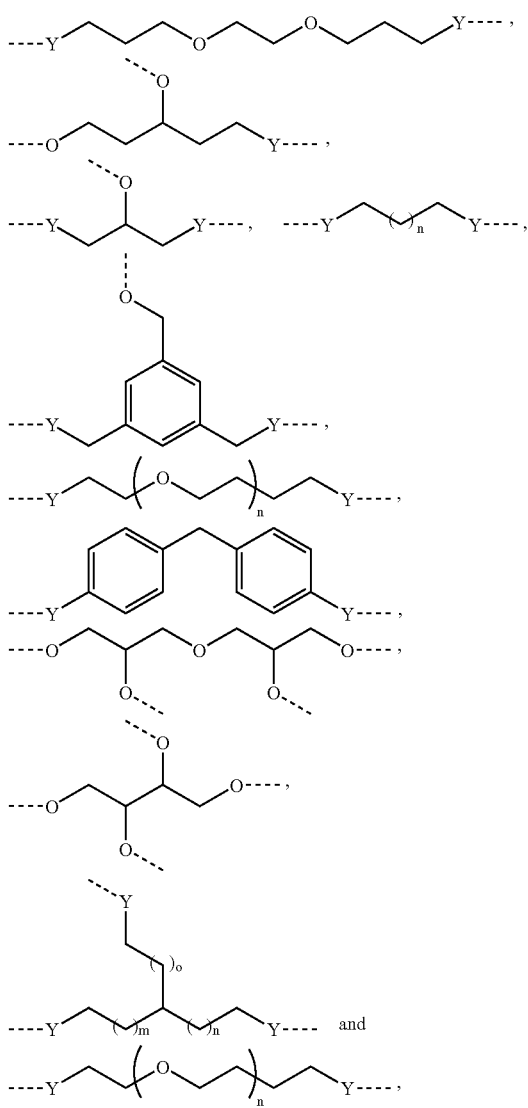

-continued $$\text{----Y}\overbrace{\phantom{xxx}}_{n}\text{Y----},$$

wherein m, n, o are equal to 0, 1, 2 and

Y is selected from NH, O, NH(CO)O, NH(CS)O, NH(CO)NH, NH(CO), S—S—S—, Si(OR)$_3$ and SiR$_2$ wherein R is selected from alkyl, aryl, substituted alkyl or substituted aryl.

19. A method for immobilizing a molecule on a support comprising the step of reacting said molecule with a support capable of reacting with said molecule via a cycloaddition reaction wherein said support is derivatized with a diene selected from the group consisting of:

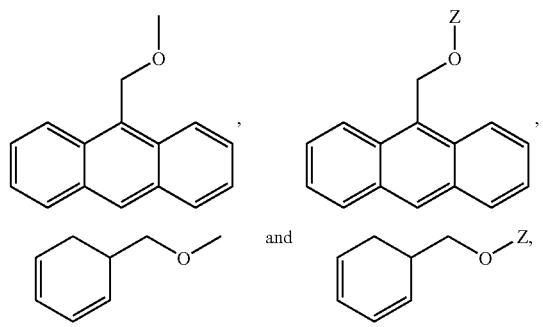

wherein

Z is a linker selected from the group consisting of:

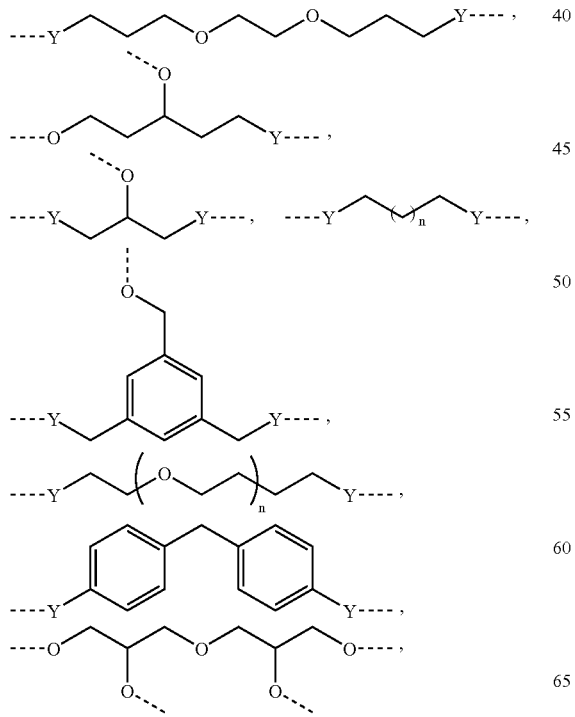

-continued

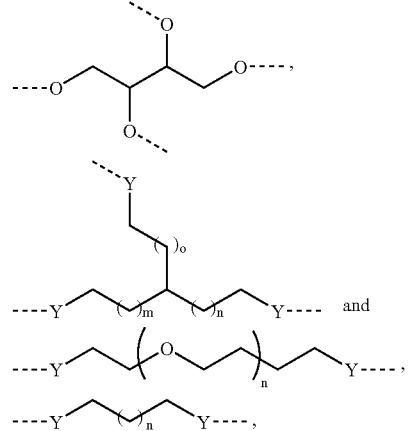

wherein m, n, o are equal to 0, 1, 2 and

Y is selected from NH, O, NH(CO)O, NH(CS)O, NH(CO)NH, NH(CO), S—S—S—, Si(OR)$_3$ and SiR$_2$ wherein R is selected from alkyl, aryl, substituted alkyl or substituted aryl.

20. A method for immobilizing a molecule on a support comprising the step of reacting said molecule with a support capable of reacting with said molecule via a cycloaddition reaction wherein said support is derivatized with a dienophile selected from the group consisting of:

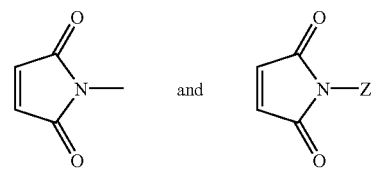

wherein

Z is a linker selected from the group consisting of:

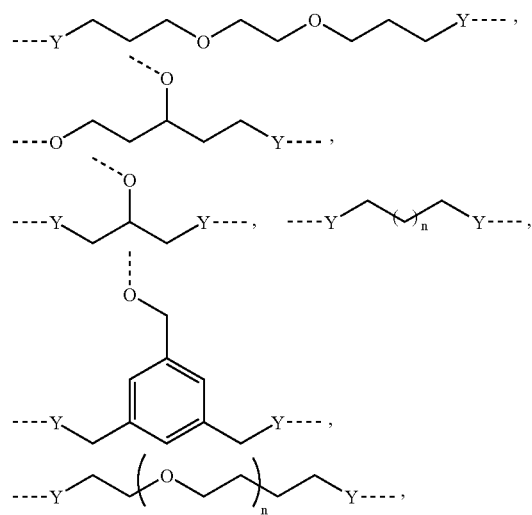

-continued
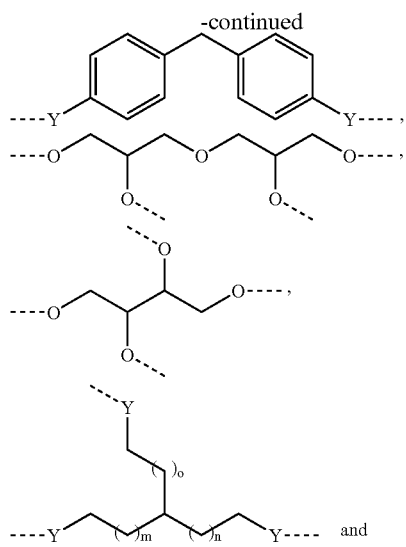
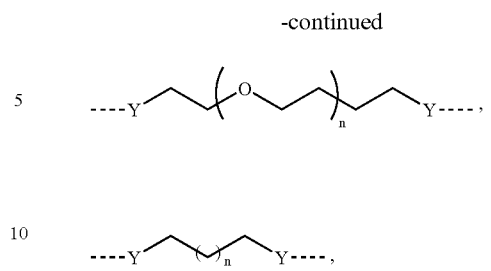
wherein
m, n, o are equal to 0, 1, 2 and
Y is selected from NH, O, NH(CO)O, NH(CS)O, NH(CO)NH, NH(CO), S—S—S—, Si(OR)$_3$ and SiR$_2$ wherein R is selected from alkyl, aryl, substituted alkyl or substituted aryl.
* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      Nucleic Acid Ligand

<400> SEQUENCE: 1
tgtgtgtgtg tgtgtgtgtg                                            20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      Nucleic Acid Ligand
<220> FEATURE:
<221> NAME/KEY: modified_base
<222> LOCATION: (1)
<223> OTHER INFORMATION: C at position 1 is substituted at the 5'
      position with a fluorescein.

<400> SEQUENCE: 2
cacacacaca cacacacaca                                            20
```